(12) United States Patent
Niemöeller et al.

(10) Patent No.: US 9,408,893 B2
(45) Date of Patent: Aug. 9, 2016

(54) PHARMACEUTICAL COMBINATION FOR USE IN GLYCEMIC CONTROL IN DIABETES TYPE 2 PATIENTS

(75) Inventors: Elisabeth Niemöeller, Frankfurt am Main (DE); Isabel Müehlen-Bartmer, Frankfurt am Main (DE); Louise Silvestre, Paris (FR); Gabor Boka, Paris (FR); Patrick Miossec, Paris (FR)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 13/595,590

(22) Filed: Aug. 27, 2012

(65) Prior Publication Data

US 2013/0203666 A1 Aug. 8, 2013

(30) Foreign Application Priority Data

Aug. 29, 2011 (EP) ..................................... 11179149

(51) Int. Cl.
| | | |
|---|---|---|
| *A61K 38/26* | (2006.01) | |
| *C07K 14/605* | (2006.01) | |
| *A61P 3/10* | (2006.01) | |
| *A61K 31/155* | (2006.01) | |
| *A61K 31/4439* | (2006.01) | |
| *A61K 31/427* | (2006.01) | |

(52) U.S. Cl.
CPC ................ *A61K 38/26* (2013.01); *A61K 31/155* (2013.01); *A61K 31/427* (2013.01); *A61K 31/4439* (2013.01)

(58) Field of Classification Search
CPC . A61K 38/26; A61K 31/155; A61K 31/4439; A61K 31/427; A61K 2300/00
See application file for complete search history.

(56) References Cited

U.S. PATENT DOCUMENTS

| | | |
|---|---|---|
| 3,758,683 A | 9/1973 | Jackson |
| 3,868,358 A | 2/1975 | Jackson |
| 3,984,696 A | 10/1976 | Collica et al. |
| 4,153,689 A | 5/1979 | Hirai et al. |
| 4,258,134 A | 3/1981 | Yoshida et al. |
| 4,367,737 A | 1/1983 | Kozam et al. |
| 4,608,364 A | 8/1986 | Grau |
| 4,614,730 A | 9/1986 | Hansen et al. |
| 4,644,057 A | 2/1987 | Bicker et al. |
| 4,689,042 A | 8/1987 | Sarnoff et al. |
| 4,701,440 A | 10/1987 | Grau |
| 4,731,405 A | 3/1988 | Kirsch et al. |
| 4,783,441 A | 11/1988 | Thurow |
| 4,839,341 A | 6/1989 | Massey et al. |
| 4,863,902 A | 9/1989 | Amagase et al. |
| 4,885,164 A | 12/1989 | Thurow |
| 4,923,162 A | 5/1990 | Fleming et al. |
| 4,959,351 A | 9/1990 | Grau |
| 4,960,702 A | 10/1990 | Rice et al. |
| 4,994,439 A | 2/1991 | Longenecker et al. |
| 5,006,718 A | 4/1991 | Lenhart |
| 5,008,241 A | 4/1991 | Markussen et al. |
| 5,034,415 A | 7/1991 | Rubin |
| 5,070,186 A | 12/1991 | Joergensen |
| 5,101,013 A | 3/1992 | Dorschug et al. |
| 5,177,058 A | 1/1993 | Dorschug |
| 5,187,177 A | 2/1993 | Garzaran |
| 5,227,293 A | 7/1993 | Stengelin et al. |
| 5,253,785 A | 10/1993 | Haber et al. |
| 5,272,135 A | 12/1993 | Takruri |
| 5,358,708 A | 10/1994 | Patel |
| 5,358,857 A | 10/1994 | Stengelin et al. |
| 5,370,629 A | 12/1994 | Michel et al. |
| 5,397,771 A | 3/1995 | Bechgaard et al. |
| 5,407,609 A | 4/1995 | Tice et al. |
| 5,424,286 A | 6/1995 | Eng |
| 5,428,006 A | 6/1995 | Bechgaard et al. |
| 5,473,049 A | 12/1995 | Obermeier et al. |
| 5,474,978 A | 12/1995 | Bakaysa et al. |
| 5,478,323 A | 12/1995 | Westwood et al. |
| 5,496,924 A | 3/1996 | Habermann et al. |
| 5,506,203 A | 4/1996 | Backstrom et al. |
| 5,509,905 A | 4/1996 | Michel et al. |
| 5,514,646 A | 5/1996 | Chance et al. |
| 5,524,286 A | 6/1996 | Chiesa et al. |
| 5,535,488 A | 7/1996 | Hoffman |
| 5,545,618 A | 8/1996 | Buckley et al. |
| 5,547,929 A | 8/1996 | Anderson, Jr. et al. |
| 5,559,094 A | 9/1996 | Brems et al. |
| 5,595,756 A | 1/1997 | Bally et al. |
| 5,597,796 A | 1/1997 | Brange |
| 5,614,219 A | 3/1997 | Wunderlich et al. |

(Continued)

FOREIGN PATENT DOCUMENTS

| | | |
|---|---|---|
| AU | 1986-62066 | 3/1987 |
| AU | 1987-75916 | 1/1988 |

(Continued)

OTHER PUBLICATIONS

Christensen et al, Lixisenatide, a noveL GLP-1 receptor agonist for the treatment of type 2 diabetes mellitus, IDrugs, 2009, 12, pp. 503-513.*
NCT00763815, from http://clinicaltrials.gov/ct2/show/NCT00763815?term=NCT00763815&rank=1, pp. 1-3, accessed Sep. 12, 2013.*
Yki-Järvinen et al, Insulin glargine or NPH combined with metformin in type 2 diabetes: the LANMET study, Diabetologia, 2006, 49, pp. 442-451.*

(Continued)

*Primary Examiner* — Julie Ha
*Assistant Examiner* — Li Ni Komatsu
(74) *Attorney, Agent, or Firm* — McDonnell Boehnen Hulbert & Berghoff LLP

(57) ABSTRACT

The present invention refers to a pharmaceutical combination for use in glycemic control in diabetes type 2 patients.

2 Claims, 4 Drawing Sheets

(56) References Cited

U.S. PATENT DOCUMENTS

| | | |
|---|---|---|
| 5,614,492 A | 3/1997 | Habener |
| 5,631,224 A | 5/1997 | Efendic et al. |
| 5,654,008 A | 8/1997 | Herbert et al. |
| 5,656,722 A | 8/1997 | Dorschug |
| 5,663,291 A | 9/1997 | Obermeier et al. |
| 5,670,360 A | 9/1997 | Thorens |
| 5,693,608 A | 12/1997 | Bechgaard et al. |
| 5,700,662 A | 12/1997 | Chance et al. |
| 5,707,641 A | 1/1998 | Gertner et al. |
| 5,783,556 A | 7/1998 | Clark et al. |
| 5,824,638 A | 10/1998 | Burnside et al. |
| 5,846,747 A | 12/1998 | Thorens et al. |
| 5,846,937 A | 12/1998 | Drucker |
| 5,948,751 A | 9/1999 | Kimer et al. |
| 5,952,297 A | 9/1999 | DeFelippis et al. |
| 5,981,964 A | 11/1999 | McAuley et al. |
| 5,985,309 A | 11/1999 | Edwards et al. |
| 6,006,753 A | 12/1999 | Efendic |
| 6,034,054 A | 3/2000 | DeFelippis et al. |
| 6,043,214 A | 3/2000 | Jensen et al. |
| 6,051,551 A | 4/2000 | Hughes et al. |
| 6,051,689 A | 4/2000 | Thorens |
| 6,100,376 A | 8/2000 | Dorschug |
| 6,110,703 A | 8/2000 | Egei-Mitani et al. |
| 6,174,856 B1 | 1/2001 | Langballe et al. |
| 6,191,102 B1 | 2/2001 | DiMarchi et al. |
| 6,211,144 B1 | 4/2001 | Havelund |
| 6,227,819 B1 | 5/2001 | Gettel et al. |
| 6,248,363 B1 | 6/2001 | Patel et al. |
| 6,267,981 B1 | 7/2001 | Okamoto et al. |
| 6,268,335 B1 | 7/2001 | Brader |
| 6,268,343 B1 | 7/2001 | Knudsen et al. |
| 6,271,241 B1 | 8/2001 | DeSimone et al. |
| 6,284,725 B1 | 9/2001 | Coolidge et al. |
| 6,309,663 B1 | 10/2001 | Patel et al. |
| 6,310,038 B1 | 10/2001 | Havelund |
| 6,329,336 B1 | 12/2001 | Briden et al. |
| 6,335,316 B1 | 1/2002 | Hughes et al. |
| 6,344,180 B1 | 2/2002 | Holst et al. |
| 6,358,924 B1 | 3/2002 | Hoffmann |
| 6,384,016 B1 | 5/2002 | Kaarsholm |
| 6,388,053 B1 | 5/2002 | Galloway et al. |
| 6,395,767 B2 | 5/2002 | Robl et al. |
| 6,410,508 B1 | 6/2002 | Isales et al. |
| 6,417,164 B1 | 7/2002 | Kolterman |
| 6,444,641 B1 | 9/2002 | Flora |
| 6,468,959 B1 | 10/2002 | Wunderlich et al. |
| 6,489,292 B1 | 12/2002 | Havelund et al. |
| 6,528,486 B1 | 3/2003 | Larsen et al. |
| 6,734,162 B2 | 5/2004 | Van Antwerp et al. |
| 6,767,887 B1 | 7/2004 | Hoffmann et al. |
| 6,818,738 B2 | 11/2004 | Havelund |
| 6,852,694 B2 | 2/2005 | Van Antwerp et al. |
| 6,875,589 B1 | 4/2005 | Dorschug et al. |
| 6,908,610 B1 | 6/2005 | Sato |
| 6,908,897 B2 | 6/2005 | Brandenburg et al. |
| 6,960,561 B2 | 11/2005 | Boderke |
| 6,969,702 B2 | 11/2005 | Bertilsson et al. |
| 7,022,674 B2 | 4/2006 | DeFelippis |
| 7,115,563 B2 | 10/2006 | Younis |
| 7,119,086 B2 | 10/2006 | Di Malta et al. |
| 7,192,919 B2 | 3/2007 | Tzannis et al. |
| 7,205,276 B2 | 4/2007 | Boderke |
| 7,205,277 B2 | 4/2007 | Boderke |
| 7,238,663 B2 | 7/2007 | DeFelippis et al. |
| 7,405,196 B2 | 7/2008 | Rosskamp et al. |
| 7,476,652 B2 | 1/2009 | Brunner-Schwarz et al. |
| 7,544,656 B2 | 6/2009 | Sabetsky |
| 7,544,657 B2 | 6/2009 | Ebbehoj et al. |
| 7,576,050 B2 | 8/2009 | Greig et al. |
| 7,713,930 B2 | 5/2010 | Brunner-Schwarz et al. |
| 7,803,763 B2 | 9/2010 | Thurow et al. |
| 7,807,242 B2 | 10/2010 | Soerensen et al. |
| 7,918,833 B2 | 4/2011 | Veasey et al. |
| 7,939,293 B2 | 5/2011 | Habermann et al. |
| 7,977,310 B2 | 7/2011 | Rosskamp et al. |
| 8,048,854 B2 | 11/2011 | Habermann et al. |
| 8,084,420 B2 | 12/2011 | Steiner et al. |
| 8,092,421 B2 | 1/2012 | Seiferlein et al. |
| 8,092,422 B2 | 1/2012 | Seiferlein et al. |
| 8,178,495 B2 | 5/2012 | Chilkoti |
| 8,574,214 B2 | 11/2013 | Kuhn et al. |
| 8,633,156 B2 | 1/2014 | Habermann et al. |
| 8,735,349 B2 | 5/2014 | Silvestre et al. |
| 2001/0012829 A1 | 8/2001 | Anderson et al. |
| 2001/0033868 A1 | 10/2001 | Rossling et al. |
| 2001/0039260 A1 | 11/2001 | Havelund |
| 2001/0047084 A1 | 11/2001 | Knudsen et al. |
| 2002/0107265 A1 | 8/2002 | Chen et al. |
| 2002/0132760 A1 | 9/2002 | Van Antwerp et al. |
| 2002/0177151 A1 | 11/2002 | Gimeno |
| 2002/0198140 A1 | 12/2002 | Havelund |
| 2003/0004096 A1 | 1/2003 | Boderke |
| 2003/0026872 A1 | 2/2003 | Dake et al. |
| 2003/0104983 A1 | 6/2003 | DeFelippis et al. |
| 2003/0170691 A1 | 9/2003 | Gimeno |
| 2004/0048783 A1 | 3/2004 | Brunner-Schwarz et al. |
| 2004/0092590 A1 | 5/2004 | Arteburn et al. |
| 2004/0097410 A1 | 5/2004 | Zheng et al. |
| 2004/0106547 A1 | 6/2004 | Larsen et al. |
| 2004/0186046 A1 | 9/2004 | Burgess et al. |
| 2004/0229774 A1 | 11/2004 | Rosskamp et al. |
| 2004/0235710 A1 | 11/2004 | DeFelippis et al. |
| 2005/0014679 A1 | 1/2005 | Beals et al. |
| 2005/0079996 A1 | 4/2005 | Horiguchi et al. |
| 2005/0106147 A1 | 5/2005 | Jordan et al. |
| 2005/0171009 A1 | 8/2005 | Brunner-Schwarz et al. |
| 2005/0209142 A1 | 9/2005 | Bertilsson et al. |
| 2006/0004049 A1 | 1/2006 | Yao et al. |
| 2006/0014678 A1 | 1/2006 | Cowley et al. |
| 2006/0019347 A1 | 1/2006 | Cho et al. |
| 2006/0057137 A1 | 3/2006 | Steiness |
| 2006/0073213 A1 | 4/2006 | Hotamisligil et al. |
| 2006/0093576 A1 | 5/2006 | Chen et al. |
| 2006/0194719 A1 | 8/2006 | Ebbehoj et al. |
| 2006/0239933 A1 | 10/2006 | Nilsson et al. |
| 2006/0287221 A1 | 12/2006 | Knudsen et al. |
| 2007/0027063 A1 | 2/2007 | Boss et al. |
| 2007/0111940 A1 | 5/2007 | Larsen et al. |
| 2007/0128193 A1 | 6/2007 | O'Neil et al. |
| 2007/0135338 A1 | 6/2007 | O'Neil et al. |
| 2007/0155653 A1 | 7/2007 | Boderke |
| 2007/0191271 A1 | 8/2007 | Mayhew et al. |
| 2007/0237827 A1 | 10/2007 | Sung et al. |
| 2008/0146490 A1 | 6/2008 | Joabsson et al. |
| 2008/0234200 A1 | 9/2008 | Quay et al. |
| 2008/0248999 A1 | 10/2008 | Steiner |
| 2008/0260840 A1 | 10/2008 | Alessi et al. |
| 2008/0267907 A1 | 10/2008 | Poulsen |
| 2009/0082255 A1 | 3/2009 | Brunner-Schwarz et al. |
| 2009/0088369 A1 | 4/2009 | Steiness |
| 2009/0099064 A1 | 4/2009 | Lougheed |
| 2009/0175840 A1 | 7/2009 | Kashyap et al. |
| 2009/0176692 A1 | 7/2009 | Habermann et al. |
| 2009/0180953 A1 | 7/2009 | Gotthardt et al. |
| 2009/0186819 A1 | 7/2009 | Carrier et al. |
| 2009/0208565 A1 | 8/2009 | Ebbehoj et al. |
| 2009/0214657 A1 | 8/2009 | Qazi |
| 2009/0304665 A1 | 12/2009 | Frost et al. |
| 2009/0312236 A1 | 12/2009 | Beals et al. |
| 2009/0324701 A1 | 12/2009 | Williams |
| 2010/0029558 A1 | 2/2010 | Bristow |
| 2010/0055049 A1 | 3/2010 | Kuo et al. |
| 2010/0057194 A1 | 3/2010 | Ryan |
| 2010/0069292 A1 | 3/2010 | Pohl et al. |
| 2010/0069293 A1 | 3/2010 | Bolotin et al. |
| 2010/0227816 A1 | 9/2010 | Fiatt et al. |
| 2010/0279931 A1 | 11/2010 | Garibay et al. |
| 2010/0311112 A1 | 12/2010 | Rissom et al. |
| 2011/0020294 A1 | 1/2011 | Hammerman |
| 2011/0021423 A1 | 1/2011 | Olsen et al. |
| 2011/0077197 A1 | 3/2011 | Habermann et al. |
| 2011/0118178 A1 | 5/2011 | Silvestre et al. |
| 2011/0118180 A1 | 5/2011 | Silvestre et al. |

(56) References Cited

U.S. PATENT DOCUMENTS

| | | |
|---|---|---|
| 2011/0144008 A1 | 6/2011 | Larsen et al. |
| 2011/0152185 A1 | 6/2011 | Plum et al. |
| 2011/0173722 A1 | 7/2011 | Habermann et al. |
| 2011/0230402 A1 | 9/2011 | Johansen et al. |
| 2011/0236925 A1 | 9/2011 | Hazra et al. |
| 2011/0245165 A1 | 10/2011 | Larsen et al. |
| 2011/0281790 A1 | 11/2011 | Pohl et al. |
| 2011/0301081 A1 | 12/2011 | Becker et al. |
| 2012/0021978 A1 | 1/2012 | Werner et al. |
| 2012/0121611 A1 | 5/2012 | Lodie et al. |
| 2012/0122774 A1 | 5/2012 | Becker et al. |
| 2012/0183616 A1 | 7/2012 | Sprogoe et al. |
| 2012/0232002 A1 | 9/2012 | Schoettle et al. |
| 2012/0241356 A1 | 9/2012 | Pfenninger et al. |
| 2012/0252724 A1 | 10/2012 | Schoettle et al. |
| 2012/0277147 A1 | 11/2012 | Boka et al. |
| 2012/0283179 A1 | 11/2012 | Brunner-Schwarz et al. |
| 2012/0295846 A1 | 11/2012 | Hagendorg et al. |
| 2012/0316108 A1 | 12/2012 | Chen et al. |
| 2013/0005649 A1 | 1/2013 | Niemoeller et al. |
| 2013/0012433 A1 | 1/2013 | Rosskamp et al. |
| 2013/0023467 A1 | 1/2013 | Silvestre et al. |
| 2013/0040878 A1 | 2/2013 | Silvestre |
| 2013/0065828 A1 | 3/2013 | Ruus et al. |
| 2013/0079279 A1 | 3/2013 | Becker et al. |
| 2013/0085102 A1 | 4/2013 | Silvestre |
| 2013/0096059 A1 | 4/2013 | Stechl et al. |
| 2013/0096060 A1 | 4/2013 | Stechl et al. |
| 2013/0203666 A1 | 8/2013 | Niemoeller et al. |
| 2013/0284912 A1 | 10/2013 | Vogel et al. |
| 2013/0296236 A1 | 11/2013 | Silvestre |
| 2014/0148384 A1 | 5/2014 | Boka et al. |
| 2014/0206611 A1 | 7/2014 | Becker et al. |
| 2014/0248365 A1 | 9/2014 | Rademacher et al. |

FOREIGN PATENT DOCUMENTS

| | | |
|---|---|---|
| CA | 1 173 388 | 8/1984 |
| CA | 1 341 203 | 11/1986 |
| CA | 1 258 427 | 8/1989 |
| CA | 1 336 329 | 7/1995 |
| CN | 1276731 | 12/2000 |
| CN | 1413582 | 4/2003 |
| CN | 101366692 | 2/2009 |
| CN | 101444618 | 6/2009 |
| CN | 101454019 | 6/2009 |
| CN | 101670096 | 3/2010 |
| DE | 196 37 230 | 3/1998 |
| DE | 10 2008 003 566 | 7/2009 |
| DE | 10 2008 003 568 | 7/2009 |
| DE | 10 2008 053 048 | 4/2010 |
| EP | 0 018 609 | 4/1980 |
| EP | 0 046 979 | 8/1981 |
| EP | 0 132 769 | 2/1985 |
| EP | 0 140 084 | 5/1985 |
| EP | 0 166 529 | 1/1986 |
| EP | 0 194 864 | 3/1986 |
| EP | 0 200 383 | 11/1986 |
| EP | 0 211 299 | 2/1987 |
| EP | 0 214 826 | 3/1987 |
| EP | 0 224 885 | 6/1987 |
| EP | 0 227 938 | 7/1987 |
| EP | 0 229 956 | 7/1987 |
| EP | 0 229 998 | 7/1987 |
| EP | 0 254 516 | 1/1988 |
| EP | 0 305 760 | 3/1989 |
| EP | 0 368 187 | 5/1990 |
| EP | 0 383 472 | 8/1990 |
| EP | 0 419 504 | 1/1994 |
| EP | 0 600 372 | 6/1994 |
| EP | 0 668 282 | 8/1995 |
| EP | 0 668 292 | 8/1995 |
| EP | 0 678 522 | 10/1995 |
| EP | 0 837 072 | 4/1998 |
| EP | 0 845 265 | 6/1998 |
| EP | 0 885 961 | 12/1998 |
| EP | 1 076 066 | 2/2001 |
| EP | 1 172 114 | 1/2002 |
| EP | 1 222 207 | 7/2002 |
| EP | 1 523 993 | 4/2005 |
| EP | 2 112 161 | 10/2009 |
| EP | 2 324 853 A1 | 5/2011 |
| EP | 2 329 848 | 6/2011 |
| EP | 2 389 945 | 11/2011 |
| EP | 0 921 812 | 12/2011 |
| EP | 2 387 989 | 7/2014 |
| FR | 2 456 522 | 12/1980 |
| GB | 0 835 638 | 5/1960 |
| GB | 0 840 870 | 7/1960 |
| GB | 1 527 605 | 10/1978 |
| GB | 1 554 157 | 10/1979 |
| JP | 61-212598 | 9/1986 |
| JP | 63-99096 | 9/1988 |
| JP | 2-218696 | 8/1990 |
| JP | 3-504240 | 9/1991 |
| JP | 6-506444 | 7/1994 |
| JP | 2-264798 | 10/1998 |
| JP | 2001-521004 | 11/2001 |
| JP | 2002-516880 | 6/2002 |
| JP | 2006-137678 | 1/2006 |
| JP | 2006-515267 | 5/2006 |
| JP | 2007-204498 | 8/2007 |
| JP | 2009-091363 | 4/2009 |
| JP | 2012-255040 | 12/2012 |
| RU | 2386631 | 9/2008 |
| TW | 157005 | 5/1991 |
| TW | 562806 | 11/2003 |
| WO | WO 83/00288 | 2/1983 |
| WO | WO 88/06599 | 9/1988 |
| WO | WO 89/10937 | 11/1989 |
| WO | 0 375 437 | 6/1990 |
| WO | WO 90/07522 | 7/1990 |
| WO | WO 90/11299 | 10/1990 |
| WO | WO 91/03550 | 3/1991 |
| WO | WO 91/16929 | 11/1991 |
| WO | WO 92/00321 | 1/1992 |
| WO | WO 92/12999 | 8/1992 |
| WO | WO 93/18786 | 9/1993 |
| WO | WO 94/14461 | 7/1994 |
| WO | WO 95/00550 | 1/1995 |
| WO | WO 95/24183 | 9/1995 |
| WO | WO 96/04307 | 2/1996 |
| WO | WO 96/07399 | 3/1996 |
| WO | WO 96/11705 | 4/1996 |
| WO | WO 96/32414 | 10/1996 |
| WO | WO 96/34882 | 11/1996 |
| WO | WO 96/41606 | 12/1996 |
| WO | WO 97/01331 | 1/1997 |
| WO | WO 97/48413 | 12/1997 |
| WO | WO 98/05351 | 2/1998 |
| WO | WO 98/08531 | 3/1998 |
| WO | WO 98/08871 | 3/1998 |
| WO | WO 98/08873 | 3/1998 |
| WO | WO 98/19698 | 5/1998 |
| WO | WO 98/30231 | 7/1998 |
| WO | WO 98/35033 | 8/1998 |
| WO | WO 98/39022 | 9/1998 |
| WO | WO 98/42749 | 10/1998 |
| WO | WO 98/56406 | 12/1998 |
| WO | WO 98/56418 | 12/1998 |
| WO | WO 98/07404 | 2/1999 |
| WO | WO 99/21573 | 5/1999 |
| WO | WO 99/21578 | 5/1999 |
| WO | WO 99/24071 | 5/1999 |
| WO | WO 99/25727 | 5/1999 |
| WO | WO 99/25728 | 5/1999 |
| WO | WO 99/40788 | 8/1999 |
| WO | WO 99/43708 | 9/1999 |
| WO | WO 99/46283 | 9/1999 |
| WO | WO 99/62558 | 12/1999 |
| WO | WO 00/23098 | 4/2000 |
| WO | WO 00/23099 | 4/2000 |
| WO | WO 00/29013 | 5/2000 |

(56) References Cited

FOREIGN PATENT DOCUMENTS

| | | |
|---|---|---|
| WO | WO 00/41546 | 7/2000 |
| WO | WO 00/66629 | 11/2000 |
| WO | WO 00/74736 | 12/2000 |
| WO | WO 01/00223 | 1/2001 |
| WO | WO 01/02039 | 1/2001 |
| WO | WO0104156 | 1/2001 |
| WO | WO 01/12155 | 2/2001 |
| WO | WO 01/21154 | 3/2001 |
| WO | WO 01/25278 | 4/2001 |
| WO | WO 01/28555 | 4/2001 |
| WO | WO 01/37808 | 5/2001 |
| WO | WO 01/43762 | 6/2001 |
| WO | WO 01/51071 | 7/2001 |
| WO | WO 01/52937 | 7/2001 |
| WO | WO 02/00243 | 1/2002 |
| WO | WO 02/24214 | 3/2002 |
| WO | WO 02/064115 | 8/2002 |
| WO | WO 02/066628 | 8/2002 |
| WO | WO 02/068660 | 9/2002 |
| WO | WO 02/070722 | 9/2002 |
| WO | WO 02/076495 | 10/2002 |
| WO | WO 02/079250 | 10/2002 |
| WO | WO 03/002021 | 1/2003 |
| WO | WO 03/020201 | 3/2003 |
| WO | WO 03/035028 | 5/2003 |
| WO | WO 03/035051 | 5/2003 |
| WO | WO 03/044210 | 5/2003 |
| WO | WO 03/053339 | 7/2003 |
| WO | WO 03/066084 | 8/2003 |
| WO | WO 03/094951 | 11/2003 |
| WO | WO 03/094956 | 11/2003 |
| WO | WO 03/101395 | 12/2003 |
| WO | WO 03/105888 | 12/2003 |
| WO | WO 2004/005342 | 1/2004 |
| WO | WO 2004/035623 | 4/2004 |
| WO | WO 2004/045592 | 6/2004 |
| WO | WO 2004/064862 | 8/2004 |
| WO | WO 2004/078196 | 9/2004 |
| WO | WO 2004/078197 | 9/2004 |
| WO | WO 2004/078198 | 9/2004 |
| WO | WO 2004/080480 | 9/2004 |
| WO | WO 2004/096854 | 11/2004 |
| WO | WO 2004/105781 | 12/2004 |
| WO | WO 2004/107979 | 12/2004 |
| WO | WO 2005/021022 | 3/2005 |
| WO | WO 2005/023291 | 3/2005 |
| WO | WO 2005/028516 | 3/2005 |
| WO | WO 2005/046716 | 5/2005 |
| WO | WO 2005/048950 | 6/2005 |
| WO | WO 2005/112949 | 12/2005 |
| WO | WO 2005/117948 | 12/2005 |
| WO | WO 2006/000567 | 1/2006 |
| WO | WO 2006/015879 | 2/2006 |
| WO | WO 2006/029634 | 3/2006 |
| WO | WO 2006/051103 | 5/2006 |
| WO | WO 2006/051110 | 5/2006 |
| WO | WO 2006/058620 | 6/2006 |
| WO | WO 2006/110551 | 10/2006 |
| WO | WO 2007/001150 | 1/2007 |
| WO | WO 2007/006307 | 1/2007 |
| WO | WO 2007/024700 | 3/2007 |
| WO | WO 2007/028394 | 3/2007 |
| WO | WO 2007/031187 | 3/2007 |
| WO | WO 2007/035665 | 3/2007 |
| WO | WO 2007/036299 | 4/2007 |
| WO | WO 2007/037607 | 4/2007 |
| WO | WO 2007/044867 | 4/2007 |
| WO | WO 2007/050656 | 5/2007 |
| WO | WO 2007/075534 | 7/2007 |
| WO | WO 2007/081824 | 7/2007 |
| WO | WO 2007/082381 | 7/2007 |
| WO | WO 2007/095288 | 8/2007 |
| WO | WO 2007/104786 | 9/2007 |
| WO | WO 2007/109221 | 9/2007 |
| WO | WO 2007/113205 | 10/2007 |
| WO | WO 2007/120899 | 10/2007 |
| WO | WO 2008/006496 | 1/2008 |
| WO | WO 2008/013938 | 1/2008 |
| WO | WO 2008/023050 | 2/2008 |
| WO | WO 2008/028914 | 3/2008 |
| WO | WO 2008/034881 | 3/2008 |
| WO | WO 02/065985 | 8/2008 |
| WO | WO 2008/124522 | 10/2008 |
| WO | WO 2008/133908 | 11/2008 |
| WO | WO 2008/145323 | 12/2008 |
| WO | WO 2009/004627 | 1/2009 |
| WO | WO 2009/030498 | 3/2009 |
| WO | WO 2009/030499 | 3/2009 |
| WO | WO 2009/039963 | 4/2009 |
| WO | WO 2009/048959 | 4/2009 |
| WO | WO 2009/056569 | 5/2009 |
| WO | WO 2009/063072 | 5/2009 |
| WO | WO 2009/087081 | 7/2009 |
| WO | WO 2009/087082 | 7/2009 |
| WO | WO 2009/089181 | 7/2009 |
| WO | WO 2009/098318 | 8/2009 |
| WO | WO 2009/102467 | 8/2009 |
| WO | WO 2009/134380 | 11/2009 |
| WO | WO 2010/030670 | 3/2010 |
| WO | WO 2010/043566 | 4/2010 |
| WO | WO 2010/044867 | 4/2010 |
| WO | WO 2010/092163 | 8/2010 |
| WO | WO 2011/017554 | 2/2011 |
| WO | WO 2011/012719 | 3/2011 |
| WO | WO 2011/029892 | 3/2011 |
| WO | WO 2011/058082 | 5/2011 |
| WO | WO 2011/058083 | 5/2011 |
| WO | WO 2011/103575 | 8/2011 |
| WO | WO 2011/122921 | 10/2011 |
| WO | WO 2011/128374 | 10/2011 |
| WO | WO 2011/144673 | 11/2011 |
| WO | WO 2011/144674 | 11/2011 |
| WO | WO 01/93837 | 12/2011 |
| WO | WO 2011/147980 | 12/2011 |
| WO | WO 2011/157402 | 12/2011 |
| WO | WO 2011/160066 | 12/2011 |
| WO | WO 2012/012352 | 1/2012 |
| WO | WO 2012/028172 | 3/2012 |
| WO | WO 2012/055967 | 5/2012 |
| WO | WO 2012/065996 | 5/2012 |
| WO | WO 2012/066086 | 5/2012 |
| WO | WO 2012/080320 | 6/2012 |
| WO | WO 2012/104342 | 8/2012 |
| WO | WO 2012/125569 | 9/2012 |
| WO | WO 2012/156296 | 11/2012 |
| WO | WO 2012/156299 | 11/2012 |
| WO | WO 2012/177929 | 12/2012 |
| WO | WO 2013/060850 | 5/2013 |
| WO | WO 2014/014849 | 1/2014 |
| WO | WO 2014/118355 | 8/2014 |

OTHER PUBLICATIONS

Larsen et al, Combination of the insulin sensitizer, pioglitazone, and the long-acting GLP-1 human analog, liraglutide, exerts potent synergistic glucose-lowering efficacy in severely diabetic ZDF rats, Diabetes, Obesity and Metabolism, 2008, 10, pp. 301-311.*

Croom et al, Liraglutide A Review of its Use in Type 2 Diabetes Mellitus, Drugs, 2009, 69, pp. 1985-2004.*

Cvetkovic et al, Exenatide A Review of Its Use in Patients with Type 2 Diabetes Mellitus (as an Adjunct to Metformin and/or a Sulfonylurea), Drugs, 2007, 67, pp. 935-954.*

U.S. National Institutes of Health: "GLP-1 Agonist AVE0010 in Patients With Type 2 Diabetes for Glycemic Control and Safety Evaluation, on Top of Pioglitazone 9GETGOAL-P)" XP002667584, (Jun. 27, 2011) Retrieved from the Internet: URL: http://clinicaltrials.gov/ct2/show/NCT00763815?term=lixisenatide+pioglitazone &rank=1 on Jan. 1, 2012.

Chancel, P. "Natixis Conference on Diabetes." Sanofi, (Nov. 8, 2011), Retrieved from the Internet: URL:http://en/sanofi.com/Images/29120_2011-11-08_Natixis_Chancel.pdf on Jan. 20, 2012.

Zinman, B. et al., "Efficacy and safety of the human glucagon-like peptide-1 analog liraglutide in combination with metformin and

(56) References Cited

OTHER PUBLICATIONS thiazolidinedione in patients with type 2 diabetes (LEAD-4 Met+TZD)." Diabetes Care, (Jul. 2009), vol. 32, No. 7, pp. 1224-1230.
"Positive Results for Investigational Compound Lyxumia(Lixisenatide)", American Diabetes Associations 71st Annual Scientific Sessions, Jun. 24, 2011, pp. 1-5, XP002667607, Retrieved from the Internet: URL:http://en.sanofi.com/Images/28303_20110626_LIXISENATIDE_ADA_en.pdf on Jan. 20, 2012.
International Preliminary Report on Patentability dated Oct. 21, 2013 issued in PCT/EP2012/066617.
International Search Report for PCT/EP2012/066617, dated Nov. 22, 2012, pp. 1-5.
Written Opinion of the International Search Authority for PCT/EP2012/066617, dated Nov. 22, 2012, pp. 1-6.
Shamoon, et al., The effect of intensive treatment of diabetes on the development and progression of long-term complications in insulin-dependent diabetes mellitus. The Diabetes Control and Complications Trial Research Group (1993) N. Engl. J. Med. 329, 977-986.
Dormandy et al., Secondary prevention of macrovascular events in patients with type 2 diabetes in the PROactive Study (PROspective pioglitAzone Clinical Trial in macroVascular Events): a randomised controlled trial. Lancet 2005, 366:1279-89.
Yki-Jarvinen, Thiazolidinediones, N Engl J Med 2004,351: 1106-18.
The extended European Search Report for EP Application No. 11 179 149.7, issued Feb. 9, 2012, pp. 1-7.
EMA Press release, European Medicines Agency recommends suspension of Avandia, Avandamet and Avaglim, (Sep. 23, 2010) pp. 1-2.
Craig et al., "ISPAD Clinical Practice Consensus Guidelines 2014 Compendium—Definition, epidemiology, and classification of diabetes in children and adolescents." Pediatric Diabetes, 15(Suppl. 20):4-17 (2014).
Pinget et al., "Efficacy and Safety of Lixisenatide Once Daily Versus Placebo in Patients With Type 2 Diabetes Insufficiently Controlled on Pioglitazone (GetGoal-P)." Diabetes, vol. 61(Supp 1):A258, Poster 1010-P (Jun. 2012).
International Diabetes Federation, 2011; Global IDF/ISPAD Guideline for Diabetes in Childhood and Adolescence, 2011 pp. 1-132.
Clinical Trials NCT00299871; accessed form https://clinicaltrials.gov/ct2/show/record/NCT00299871?term=NCT00299871&rank=1 accessed on Mar. 19, 2015; pp. 1-3.
Search Report from Chinese Patent Application No. 201280053404.6, dated Feb. 10, 2015, pp. 1-3.
EFC6017; Clinical Trial Eudra CT No. 2007-005884-92, accessed Apr. 24, 2015, one page.
NHSC—National Horizon Scanning Center, "AVE0010 (ZP10) for type 2 diabetes mellitus" University of Birmingham, England; pp. 1-6 (Dec. 2008).
Search Report of the Intellectual Property Office of Singapore for Patent Application No. 10201500871T, dated Nov. 2, 2015, pp. 1-3.
http://diabetes.emedtv.com/lantus/generic-lantus.html; last accessed Dec. 23, 2015; 1 pg.
18th World Health Congress (Helsinki). WMA Declaration of Helsinki—Ethical Principles for Medical Research Involving Human Subjects; WMA; Jun. 1964, pp. 1-8.
Abbas et al., "Impairment of synaptic plasticity and memory formation in GLP-1 receptor KO mice: Interaction between type 2 diabetes and Alzheimer's disease," Behav. Brain Res. 205:265-271 (2009).
Action to Control Cardiovascular Risk in Diabetes Study Group, "Effects of intensive glucose lowering in type 2 diabetes." N Engl J. Med. 358(24):2545-59 (2008).
Aderinwale et al., "Current therapies and new strategies for the management of Alzheimer's disease," Am J Alzheimers Dis Other Demen., 25(5):414-24 (2010).
Agholme et al., "An In Vitro Model for Neuroscience: Differentiation of SH-SY5Y Cells into Cells with Morphological and Biochemical Characteristics of Mature Neurons" J Alzheimers Disease, 20:1069-82 (2010).

American Diabetes Association (ADA) Committee Report—The Expert Committee On The Diagnosis And Classification Of Diabetes Mellitus—Report of the Expert Committee on the Diagnosis and Classification of Diabetes Mellitus, Diabetes Care, 21(Supplement 1): S5-S19 (Jan. 1998).
Akbar, "Sub-Optimal postprandial blood glucose level in diabetics attending the outpatient clinic of a University Hospital" Saudi Med Journal, 24(10):1109-1112 (Oct. 2003).
Ahren et al., Abstract "Efficacy and Safety of Lixisenatide QD Morning and Evening Injections vs Placebo in T2DM Inadequately Controlled on Metformin (GetGoal-M)" Oral presentation O-0591 presented at the World Diabetes Congress in Dubai, Dec. 5-8, 2011, one page.
Aoki et al., Hydrolysis of Nonionic Surfactants, Ann. Rept. Takeda Res. Lab. 27, 172-176 (1968).
Arnolds et al., "Further improvement in postprandial glucose control with addition of exenatide or sitagliptin to combination therapy with insulin glargine and metformin—a proof-of-concept study" Diabetes Care 33(7):1509-15 (2010).
Arnolds et al., "Insulin Glargine (GLAR) plus Metformin (MET): An Efficacious and Safe Regimen that can be combined with Exenatide (EXE) or Sitagliptin (SITA)" Diabetes, 58(Suppl. 1): A141, Jun. 2009.
Arnolds & Rave, "Basal insulin glargine vs prandial insulin lispro in type 2 diabetes," Lancet 378(9636):370-71 (2008).
Auerbach et al., "Angiogenesis assays: Problems and Pitfalls," Cancer and Metastasis Reviews, 19:167-72 (2000).
Bakaysa et al., "Physicochemical basis for the rapid time-action of $Lys^{B28}$ and $Pro^{B29}$-insulin: Dissociation of a protein-ligand complex," Protein Science 5:2521-31 (1996).
Banks et al., "Brain Uptake of the Glucagon-Like Peptide-1 Antagonist Exendin(9-39) after Intranasal Administration" Journal of Pharmacology and Experimental Therapeutics, 309:469-75 (2004).
Barnett & Owens, "Insulin Analogues," Lancet 349(9044):47-51 (1997).
Barnett et al., "Tolerability and efficacy of exenatide and titrated insulin glargine in adult patients with type 2 diabetes previously uncontrolled with metformin or a sulfonylurea: a multinational, randomized, open-label, two-period, crossover noninferiority trial." Clinical Therapeutics 29(11):2333-48 (Nov. 2007).
Barnett "Lixisenatide: evidence for its potential use in the treatment of type 2 diabetes." Core Evidence 6:67-79 (published online Sep. 8, 2011).
Barnett, "Insulin glargine in the treatment of type 1 and type 2 diabetes" Vascular Health and Risk Management 2:59-67 (published Jan. 25, 2006).
Barnett, "Dosing of Insulin Glargine in the Treatmetnt of Type 2 Diabetes," Clinical Ther. 29(6):987-99 (Jun. 2007).
Behar et al.. "Functional gallbladder and sphincter of oddi disorders." Gastroenterology 130(5):1498-1509 (2006).
Beintema & Campagne, "Molecular Evolution of Rodent Insulins," Mol. Biol. Evol. 4(1): 10-18, 1987.
Berger "Towards more physiological insulin therapy in the 1990s--A comment," Diabetes Research and Clinical Practice, 6(4): S25-31 (May 1989).
Berlie et al., "Glucagon-like peptide-1 receptor agonists as add-on therapy to basal insulin in patients with type 2 diabetes: a systematic review." Diabetes, Metabolic Syndrome and Obesity: Targets and Therapy 5:165-74 (2012).
Bertram et al., "The Genetics of Alzheimer Disease: Back to the Future," Neuron, 68:270-81 (2010).
Bethel & Feinglos, "Basal insulin therapy in type 2 diabetes." J Am Board Fam Pract. 18(3):199-204 (May-Jun. 2005).
Bhatt et al., "Chemical pathways of peptide degradation. I. Deamidation of adrenocorticotropic hormone," Pharm Res. 7(6):593-9 (1990).
Bland and Altman, "Measurement error" BMJ 312:1654 (Jun. 29, 1996).
Best, Mathmatics and Statistics pp. 1-39, 1988.
Blanchard et al., "Time sequence of maturation of dystrophic neurites associate with Aβ deposits in APP/PS1 transgenic mice" Experimental Neurology, 184:247-63 (2003).

(56) References Cited

OTHER PUBLICATIONS

Bolen et al., "Systematic Review: Comparative Effectiveness and Safety of Oral Medications for Type 2 Diabetes Mellitus," Ann. Intern. Med. 147:386-399 (Epub Jul. 16, 2007).
Bolli et al., "Efficacy and safety of lixisenatide once-daily versus placebo in patients with type 2 diabetes mellitus insufficiently controlled on metformin (GetGoal-F1)." Presentation Abstract No. 784, EASD Meeting Sep. 12-16, 2014.
Bolli et al., "Efficacy and safety of lixisenatide once daily vs. placebo in people with Type 2 diabetes insufficiently controlled on metformin (GetGoal-F1)." Diabetic Medicine 31:176-184 (published online Oct. 24, 2013).
Bolli "The pharmacokinetic basis of insulin therapy in diabetes mellitus," Diabetes Research and Clinical Practice, 6(4):S3-15 (May 1989).
Boutajangout et al., "Characterisation of cytoskeletal abnormalities in mice transgenic for wild-type human tau and familial Alzheimer's disease mutants of APP and presenilin-1" Neurobiology of Disease, 15:47-60 (2004).
Boutajangout et al., "Increased tau phosphorylation but absence of formation of neurofibrillary tangles in mice double transgenic for human tau and Alzheimer mutant (M146L) presenilin-1" 318(1):29-33 (2003).
Brange, "Design of Insulin Analogues for Meal-Related Therapy", J. Diabetes Complications 7(2):106-112 (Apr.-Jun. 1993). Abstract only.
Brange et al., "Toward Understanding Insulin Fibrillation," Journal of Pharmaceutical Sciences, 86(5):517-25 (1997).
Brange & Langkjeer, "Chemical stability of insulin 3. Influence of excipients, formulation, and pH," Acta Pharma. Nord. 4(3):149-58 (1992).
Brange et al., "Monomeric insulins and their experimental and clinical implications," Diabetes Care 13(9):923-45 (Sep. 1990).
Brange et al., "Neutral insulin solutions physically stabilized by addition of Zn2+," Diabetic Medicine 3:532-6 (Nov.-Dec. 1986).
Brange "Galenics of Insulin" 1987, p. 35-36.
Brange & Langkjaer, "Insulin Structure and Stability" Chapter 11; Pharm Biotechnol 5:315-50 (1993).
Brod et al., "Adherence patterns in patients with type 2 diabetes on basal insulin analogues: missed, mistimed and reduced doses." Curr Med Res Opin. 28(12):1933-46 (2012).
Brod et al., "Examining correlates of treatment satisfaction for injectable insulin in type 2 diabetes: lessons learned from a clinical trial comparing biphasic and basal analogues." Health Quality of Life Outcomes. 5:8 (2007), pp. 1-10.
Broderick et al., "Guidelines for the Management of Spontaneous Intracerebral Hemorrhage in Adults," Circulation 116:e391-e413 (2007).
Brown & Nichols, "Slow response to loss of glycemic control in type 2 diabetes mellitus."Am J Manag Care. 9(3):213-17 (2003).
"Buffer" Oxford Dictionary of Biochemistry and Molecular Biology, Oxford University Press, 2001, p. 83.
Burgermeister et al. "The Isolation of Insuin from the Pancreas," Insulin, Part 2, 1975, p. 715-727.
Pederson et al., "Improved Glucose Tolerance in Zucker Fatty Rats by Oral Administration of the Dipeptidyl Peptidase IV Inhibitor Isoleucine Thiazolidide." Diabetes 47(8):1253-58 (1998).
Perfetti "Combining basal insulin analogs with glucagon-like peptide-1 mimetics." Diabetes Technology & Therapeutics 13(9):873-81 (2011).
Perry et al., "A novel neurotrophic property of glucagon-like peptide 1: a promoter of nerve cell growth factor mediated differentiation on PC12 cells" J Pharmacol Exp (2002) pp. 958-966, vol. 300.
Perry et al., "Protection and reversal of excitotoxic neuronal damage by glucagon-like peptide-1 and exendin-4" J Pharmacol Exp Ther (2002) pp. 881-888, vol. 302.
Perry et al., "Evidence of GLP-1-mediated neuroprotection in an animal model of pyridoxine-induced peripheral sensory neuropathy" Exp Neural (2007) pp. 293-301, vol. 203, No. 2.
Perry et al., "The glucagon-like peptides: a double-edged therapeutic sword" Trends in Pharmacological Sciences (2003) pp. 377-383, vol. 24.
Perry et al., "A new Alzheimer's disease interventive strategy: GLP-1." Current Drug Targets; 5(6):565-71 (Aug 2004).
Pillion et al., "Dodecylmaltoside-mediated Nasal and Ocular Absorption of Lyspro-Insulin: Independence of Surfactant from Multimer Dissociation," Pharmaceutical Research, 15(10): 1637-39 (Oct. 1998).
Pi-Sunyer et al., "The effects of pharmacologic agents for type 2 diabetes mellitus on body weight". Postgrad Med. 120(2):5-17 (Jul. 2008).
Pohl & Wank, "Molecular Cloning of the Fleloderman and Exendin-4 cDNAs in the Lizard," J. Biol. Chem. 273(16):9778-84 (1998).
Porter et al., "Four weeks administration of Liraglutide improves memory and learning as well as glycemic control in nice with high fat dietary-induced obesity and insulin resistance" Diab Obes Metab (2010) pp. 891-899.
Pradier L et al. "Animal Models of Alzheimer's disease." Demences (Dementias); eds. Duyckaerts C. and Pasquier F.; publisher Doin; 165-170 (Sep. 10, 2002; available Aug. 27, 2002).
Prandini "Methods of measuring gallbladder motor functions-the need for standardization: scintigraphy." Dig Liver Dis. 35 Suppl 3:S62-6 (2003).
"Preferable." Merriam-Webster.com. Merriam-Webster, n.d. Web. Sep. 7, 2015. http://www.merriamwebster.com/dictionary/preferable).
Pugeat et al., "Insulin Resistance, Polycystic Ovary Syndrome and Metformin" Review Article, Drugs 1999; 58(Suppl 1):41-46 (Sep. 1999).
Quianzon & Shomali, "Lixisentide-Once Daily Glucagon-like Peptide-1 receptor Agonist in the Management of Type 2 Diabetes", US Endocrinology, 7(2):104-9 (Winter 2011).
Raccah et al., "When Basal Insulin Therapy in Type 2 Diabetes Mellitus is Not Enough—What Next?" Diabetes Vletabolism Research and Reviews 23:257-64 (published online Feb. 21, 2007).
Ramos et al., "Early neuropathology of somatostatin/NPY GABAergic cells in the hippocampus of a PS1xAPP transgenic model of Alzheimer's disease" Neurobiology of Aging, 27:1658-1672 (2006).
Rao et al., "Is the combination of sulfonylureas and metformin associated with an increased risk of cardiovascular disease or all-cause mortality? A meta-analysis of observational studies." Diabetes Care. 31(8):1672-8 (2008).
Raju et al., "Optimum Palliation of Inoperable Hilar Cholangiocarcinoma: Comparative Assessment of the Efficacy of Plastic and Self-Expanding Metal Stents," Dig Dis Sci. 56:1557-64 (published online, Jan. 11, 2011).
Ratner et al. Abstract 131 "Post-meal pharmacodynamics profile of AVE0010, a once-daily GLP-1 receptor agonist, in patiens with type 2 diabetes inadequately controlled on metformin" Diabetologia 52(Suppl. 1): S60, #131 (Sep. 2009).
Ratner et al. "Dose-dependent effects of the once-daily GLP-1 receptor agonist lixisenatide in patients with Type 2 diabetes inadequately controlled with metformin: a randomized double-blind, placebo-controlled trial," Diabetic Med. 27(9):1024-1032 (Sep. 2010).
Ratner et al., Poster "A dose-finding study of the new GLP-1 agonist AVE0010 in Type 2 Diabetes insufficiently controlled with metformin.", Diabetes, 57:Suppl.1, A129, Abstract No. 433-P, 68th Annual Meeting of the American Diabetes Association, San Francisco, Jun. 6-10, 2008.
Raufman "Bioactive peptides from lizard venoms," Regul Pept 61(1):1-18 (1996).
Request for "Type C" Meeting letter sent by Michael Lutz addressed to Mary Parks, dated Apr. 21, 2006, pp. 1-10.
Richter, von Margret, "Oldtimer as Newcomer" Pharmazie, pp. 1-9; http://www.pharmazeutische-zeitung.de/pza/2002-12/pharm1.htm (Feb. 2002).
Riddle et al., Contributions of Basal and Postprandial Hyperglycemia Over a Wide Range of A 1 C Levels Before and After Treatment Intensification in Type 2 Diabetes, Diabetes Care 34:2508-2514 (published online Oct. 25, 2011).

(56) References Cited

OTHER PUBLICATIONS

Riddle et al., Adding once-daily Lixisenatide for Type 2 Diabetes inadequately controlled by established basal insulin: a 24-week, randomized, placebo-controlled comparison (GetGoal-L). Diabetes Care 36(9):2489-96 (Sep. 2013).
Riddle et al., "Adding Once-Daily Lixisenatide for Type 2 Diabetes Inadequately Controlled with Newly Initiated and Continuously Titrated Basal Insulin Glargine" Diabetes Care, pp. 2497-2503 (Sep. 2013).
Ritzel et al., "A Synthetic Glucagon-Like Peptide-1 Analog with Improved Plasma Stability," J. Endocrine. 159(1):93-102 (1998).
Rohrmann, "Differential Diagnosis of Pancreatic and Biliary Duct Diseases," Diseases of the Abdomen and Pelvis Syllabus, pp. 170-174 (1999).
Rosenstock et al., Poster "Efficacy and safety of lixisenatide once daily vs exenatiide twice daily in type 2 DM inadequately controlled on metformin (GetGoal-X)." 71st Scientific Sessions (Nov. 2011).
Rosenstock et al., OP 25 GLP-1 Based therapies, Abstract 145 "Dose range effects of the new once daily GLP-1 receptor agonist AVE0010 added to metformin in type 2 diabetes," Diabetologia 51 (Supplement 1):S66 (Sep. 2008).
Rosenstock et al., Abstract, 564P "Post-meal effects of AVE0010, a once-daily GLP-1 receptor agonist, in type 2 diabetes inadequately controlled on metformin," Diabetes 58(Suppl.1):A151-A152 (Jun. 1, 2009).
Rubino et al., "Delayed initiation of subcutaneous insulin therapy after failure of oral glucose-lowering agents in patients with type 2 diabetes: a population-based analysis in the UK." Diabet Med. 24(12):1412-18 (2007).
Sampson et al., "Second symposium on the definition and management of anaphylaxis: summary report—Second National Institute of Allergy and Infectious Disease/Food Allergy and Anaphylaxis Network symposium." Journal of Allergy and Clinical Immunology, 117(2):391-397 (2006).
Sanger et al., "The amide groups of insulin," Biochem J. 59(3):509-18 (1955).
Sanofi's Lantus Draft Prescribing Information/Package Insert: "NDA 21-081 DRAFT package insert" (Sponsor revision #5) Date of submission: Apr. 20, 2000; see http://www.drugbank.ca/system/fds_labels/DB00047.pdf 1265922812; pp. 1-14.
Sanofi Press Release; "Lyxumia (lixisenatide) in Combination with Basal insulin plus Oral Anti-Diabetics Significantly Reduced HbA1c and Post-Prandial Glucose"; Paris, France (Jun. 9, 2012) pp. 1-6.
Sanofi-aventis Press Release, "Once Daily Lixisenatide (AVE 0010) Given as Monotherapy Successfully Meets Phase III Study Endpoints in Diabetes" Paris, France (Apr. 15, 2010) pp. 1-2.
Sanofi Press Release (Peron and Schaeffer), "Sanofi GetGoal Program on Lyxumia®, as an Add-on to Basal Insulin, Shows Significant Positive Phase III Results," Paris, France (May 31, 2011) pp. 1-2.
Sanofi Press release (Peron and Schaeffer); "Sanofi Reports Positive Results for Once-daily Lyxumia® (lixisenatide) in Combination with Lantus® (insulin glargine) in Type 2 Diabetes" Paris, France (Dec. 6, 2011) pp. 1-3.
Sanofi-aventis Press Release (Gabriel), "New Diabetes Compound AVE0010 Showed Clear Dose Response Results With Once-A-Day Injection in Phase IIb Study" Paris, France (Jun. 7, 2008) pp. 1-2.
Sanofi-aventis Press Release (Peron and Schaeffer), "Sanofi-aventis Announces Positive Top-line Lixisentatide Phase III Results" Paris, France (Feb. 2, 2011) pp. 1-2.
Sanofi Press Release (Peron and Schaeffer), "Lyxumia® (lixisenatide) One-Step Regimen as Effective as Two-Step Regimen in Improving Glycemic Control in Type 2 Diabetes" Paris, France (Sep. 12, 2011) pp. 1-3.
Sanofi Press Release (Sigurd), "Lixisenatide Significantly Reduces HbA1c Without Increasing Hypoglycemia in Patients Uncontrolled on Sulfonylureas", Pressmeddelande (Apr. 12, 2011) pp. 1-2.
Sanofi and Zealand Pharma Press Release (Evaluate), "Additional Positive Results from Global Phase III Program With Lixisenatide for Type 2 Diabetes", (Apr. 12, 2011) pp. 1-3.
Sanofi Press Release entitled "FDA Accepts Sanofi's New Drug Application for Basal Insulin Toujeo®," dated Jul. 8, 2014, pp. 1-2.
Sanofi Press Release entitled "Sanofi Receives FDA Approval of Once-Daily Basal Insulin Toujeo®," dated Feb. 26, 2015, pp. 1-4.
Zealand Pharma Press Release entitled "Sanofi-Aventis finalize phase lia clinical study with GLP-1 agonist for type 2 diabetes licensed from Zealand Pharma" dated Mar. 3, 2005, one page.
Weiss et al., "Activities of Monomeric Insulin Analogs at Position A8 Are Uncorrelated With Their Thermodynamic Stabilities", The Journal of Biological Chemistry 276(43):40018-24 (2001).
Werner et al., "Pharmacological profile of lixisenatide: A new GLP-1 receptor agonist for the treatment of type 2 diabetes." Regulatory Peptides 164(2-3):58-64 (Epub Jun. 2, 2010).
Werner et al., "Insulin Glargine U-100 Has a Favourable Time-Action Profile Compared to U-40 or NPH Insulin in Healthy, Normoglycaemic Dogs", Poster-Abstract 37th Annual Meeting of Endocrine Society of India, Tirupati, A.P., India ESICON (2007) (2 pages including Abstract and Poster).
Weyer et al., "Long-term changes in insulin action and insulin secretion associated with gain, loss, regain and maintenance of body weight", Diabetologia, (43)1:36-46 (Jan. 2000).
White et al., "Randomized clinical trials with added rescue medication: some approaches to their analysis and interpretation." Statistics in Medicine 20:2995-3008 (2001).
Whittingham et al., "Insulin at PH2: Structural Analysis of the Conditions Promoting Insulin Fibre Formation" J. Mol. Biol., (2002), vol. 318, pp. 479-490.
WHO BMI classification, accessed at URL apps.who.int/bmi/index.jsp?introPage=itrol_3.html, Sep. 9, 2013, one page.
WHO Drug Information vol. 22(2), list 99, p. 142 (lixisenatide) (Jul. 2008).
WHO Rational Use of Medicines, http://www.who.int/medicines/areas/rational_use/en/downloaded Dec. 18, 2014 10:02:48AM (2012).
Widjaja et al., "UKPDS 20: plasma leptin, obesity, and plasma insulin in type 2 diabetic subjects." J Clin Endocrinol Metab. 82(2):654-7 (1997).
Wiernsperger, et al. "The Antihyperglycaemic Effect of Metformin Therapeutic and Cellular Mechanisms" Review Article, Drugs 1999:58(Suppl 1):31-39 (Sep. 1999).
Wirths et al., "Intraneuronal APP/Aβ Trafficking and Plaque Formation in β-Amyloid Precursor Protein and Presenilin-1 Transgenic Mice" Brain Pathol. 12:275-286 (2002).
Wirths et al., "Reelin in plaques of beta-amyloid precursor protein and presenilin-1 double-transgenic mice." Neurosci Lett. 316(3):145-48 (2001).
Wirths et al., "Intraneuronal Abeta accumulation precedes plaque formation in beta-amyloid precursor protein and presenilin-1 double-transgenic mice." Neurosci Lett. 306(1-2):116-20 (2001).
Wollen, Alzheimer's disease: the pros and cons of pharmaceutical, nutritional, botanical, and stimulatory therapies, with a discussion of treatment strategies from the perspective of patients and practitioners, Altern Med. Rev., 15:223-44 (2010).
Yoon et al., "Exenatide added to insulin therapy: a retrospective review of clinical practice over two years in an academic endocrinology outpatient setting." Clinical Therapeutics 31(7):1511-23 (2009).
Yu et al., "Effect of Zinc Sulphate and Zinc Methionine on Growth, Plasma Growth Hormone Concentration, Growth Hormone Receptor and Insulin-Like Growth Factor-1 Gene Expression in Mice", Clin Exp Pharmacal Physiol 32(4):273-78 (2005). Abstract only.
Ziemer et al., "Clinical inertia contributes to poor diabetes control in a primary care setting" The Diabetes Educ 31 (4):564-71 (2005).
Ziessman et al., "Sincalide-stimulated cholescintigraphy: a multicenter investigation to determine optimal infusion methodology and gallbladder ejection fraction normal values." J Nucl Med. 51(2):277-81 (Feb. 2010).
Zimmet' al. et al "Clinical Efficacy of Metformin against Insulin Resistance Parameters, Sinking the Iceberg" Review Article, Drugs 1999: 58(Suppl 1):21-28 (Sep. 1999).
Zinman "The Physiologic Replacement of Insulin," New England J. Med. 321(6):363-70 (Aug. 1989).

(56) References Cited

OTHER PUBLICATIONS

Translation of pp. 1109, 1116 and 1117 of "Clinical Effectiveness of Long-Term Administration of BAY g5421 (Acarbose) on Insulin-Treated Diabetes," Jpn. Pharmacal. Ther; 1996 vol. 24 No. 5: 1109-1129, pp. 1-4.
Translation of pp. 2346 and 2348 of Rinsho To Kenkyu, "Effectiveness of Combination Therapy Using Voglibose and Insulin in Patients with NIDDM," 1997, vol. 74, No. 9: 2346-2352, pp. 1-3.
Translation of pp. 121 and 124 of Igaku To Yakugaku, "Utility of Voglibose Long-term Combined Therapy in Non-Insulin Dependent Diabtetic Patients with Little Effective of Sulfonylureas," 1999, vol. 42, No. 1: 121-129, pp. 1-3.
Translation of pp. 750, 753 and 754 of Igaku No Ayumi, "Incretin Receptors," 2010, May, vol. 233; No. 9:750-754, pp. 1-4.
Non-Final Office Action issued in U.S. Appl. No. 13/123,835; mailed May 28, 2015, pp. 1-11.
Non-Final Office Action issued in U.S. Appl. No. 13/123,835; mailed Dec. 22, 2014, pp. 1-13.
Final Office Action issued in U.S. Appl. No. 13/123,835; mailed Feb. 12, 2013, pp. 1-13.
Non-Final Office Action issued in U.S. Appl. No. 13/123,835; mailed Jul. 19, 2012, pp. 1-14.
Non-Final Rejection issued in U.S. Appl. No. 13/382,442; mailed Feb. 5, 2015, pp. 1-31.
Final Rejection issued in U.S. Appl. No. 13/382,442; mailed Jun. 13, 2014, pp. 1-29.
Non-Final Rejection issued in U.S. Appl. No. 13/382,442; mailed Dec. 19, 2013, pp. 1-29.
Final Rejection issued in U.S. Appl. No. 13/382,442; mailed Jul. 17, 2013, pp. 1-30.
Non-Final Rejection issued in U.S. Appl. No. 13/382,442; mailed Nov. 7, 2012, pp. 1-26.
Non-Final Rejection issued in U.S. Appl. No. 13/382,772; mailed Sep. 14, 2015, pp. 1-42.
Final Rejection issued in U.S. Appl. No. 13/382,772; mailed Feb. 10, 2015, pp. 1-36.
Non-Final Rejection issued in U.S. Appl. No. 13/382,772; mailed Sep. 29, 2014, pp. 1-33.
Final Rejection issued in U.S. Appl. No. 13/382,772; mailed Jun. 3, 2014, pp. 1-34.
Non-Final Rejection issued in U.S. Appl. No. 13/382,772; mailed Nov. 21, 2013, pp. 1-42.
Non-Final Rejection issued in U.S. Appl. No. 13/382,772; mailed Apr. 10, 2013, pp. 1-48.
Final Rejection issued in U.S. Appl. No. 12/617,811; mailed Jul. 31, 2015, pp. 1-15.
Non-Final Rejection issued in U.S. Appl. No. 12/617,811; mailed Jan. 14, 2015, pp. 1-15.
Final Rejection issued in U.S. Appl. No. 12/617,811; mailed Jan. 4, 2013, pp. 1-6.
Non-Final Rejection issued in U.S. Appl. No. 12/617,811; mailed Jun. 21, 2012, pp. 1-7.
Non-Final Rejection issued in U.S. Appl. No. 12/617,811; mailed Oct. 27, 2011, pp. 1-13.
Non-Final Rejection issued in U.S. Appl. No. 12/617,811; mailed Apr. 27, 2011, pp. 1-10.
Non-Final Office Action from U.S. Appl. No. 12/617,805; mailed Sep. 15, 2015, pp. 1-12.
Final Office Action from U.S. Appl. No. 12/617,805; mailed Jan. 13, 2015, pp. 1-11.
Non-Final Office Action from U.S. Appl. No. 12/617,805; mailed Jul. 24, 2014, pp. 1-12.
Final Office Action from U.S. Appl. No. 12/617,805; mailed Feb. 11, 2013, pp. 1-13.
Correa, "Pautas para el examen de patentes farmaceuticas. Una perspectiva desde la Salud Publica. Documento de Trabajo" Universidad de Buenos Aires, Mar. 2008, pp. 1-66. See English on pp. 19-20.

Jekel et al., "Use of endoproteinase Lys-C from Lysobacter enzymogenes in protein sequence analysis," Anal Biochem. 134(2):347-54 (1983).
Kaarsholm et al., "Engineering stability of the insulin monomer fold with application to structure-activity relationships," Biochemistry 32(40):10773-8 (1993).
European Medicines Agency—Science Medicines Health, "Guideline on clinical investigation of medicinal products in the treatment of diabetes mellitus" Committee for Medicinal Products for Human Use, Jan. 20, 2010, pp. 1-19.
Seino et al., and The Committee of Japan Diabetes Society on the diagnostic criteria of diabetes mellitus. "Report of the committee on the classification and diagnostic criteria of diabetes mellitus." Journal of the Japan Diabetes Society. 53:450-467 (2010). In Japanese, English translation of selected passages provided.
Gough, K. et al.; Assessment of Dose Proportionality: Report from the Statisticians in the Pharmaceutical Industry/Pharmacokinetics UK Joint Working Party; Drug Information Journal, vol. 29, 1995, pp. 1039-1048.
Goykhman et al., "Insulin Glargine: a review 8 years after its introduction." Expert Opin. Pharmacother. 10(4):705-18 (2009).
Greig et al., "Once Daily Injection of Exendin-4 to Diabetic Mice Achieves Long-Term Beneficial Effects on Blood Glucose Concentrations." Diabetologia 42(1):45-50 (1999).
Gura, "Systems for Identifying New Drugs are Often Faulty," Science, 278(5340):1041-042 (1997).
Gutniak et al., "Antidiabetogenic Effect of Glucagon-Like Peptide-1 (7-36) Amide in Normal Subjects and Patients with Diabetes Mellitus," N. Engl. J. Med. 326:1316-1322 (1992).
Hamilton et al., "Novel GLP-1 mimetics developed to treat type 2 diabetes promote progenitor cell proliferation in the brain" J Neurosci Res (2011) pp. 481-489, vol. 89.
Hamilton et al., "Receptors for the incretin glucagon-like peptide-1 are expressed on neurons in the central nervous system" Neuroreport(2009) vol. 20 No. 13, pp. 1161-1166.
Hanas et al., "2010 Consensus Statement on the Worldwide Standardization of the Hemoglobin A1C Measurement." Diabetes Care 33(8):1903-04 (Aug. 2010).
Hanefeld & Temelkova-Kurktschiev, "The postprandial state and the risk of atherosclerosis." Diabet Med. 14 Suppl 3:S6-11 (1997).
Hanefeld M. Normnahe postprandiale Hyperglykamie-eine essenzielle Komponente guter Diabeteskontrolle und Pravention kardiovaskularer Erkrankungen (Near-normal postprandial hyperglycemia—an essential component of good diabetes control and prevention of cardiovascular diseases). Paul Langerhans lecture 2007. Diabetologie und Stoffwechsel 2007; 2:362-369. in German with English abstract, Abstract only.
Hanna et al., Canadian Diabetes Association Clinical Practice Guidelines Expert Committee "Pharmacologic Management of Type 2 Diabetes" Canadian Journal of Diabetes, 27(Supp 2):S37-S42 (Dec. 2003).
Harris "Clinical inertia in patients with T2DM requiring insulin in family practice." Can Fam Physician.56(12):e418-e424 (2010).
Harkavyi et al., "Glucagon-like peptide I receptor stimulation reverses key deficits in distinct rodent models of Parkinson's disease" J Neuroinffamm (2008) pp. 1-9, vol. 5, No. 19.
Hartmann et al., "Biological Activity of des-(B26-B30)-Insulinamide and Related Analogues in Rat Hepatocyte Cultures," Diabetologia 32(7):416-20 (1989).
Heinrich et al., "Pre-proglucagon messenger ribonucleic acid: nucleotide and encoded amino acid sequences of the rat pancreatic complementary deoxyribonucleic acid," Endocrinol. 115(6):2176-81 (1984).
Hellstrom et al., "T1388 GTP-010 As a Therapetuic Tool in IBS Pain Relief: Prospective, Randomized, Palebo-Controlled Study of a GLP-1 Analog", Gastroenterology, 134(4):A-544; Absract T1388 (Apr. 2008).
Higgins et al., "Oxidative Stress: Emerging Mitochondrial and Cellular Themes and Variations in Neuronal Injury", Journal of Alzheimer's Disease, 20:S453-S473 (2010).
Himeno et al., "Beneficial effects of exendin-4 on experimental polyneuropathy in diabetic mice" Diabetes (2011) pp. 2397-2406, vol. 60.

(56) References Cited

OTHER PUBLICATIONS

Hinds et al., "Synthesis and characterization of poly(ethylene glycol)-insulin conjugates." Bioconjugate Chem. 11 (2)195-201 (Mar.-Apr. 2000).
Hoe 901/2004 Study Investigators Group, "Safety and efficacy of insulin glargine (HOE 901) versus NPH insulin in combination with oral treatment in Type 2 diabetic patients," Diabetic Medicine (2003), vol. 20, pp. 545-551, XP002671079.
Holscher "Development of Beta-Amyloid-induced neurodegeneration in Alzheimer's disease and novel neuroprotective strategies," Reviews in Neuroscience, 16:181-212 (2005).
Holscher et al., "New roles for insulin-like hormones in neuronal signaling and protection: new hopes for novel treatments of Alzheimer's disease?" Neuro. Aging 31:1495-1502 (2008).
Holscher "The role of GLP-1 in neuronal activity and neurodegeneration" Vitamins and hormones 84:331-54 (2010).
Holscher "Incretin Analogues that have been Developed to Treat Type 2 Diabetes Hold Promise as a Novel Treatment Strategy for Alzheimer's Disease" Recent Patents On CNS Drug Discovery(2010) vol. 5 No. 2, pp. 109-117.
Holscher "Possible Causes of Alzheimer's Disease: Amyloid Fragments, Free Radical, and Calcium Homeostasis" Neurobiology of Disease 5:129-41 (1998).
Holst, "Glucagon-like Peptide-1, A Gastrointestinal Hormone with a Pharmaceutical Potential," Current Medicinal Chemistry 6:1005-17 (1999).
Holst & Vilsboll. "Combining GLP-1 receptor agonists with insulin: therapeutic rationales and clinical findings." Diabetes, Obesity and Metabolism 15(1):3-14 (2013).
Home et al., "Insulin treatment: a decade of change," British Medical Bulletin, 1989, vol. 45, No. 1, pp. 92-110.
Holman et al., "10-Year Follow-up of Intensive Glucose Control in Type 2 Diabetes." N Engl J. Med. 359(15):1577-89 (2008).
Hunter et al., "Drugs developed to treat diabetes. Liraglutide and lixisenatide, cross the blood brain barrier and enhance neurogenesis", BMC Neuroscience, (2012) vol. 13, p. 6.
Inpharma, Product News. "AVE0010 set to deliver in type 2 diabetes mellitus," Database Adisnews, retrieved from STN, Jun. 2008, pp. 1-3.
Insulinpraparat Wikipedia, http://de.wikipedia.org/wiki/Insulinpr%C3%A4parat, pp. 1-15 (Feb. 5, 2013).
"Insulin Aspart Injection." Formulated Preparations: Specific Monographs. British Pharmacopoeia 3. pp. 1-3 (2012).
Inzucchi et al. "Management of Hyperglycemia in Type 2 Diabetes: A Patient-Centered Approach" Diabetes Care, 35:1364-79 (Jun. 2012).
Isacson et al., "The glucagon-like peptide 1 receptor agonist exendin-4 improves reference memory performance and decreases immobility in the forced swim test" Eur J Pharmacal (2009) pp. 249-255, vol. 10, No. 650.
Jackson et al., "Neutral regular insulin," Diabetes 21(4):235-45 (1972).
Jain, "Barriers to Drug Delivery in Solid Tumors," Scientific American, 271(1):58-65 (Jul. 1994).
Jang et al., "Neuroprotective Effects of Triticum aestivum L. against β-Amyloid-induced Cell Death and Memory Impairments" Phytother. Res. 24:76-84 (2010).
Jendle et al., "Insulin and GLP-1 analog combinations in type 2 diabetes mellitus: a critical review." Expert Opin. Investig. Drugs 21(10):1463-74 (2012).
Jimenez et al., "Inflammatory Response in the Hippocampus of PS1M146L/APP751SL Mouse Model of Alzheimer's Disease: Age-Dependent Switch in the Microglial Phenotype from Alternative to Classic" Neurobiology of Disease, 28(45):11650-661 (2008).
Johnson et al., "When is a unit of insulin not a unit of insulin? Detemir dosing in type 2 diabetes" 2008. http://professional.diabetes.org/ContenUPosters/2008/p8-LB.pdf.

Jorgensen, K H., et al., "Five fold increase of insulin concentration delays the absorption of subcutaneously injected human insulin suspension in pigs", Diabetes Research and Clinical Practice, 50:161-167 (2000).
Kadima "Role of Metal Ions in the T- to R-Allosteric Transition in the Insulin Hexamer," Biochem. 38(41):13443-53 (Oct 1999).
Kaduszkiewicz et al.., "Cholinesterase inhibitors for patients with Alzheimer's disease: systematic review of randomised clinical trials." BMJ 331:321 (2005).
Kaech & Banker, "Culturing hippocampal neurons" Nat Protoc. 1(5):2406-15 (2006).
Kahn et al., "Glycemic durability of rosiglitazone, metformin, or glyburide monotherapy." N Engl J. Med. 355(23):2427-43 (2006).
Kakhi et al., "Normal values of gallbladder ejection fraction using 99 mTc-sestamibi scintigraphy after a fatty meal formula." J Gastrointestin Liver Dis. 16(2):157-61 (Jun. 2007).
Kamisawa. et al., "Pancreatographic investigation of pancreatic duct system and pancreaticobiliary malformation" J. Anal. 212(2):125-34 (2008).
Burke et al., "Nature of the B10 amino acid residue," Int. J. Peptide Protein Res., 23(4):394-401 (Apr. 1984).
Buse et al., "Use of twice-daily exenatide in Basal insulin-treated patients with type 2 diabetes: a randomized, controlled trial." Annals of Internal Medicine 154(2):103-12 (Jan. 2011).
Byetta—Summary of Product Characteristics, updated Jan. 27, 2015, last accessed Apr. 18, 2015, pp. 1-12.
Byrne et aL, "Inhibitory Effects of Hyperglycaemia on Fed Jejunal Motility: Potential Role of Hyperinsulinaemia," Euro. J. Clin. Invest. 28(1):72-78 (1998).
Cadario, "Sitagliptin" Drug Information Perspectives, 30(4):1-6 (2010).
Campbell et al., "Insulin Glargine," Clin. Therapeutics 23(12):1938-57 (2001).
Campas et al., "AVE-0010 GLP-1 Receptor Agonist Treatment of Diabetes", Drugs of the Future 33(10):838-40 (Oct. 2008).
Casas et al., "Massive CA1/2 Neuronal Loss with Intraneuronal and N-Terminal Truncated Aβ 42 Accumulation in a Novel Alzheimer Transgenic Model" American Journal of Pathology 165(4):1289-1300 (2004).
Chatterjee et al., "Insulin glargine and its place in the treatment of Types 1 and 2 diabetes mellitus." Expert Opin Pharmacother 7(10):1357-71 (2006).
Charles et al., "Prevention of Type 2 Diabetes Role of Metformin" Review Article, Drugs 1999; 58 Suppl. 1:71-73 (Sep. 1999).
Chen et al., "Tissue-specific Expression of Unique mRNAs That Encode Proglucagon-derived Peptides or Exendin 4 in the Lizard," J. Biol. Chem. 272(7):4108-15 (1997).
Cheung et al., "Effects of all-trans-retinoic acid on human SH-SY5Y neuroblastoma as in vitro model in neurotoxicity research" NeuroToxicology, 30:127-35 (2009).
Childs et al., "Defining and Reporting Hypoglycemia in Diabetes," Diabetes Care 28(5):1245-9 (May, 2005).
Cholangiocarcinoma, Johns Hopkins Medicine Webstite, https://gi.jhsps.org/GDL Disease.aspx?CurrentUDV=31&GDLCat_ID=AF793A59-B736-42CB-9E1FE79D2B9FC358&GDL_Disease_ID=A6D1OE80-887D-49A7-B3BB-0517D38CE757, accessed on May 14, 2014, pp. 1-12.
Christensen et al., "Lixisenatide for type 2 diabetes mellitus," Expert Opin. 20(4):549-57 (Epub Mar. 11, 2011).
Cochran et al., "The Use of U-500 in Patients with Extreme Insulin Resistance" Diabetes Care, 28(5):1240-44 (2005).
Community register of medicinal products for human use, Chemical Subgroup A10BX, "Lyxumia" European Commision—Public Heath, (May 2, 2013), p. 1.
Colclough et al., Abstract "Levels of FPG and HbA1c Control and the Relationship to BMI in T2D Patients Treated with Basal Insulin and OAD Therapy." Abstract 2416-PO; Presented at the 72nd Scientific Session at the American Diabetes Association Meeting, 2012, A609, one page.
Colino et al., "Therapy with insulin glargine (Lantus) in toddlers, children and adolescents with type 1 diabetes," Diabetes Research and Clinical Practice (2005), vol. 70, pp. 1-7.

(56) References Cited

OTHER PUBLICATIONS

Correa, "Pautas para el examen de patentes farmaceuticas. Una perspectiva desde la Salud Publica. Documento de Trabajo" Universidad de Buenos Aires, Mar. 2008, see pp. 19-20, pp. 1-66.
Crapo et al., "Postprandial plasma-glucose and -insulin responses to different complex carbohydrates," Diabetes 26 (12):1178-83 (Dec. 1977).
Cryer "Hypoglycemia is the limiting factor in the management of diabetes," Diabetes Metab. Res. Rev. 15(1):42-46 (Jan.-Feb. 1999).
Czech et al., "Proteolytical processing of mutated human amyloid precursor protein in transgenic mice" Molecular Brain Research 47:108-116 (1997).
D'Alessio et al., "Glucagon-like Peptide 1 Enhances Glucose Tolerance Both by Stimulation of Insulin Release and by Increasing Insulin-independent Glucose Disposal," J. Clin. Invest. 93(5):2263-66 (1994).
D'Alessio et al., "GLP-1 Receptor Agonists: Strategies for PPG Control," Medical Nursing Edu., 3:1-26 (Jan. 2011).
Database, ADISCTI, "A randomized, 4-sequence, cross-over, double bind, dose response study of 0.4, 0.6 and 0.09 U/kg insluin glarine U300 compared to 0.4 U/kg Lantus U100 in patients with diabetes mellitus type I using euglycemic; clamp technique" last updated Dec. 16, 2010, pp. 1-4.
Davis How to Convert mg to mmol/L, available online at http://www.ehow.com/how_8498850_convert mg-mmoll.html (accessed on Nov. 11, 2015).
Deacon et al., "Dipeptidyl Peptidase IV Inhibition Potentiates the Insulinotropic Effect of Glucagon-Like Peptide 1 in the Anesthetized Pig," Diabetes 47(5):764-69 (1998).
Deacon et al., "Dipeptidyl Peptidase IV Resistant Analogues of Glucagon-Like Peptide-1 Which Have Extended Metabolic Stability and Improved Biological Activity," Diabetologia 41(3):271-78 (1998).
de Arriba et al., "Carbonyl stress and NMDA receptor activation contribute to methylglyoxal neurotoxicity" Free Radical Biology & Medicine, 40:779-90 (2006).
Definition of palliative, http://medicaldictionary.thefreedictionary.com/, accessed on Nov. 6, 2014, pp. 1-2.
Definition of sphincter of pancreatic duct in the Medical Dictionary, http://medicaldictionary.thefreedictionary.com/, accessed on May 22, 2014, pp. 1-2.
Definition of indication, Merriam-Webster online, accessed Oct. 22, 2010.2015, 2 pages.
DeFronzo "Effects of Exenatide (Exendin-4) on Glycemic Control and Weight Over 30 Weeks in Metformin-Treated Patients with Type 2 Diabetes", Diabetes Care 28(5):1092-1100 (May 2005).
DeFronzo "Pathogenesis of Type 2 Diabetes Implications for Metformin" Short Communication, Drugs 1999; 58(Suppl 1):29-30 (Sep. 1999).
DeFronzo "Pharmacologic Therapy for Type 2 Diabetes Mellitus." Ann Int Med. 131:281-303 (1999).
Delatour et al., "Alzheimer pathology disorganizes cortico-cortical circuitry: direct evidence from a transgenic animal model" Neurobiology of Disease, 16:41-47 (2004).
De Le Pena, "Pharmacokinetics and Pharmadynamics of High-Dose Human Regular U-500 Insulin Versus Human Regular U-1 00 Insulin in Healthy Obese Subjects" Diabetes Care, 34(12):2496-501 (2011).
De Rosa, et al. "Intranasal administration of nerve growth factor (NGF) rescues recognition memory deficits in A D11 anti-NGF transgenic mice." Proc Natl Acad. Sci., 102:3811-16 (2005).
DeWitt, "Case Study: Treating New On-Set Catabolic Type 2 Diabetes With Glargine and Lispro", Clinical Diabetes vol. 24, No. 4, pp. 180-181, (Oct. 2006).
deVries et al., "Sequential intensification of metformin treatment in type 2 diabetes with liraglutide followed by randomized addition of basal insulin prompted by A1C targets." Diabetes Care 35:1446-54 (2012).
Diabetes Prevention Program Research Group. "Reduction in the incidence of type 2 diabetes with lifestyle intervention or metformin." N. Engl J. Med. 346(6):393-403 (2002).
Distiller et al., Poster: "Pharmacokinetics and Pharmacodynamics of a New GLP-1 Agonist AVE0010 in Type 2 Diabetes Patients" Meeting: 68th Scientific Sessions (Jun. 2008) Poster No. 520-P.
Dixon et al., "Regeneration of Insulin Activity From the Separated and Inactive A and B Chains," Nature, vol. 188, No. 1752 (1960), pp. 721-724.
Donelli, "Plastic Biliary Stent Occlusion: Factors Involved and Possible Preventive Approaches," Clinical Medicine & Research 5(1):53-60 (Mar. 2007). 7.
Doyle et al., "Mechanisms of action of glucagon-like peptide 1 in the pancreas" Pharmacal Ther. (Mar. 2007) pp. 546-593, vol. 113, No. 3.
Drury et al., "Diabetic nephropathy," British Medical Bulletin, vol. 45, No. 1, 1989, pp. 127-147.
Drucker, "The Biology of Incretin Hormones," Cell Metab. 3(3):153-65 (2006).
Drucker, "Glucagon-Like Peptides," Diabetes 47(2):159-69 (1998).
Drucker, "Mini review: The Glucagon-Like Peptides," Endocrinology 142(2):521-27 (2001).
Kanazawa et al., "Criteria and Classification of Obesity in Japan and Asia-Oceania", Asia Pacific J. Clin Nutr. 11 (Suppl. 7):S732-S737 (Dec. 2002).
Kang et al., "Subcutaneous Insulin Absorption Explained by Insulin's Physicochemical Properties-Evidence from Absorption Studies of Soluble Human Insulin and Insulin Analogues in Humans," Diabetes Care, 14(11):942-48 (Nov 1991).
Kao et al., "The evaluation of gallbladder function by quantitative radionuclide cholescintigraphy in patients with ioninsulin-dependent diabetes mellitus." Nucl. Med Commun.14(10):868-72 (1993).
Kapitza et al., Abstract "Pharmacodynamic Characteristics of Lixisenatide QD vs Liraglutide QD in Patients with T2DM Inadequately Controlled with Metformin" Abtract D-0740, presented at the World Diabetes Congress in Dubai, Dec. 5-8, 2011, one page.
Kastin et al., "Interactions of Glucagon-like peptide (GLP-1) with blood brain barrier" Journal of Molecular Neuroscience (2001) pp. 7-14, vol. 18, No. 2.
Kastin et al., "Entry of exedin-4 into brain is rapid but may be limited at high doses" International Journal Of Obesity And Related Metabolic Disorders: Journal Of The International Association For The Study Of Obesity (2003) vol. 27 No. 3, pp. 313-318.
Kemmler et al., "Studies on the Conversion of Proinsulin to Insulin," The Journal of Biological Chemistry, 246(22):6786-91 (1971).
Kendall et al., "Effets of Exenatide (Exendin-4) on Glycemic Control Over 30 Weeks in Patients With Type 2 Diabetes Treated With Metformin and a Sulfonylurea" Diabetes Care 28:1083-91 (May 2005).
Kielgast et al., "Treatment of type 1 diabetic patients with glucagon-like peptide-1 (GLP-1) and GLP-1R agonists." Curr Diabetes Rev. 5(4):266-75 (Nov. 2009).
Kim et al, "Exendin-4 protects dopaminergic neurons by inhibition of microglial activation and matrix metalloproteinase-3 expression in an animal model of Parkinson's disease," J. Endocrin. 202:431-439 (2009).
Kohner "Diabetic retinopathy," British Medical Bulletin, vol. 45, No. 1, 1989, pp. 148-173.
Knee et al., "A Novel Use of U-500 Insulin for Continuous Subcutaneous Insulin Infusion in Patients With Insulin Resistance: a Case Series", Endocrine Practice, 9(3):181-86 (May/Jun. 2003).
Knudsen et al., "Potent Derivatives of Glucagon-Like Peptide-1 With Pharmacokinetic Properties Suitable for Once Daily Administration", J. Med. Chem. 43(9):1664-69 (2000).
Kohn et al., "pi-shifted insulin analogs with extended in vivo time action and favorable receptor selectivity," Peptide 28:935-48 (2007).
Kolterman et al., "Synthetic Exendin-4 (Exenatide) Significantly Reduces Postprandial and Fasting Plasma Glucose in Subjects with Type 2 Diabetes," J. Clin. Endocrine. Metab. 88(7):3082-89 (2003).
Korczyn and Nussbaum, "Emerging Therapies in the Pharmacological Treatment of Parkinson's Disease," Drugs 62:775-766 (2002).
Krishnamurthy et al., Constancy and variability of gallbladder ejection fraction: impact on diagnosis and therapy. J Nucl Med. 45(11):1872-77 (Nov. 2004).
Lando' "The New 'Designer' Insulins", Clinical Diabetes, 18(4): Fall 2000 (http://journal.diabetes.org/clinicaldiabelesN18N42000/pg154.hlm; accessed Oct. 22, 2013, pp. 1-13).

(56) References Cited

OTHER PUBLICATIONS

Langston et al., "Chronic Parkinsonism in Humans Due to a Product of Meperedine-Analog Synthesis" Science 219 (4587):979-80 (1983).
Langui et al., "Subcellular Topography of Neuronal AβPeptide in APPxPS1 Transgenic Mice" American Journal of Pathology 165(5):1465-77 (2004).
Lantus® Annex I—Summary of product characteristics. Date of first authorisation: Jun. 9, 2000, pp. 1-164.
Lantus® Product Information—European Medicines Agency, first published Aug. 5, 2009, pp. 1-2.
Larsen et al., "Sequence-Assisted Peptide Synthesis (SAPS)," J. Pept. Res. 52(6):470-76 (1998).
Lee et al. "Ischemia-induced changes in glucagon-like peptide-1 receptor and neuroprotective effect of its agonist exenchn-4, in experimental transient cerebral ischemia" J Neurosc Res (2009) pp. 1103-1113, vol. 89.
Leib et al., "Direct quantitation of peptide mixtures without standards using clusters formed by electrospray ionization mass spectrometry." Anal Chem. 81(10):3965-72 (May 2009).
Lens, "The terminal carboxyl groups of insulin," Biochimica et Biophysica Acta 3:367-70 (1949).
Levene & Simms, "Calculation of isoelectric point," J Biol Chem. 55:801-13 (1923).
Levin et al., "Combination therapy with insulin glargine and exenatide: real-world outcomes in patients with type 2 diabetes." Current Medical Research & Opinion 28(2):1-8 (2012).
Leyer et al., "The role of the C-terminus of the insulin B-chain in modulating structural and functional properties of the hormone," Int J Pep Protein Res. 46(5):397-407 (1995).
Levine et al., "Oxidation of Methionine in Proteins: Roles in Antioxidant Defense and Cellular Regulation" IUBMB Life, 50:301-07 (Oct. 2000).
Li et al., "Chronic treatment of exendin-4 affects cell proliferation and neuroblast differentiation in the adult mouse hippocampal dentate gyrus." Neurosci Lett 19:1205-19 (2010).
Li et al., "GLP-1 Receptor Stimulation Reduces Amyloid-beta Peptide Accumulation and Cytotoxicity in Cellular and Animal Models of Alzheimer's Disease" J Alzheimers Dis (2010) pp. 1205-1219, vol. 19.
Li et al., "GLP-1 receptor stimulation preserves primary cortical and dopaminergic neurons in cellular and rodent models of stroke and Parkinsons" PNAS (2009) pp. 1285-1290, vol. 106, No. 4.
Li et al., "Enhancing the GLP-1 receptor signaling pathway leads to proliferation and neuroprotection in human neuroblastoma cells" Journal of Neurochemistry, 113:1621-631 (2010).
Li & Holscher, "Common pathological processes in Alzheimer disease and type 2 diabetes: A review" Brain Research Reviews, 56:384-402 (2007).
Lill, "Production of fast-acting insulins and delayed-release insulins—how can this problem be solved by technology? Insulin formulations," Pharmazie in unserer Zeit 30(1):56-61 (2001). (English Translation Included).
"Lixisenatide, Chemical Structure CID 16139342, Pubchem, accessed Feb. 5, 2015 at URL pubchem.ncbi.nlm.nih.gov/summary/summary.cgi?sid=135267128&viewopt=Deposited, pp. 1-3.".
Liu & Ruus, Abstract "Pharmacokinetics and Safety of the GLP-1 Agonist AVE0010 in Patients with Renal Impairment," Diabetes 58 (Suppl. 1): Abstract 557-P for the 69th Scientific Session of the American Diabetes Association Jun. 5-9, 2009, New Orleans, Louisiana, pp. 1-2.
Lopez-Delgado et al., "Effects of Glucagon-Like Peptide I on the Kinetics of Glycogen Synthase a in Hepatocytes from Normal and Diabetic Rats," Endocrinology 139(6):2811-2817 (1998).
Lotharius et al., "Effect of Mutant a-Synuclein on Dopamine Homeostasis in a New Human Mesencephalic Cell Line," Journal of Biological Chemistry, 277:38884-94 (2002).
Lotharius et al., "Progressive Degeneration of Human Mesencephalic Neuron-Derived Cells Triggered by Dopamine-Dependent Oxidative Stress Is Dependent on the Mixed-Lineage Kinase Pathway," Journal of Neuroscience, 25:6329-42 (2005).
Lougheed et al., "Physical Stability of Insulin Formulations," Diabetes, 32(5):424-32 (May 1983).
Lyxumia® Annex I—Summary of product characteristics. Date of first authorisation: Feb. 1, 2013, pp. 1-92.
Lyxumia® Product Information—European Medicines Agency, first published Mar. 14, 2013, pp. 1-2.
Lyxumia 10 micrograms solution for injection, Summary of Product Characteristics, updated Oct. 31, 2014, pp. 1-12.
Lyxumia, Chemical Subgroup A10BX, Community Register of Medicinal Products for Human Use, European Commission Public Health, p. 1 (May 2, 2013).
Mancuso et al., "Clinical features and pathogenesis of Alzheimer's disease: involvement of mitochondria and mitochondrial DNA," Adv Exp Med Biol., 685:34-44 (2010).
Marbury, et al., "A Pilot Study to Examine the Feasability of Insulin Glargine in Subjects With Impaired Fasting Glucose, Impaired Glucose Tolerance or New-Onset Type 2 Diabetes", Experimental and Clinical Endocrinology & Diabetes: Official Journal, German Society of Endocrinology and German Diabetes Associate, 116(5):282-88 (May 2008).
Margolis, "Diagnosis of Huntington's Disease,"Ciin. Chem. 49:1726-32 (2003).
Markussen et al., "Soluble, prolonged-acting insulin derivatives. I. Degree of protraction and crystallizability of insulins substituted in the termini of the B-chain," Prot. Eng. 1(3), 1987, pp. 205-213.
Markussen et al., "Soluble, prolonged-acting insulin derivatives. II. Degree of protraction and crystallizability of nsulins substituted in positions A17, B8, B13, B27 and B30," Prot. Eng. 1(3), 1987, pp. 215-223.
Markussen et al., "Soluble, prolonged-acting insulin derivatives. III. Degree of protraction, crystallizability and chemical stability of insulins substituted in positions A21, B13, B23, B27 and B30," Prot. Eng. 2(2), 1988, pp. 157-166.
Martin et al. "Neurodegenation in excitotoxcity, global cerebral ischemia, and target deprivation: A perspective on the contributions of aptopsis and necrosis," Brain Res. Bull, 46:281-309 (1998).
Martin et al., "Exendin-4 improves glycemic control, ameliorates brain and pancreatic pathologies and extends survival in a mouse model of Huntington's Disease" Diabetes (2009) pp. 318-328, vol. 58, No. 2.
Mattson "Calcium and neurodegeneration." Aging Cell 6:337-50 (2007).
McClean et al., "The diabetes drug Liraglutide prevents degenerative processes in a mouse model of Alzheimer's disease" Journal of Neuroscience 31(17):6587-94 (2011).
McClean. et al., "Glucagon-like peptide-1 analogues enhance synaptic plasticity in the brain: A link between diabetes and Alzheimer's disease" European Journal of Pharmacology (2010) pp. 158-162, vol. 630.
Mecklenburg & Guinn, "Complications of insulin pump therapy: the effect of insulin preparation," Diabetes Care 8(4):367-70 (1985).
Medline Plus, "Obesity" available at http://www.nlm.nih.gov/medlineplus/obesity.html, Retrieved Aug. 22, 2013, one page.
Meier, "GLP-1 receptor agonists for individualized treatment of type 2 diabetes mellitus." Nat. Rev. Endocrinol. 8:728-42 (2012).
Merrifield, "Solid Phase Synthesis." Science 232(4748):341-47 (1986).
Mikhail, "Is liraglutide a useful addition to diabetes therapy?" Endocr Practice 16(6):1028-37 (Nov.-Dec. 2010).
Monnier et al., The loss of postprandial glycemic control precedes stepwise deterioration of fasting with worsening diabetes. Diabetes Care. 30(2):263-69 (2007).
Moreno-Gonzalez et al., "Extracellular Amyloid-β and Cytotoxic Glial Activation Induce Significant Entorhinal neuron Loss in Young PS1M146LJAPP751SL Mice" Journal of Alzheimer's Disease 18:755-776 (2009).
Moretto et al., "Efficacy and Tolerability of Exenatide Monotherapy Over 24 Weeks in Antidiabetic Drug-Naive Patients with Type 2 Diabetes: A Randomized, Double-Blind, Placebo-Controlled, Parallel-Group Study", Clinical Therapeutics, 30(8):1448-60 (Aug. 2008).

(56) References Cited

OTHER PUBLICATIONS

Muller et al., "Insulin Signaling in the Yeast Saccharomyces cerevisiae. 1. Stimulation of Glucose Metabolism and Snf 1 Kinase by Human Insulin," Biochemistry, 37(24):8683-95 (Jun. 1998).
Muzaffar et al., "The Mechanism of Enhanced Insulin Amyloid Fibril Formation by NaClIs Better Explained by a Conformational Change Model," PLoS One, Nov. 21, 2011, pp. 1-11, 6(11):e27906.
Nakagawa et al., "Receptor gene expression of glucagon-like peptide-1, but not of glucose-dependent insulinotropic polypeptide, in rat nodose ganglion cells" Auton Neurosci (2004) pp. 36-43, vol. 110.
Nathan et al., "Insulinotropic Action of Glucagon like Peptide-1-(7-37) in Diabetic and Nondiabetic Subjects," Diabetes Care 15(2):270-76 (1992).
Nathan et al., "Management of hyperglycaemia in type 2 diabetes mellitus: a consensus algorithm for the initiation and adjustment of therapy. Update regarding the thiazolidinediones." Diabetologia. 51(1):8-11 (2008).
Nauck et al., "Effects of Subcutaneous Glucagon-Like Peptide 1 (GLP-1 [7-36 Amide]) in Patients with NIDDM," Diabetologia 39(12):1546-53 (1996).
Nauck et al.! " Glucagon-like peptide 1 (GLP-1) as a new therapeutic approach for type 2-diabetes," Exp. Clin. Endocrinol. Diabetes 105(4):187-95 (1997).
Nauck et al., "Glucagon-Like Peptide 1 and its Potential in the Treatment of Non-Insulin-Dependent Diabetes Mellitus," Horm. Metab. Res. 29(9):411-16 (1997).
Nauck et al., "Comparative evaluation of incretin-based antidiabetic medications and alternative therapies to be added to melformin in the case of monotherapy failure," Journal of Diabetes Investigation 1(1-2):24-36 (Feb.-Apr. 2010).
NCT00715624 Clinical Trials.gov "GLP-1 Receptor Agonist Lixisenatide in Patients With Type 2 Diabetes for Glycemic Control and Safety Evaluation, on Top of Basal Insulin (GETGOAL-L)" (2008-2014), p. 1-6 (Feb. 2011). D6 version.
NCT00976937, ClinicalTrials.gov, "24-week Study Comparing Lixisenatide (AVE0010) to Sitagliptin as add-on to Metformin in Obese Type 2 Diabetic Patients Younger Than 50," May 6, 2011, Retrieved Nov. 7, 2011, pp. 1-4.
NCT00712673, Clinical Trials.gov, "GLP-A Agonist AVE0010 (Morning or Evening) in Patients with Type 2 Diabetes for Glycemic Control and Safety Evaluation, on Top of Metformin", Mar. 22, 2011, pp. 1-4.
NCT00975286, Clinical Trials.gov, "24-week Treatment with Lixisenalide in Type 2 Diabetes Insufficiently Controlled With Melformin and Insulin Glargine", Aug. 8, 2011, pp. 1-4.
NCT00688701 Clinical Trials.gov "GLP-1 Receptor Agonist Lixisenatide in Patients with Type 2 Diabetes for Glycemic Control and Safety Evaluation in Monotherapy (GETGOAL-MONO)" accessed Jul. 27, 2014; pp. 1-5.
NCT02058147 ClinicalTrials.gov "Efficacy and Safety of Insulin Glargine/Lixisenatide Fixed Ratio Combination Compared to Insulin Glargine Alone and Lixisenatide Alone on Top Metformin in Patients With T2DM (LixLan-O)" first received by ClinicalTrials.gov on Feb. 6, 2014, pp. 1-3.
NCT02058160 ClinicalTrials.gov "Efficacy and Safety of the Insulin Glargine/Lixisenatide Fixed Ratio Combination Versus Insulin Glargine in Patients With Type 2 Diabetes (LixiLan-L)" first received by ClinicalTrials.gov on Feb. 6, 2014, pp. 1-3.
NCT01195454, NIH Clinical Trials, "Euglycemic clamp dose-response study comparing insulin glargine U300 with Lantus U100" last updated Dec. 13, 2010, pp. 1-4.
NCT01255163, ClinicalTrials.gov "A Clinical Trial of Exendin-4 for the Treatment of Alzheimer's Disease" accessed Aug. 8, 2011, pp. 1-7.
NCT01174810, ClinicalTrials.gov "Exendin-4 as a Treatment for Parkinson's Disease—Pilot Study" accessed Aug. 8, 2011, pp. 1-5.
EFC10780 (Sanofi study), "A randomized, double-blind, double-dummy, 2-arm parallel-group, multicenter 24-week study comparing the efficacy and safety of AVE0010 to sitagliptin as add-on to metformin in obese type 2 diabetic patients younger than 50 and not adequately controlled with metformin (EFC10780)" p. 1-4 (Jan. 29, 2014).
EFC10781 Clinical Trials, "24-week Treatment With Lixisenatide in Type 2 Diabetes Insufficiently Controlled With Metformin and Insulin Glargine" ClinicalTrials.gov; EFC10781 pp. 1-5 (Sep. 2009).
EFC6018; Clinical trial EudraCT 2007-005887-29, "GETGOAL-MONO" accessed Jul. 27, 2014; pp. 1-16.
Needleman et al., "A General Method Applicable to the Search for Similarities in the Amino Acid Sequence of Two Proteins," J. Mol. Biol. 48:443-453 (1970).
Neidle, "18.2 Failure Modes in the Discovery Process" Cancer Drug Design and Discovery, Elsevier/Academic Press, pp. 427-431 (2008).
Nettleton et al. "Characterization of the Oligomeric States of Insulin in Self-Assembly and Amyloid Fibril Formation by Mass Spectrometry," Biophysical J., v79, 2000, p. 1053-1065.
Nicklas et al.., "Inhibition of NADH-Linked Oxidation in Brain Mitochondria by 1-Methyl-4-Phenyl-Pyridine, a Metabolite of the Neurotoxin, 1-Methyl-4-Phenyl-1,2,5,6-Tetrahydropyridine" Life Sciences 36:2503-508 (1985).
Nielsen et al., "Pharmacology of Exenatide (Synthetic Exendin-4): A Potential Therapeutic for Improved Glycemic Control of Type 2 Diabetes," Regul. Pept. 117(2):77-88 (2004).
Noble, et al., "Insulin Lispro: A Fast-Acting Insulin Analog," Am Fam Physician, 57(2):279-86 (1998).
Organization for Economic Co-Ooperation and Development; OECD Principles of Good Laboratory Practice and Compliance Monitoring (as revised in 1997); ENV/MC/CHEM (98)17:1-41 (Jan. 21, 1998).
Orskov, "Glucagon-like Peptide-1, a New Hormone of the Entero-insular Axis," Diabetologia 35(8):701-711 (1992).
Ott et al., "Diabetes in Germany" (DIG) study. "A prospective 4-year-follow-up study on the quality of treatment for type 2 diabetes in daily practice." Dtsch Med Wochenschr. 134(7):291-7 (2009). English Absract submitted.
Park et al., "PPARalpha agonis fenofibrate improves diabetic nephropathy in db/db mice," Kidney International, 69:1511-17 (published online Mar. 1, 2006).
Parkin "Guideline for Management of Postmeal Glucose" International Diabetes Federation, pp. 1-32 (Oct. 2007).
Patel & Advance Collaborative Group, "Effects of a fixed combination of perindopril and indapamide on macrovascular and microvascular outcomes in patients with type 2 diabetes mellitus (the Advance trial): a randomised controlled trial." Lancet 370(9590):829-40 (2007).
Patel & Borchardt, "Chemical pathways of peptide degradation. II. Kinetics of deamidation of an asparaginyl residue in a model hexapeptide," Pharmaceutical Research 7(7):703-11 (1990).
Non-Final Office Action from U.S. Appl. No. 12/617,805; mailed May 2, 2012, pp. 1-11.
Final Office Action from U.S. Appl. No. 12/617,805; mailed Jan. 12, 2012, pp. 1-14.
Non-Final Office Action from U.S. Appl. No. 12/617,805; mailed May 10, 2011, pp. 1-12.
Non-Final Rejection issued in U.S. Appl. No. 13/509,507; mailed Dec. 8, 2015, pp. 1-14.
Final Rejection issued in U.S. Appl. No. 13/509,507; mailed Jul. 23, 2015, pp. 1-11.
Non-Final Rejection issued in U.S. Appl. No. 13/509,507; mailed Feb. 19, 2015, pp. 1-10.
Non-Final Rejection issued in U.S. Appl. No. 13/509,507; mailed Sep. 19, 2014, pp. 1-9.
Non-Final Rejection issued in U.S. Appl. No. 13/509,507; mailed Aug. 6, 2013, pp. 1-11.
Non-Final Rejection issued in U.S. Appl. No. 13/509,542; mailed Aug. 11, 2015, pp. 1-30.
Final Rejection issued in U.S. Appl. No. 13/509,542, mailed Jan. 28, 2015, pp. 1-26.
Non-Final Rejection issued in U.S. Appl. No. 13/509,542; mailed Apr. 2, 2014, pp. 1-20.
Final Rejection issued in U.S. Appl. No. 13/509,542; mailed Nov. 21, 2013, pp. 1-34.

(56) References Cited

OTHER PUBLICATIONS

Non-Final Rejection issued in U.S. Appl. No. 13/509,542; mailed May 23, 2013, pp. 1-21.
Final Rejection issued in U.S. Appl. No. 14/172,151; mailed Jul. 20, 2015, pp. 1-18.
Non-Final Rejection issued in U.S. Appl. No. 14/172,151; mailed Mar. 24, 2015, pp. 1-16.
Non-Final Rejection issued in U.S. Appl. No. 14/220,562; mailed Apr. 8, 2015, pp. 1-18.
Non-Final Rejection issued in U.S. Appl. No. 13/700,631; mailed Apr. 22, 2013, pp. 1-27.
Non-Final Rejection issued in U.S. Appl. No. 13/700,631; mailed Nov. 29, 2013, pp. 1-23.
Final Rejection issued in U.S. Appl. No. 13/700,631; mailed Jun. 18, 2014, pp. 1-25.
Non-Final Rejection issued in U.S. Appl. No. 13/700,631; mailed Nov. 18, 2014, pp. 1-22.
Final Rejection issued in U.S. Appl. No. 13/700,631; mailed Apr. 13, 2015, pp. 1-19.
Non-Final Rejection issued in U.S. Appl. No. 13/700,631; mailed Dec. 17, 2015, pp. 1-18.
Non-Final Rejection issued in U.S. Appl. No. 13/819,114; mailed Jul. 31, 2014, pp. 1-9.
Final Rejection issued in U.S. Appl. No. 13/819,114; mailed Mar. 2, 2015, pp. 1-10.
Non-Final Rejection issued in U.S. Appl. No. 13/819,114; mailed Dec. 2, 2015, pp. 1-14.
Non-Final Rejection issued in U.S. Appl. No. 13/363,956; mailed Apr. 10, 2013, pp. 1-15.
Non-Final Rejection issued in U.S. Appl. No. 13/363,956; mailed Nov. 20, 2013, pp. 1-10.
Final Rejection issued in U.S. Appl. No. 13/363,956; mailed May 20, 2014, pp. 1-16.
Non-Final Rejection issued in U.S. Appl. No. 13/363,956; mailed Feb. 11, 2015, pp. 1-18.
Non-Final Rejection issued in U.S. Appl. No. 13/363,956; mailed May 29, 2015, pp. 1-17.
Non-Final-Rejection issued in U.S. Appl. No. 13/432,811; mailed Apr. 8, 2013, pp. 1-7.
Non-Final-Rejection issued in U.S. Appl. No. 13/432,811; mailed Jul. 29, 2014, pp. 1-8.
2013 Final-Rejection issued in U.S. Appl. No. 13/432,811; mailed Sep. 6, 2013, pp. 1-8.
Final-Rejection issued in U.S. Appl. No. 13/432,811; mailed Dec. 12, 2014, pp. 1-8.
Final-Rejection issued in U.S. Appl. No. 13/432,811; mailed Mar. 31, 2015, pp. 1-9.
Non-Final-Rejection issued in U.S. Appl. No. 13/432,811; mailed Sep. 9, 2015, pp. 1-11.
Non-Final Rejection issued in U.S. Appl. No. 13/469,633; mailed Mar. 27, 2013, pp. 1-39.
Non-Final Rejection issued in U.S. Appl. No. 13/469,633; mailed Aug. 19, 2013, pp. 1-25.
Final Rejection issued in U.S. Appl. No. 13/469,633; mailed Dec. 4, 2013, pp. 1-17.
Non-Final Rejection issued in U.S. Appl. No. 13/469,633; mailed Aug. 22, 2014, pp. 1-23.
Final Rejection issued in U.S. Appl. No. 13/469,633; mailed Jan. 23, 2015, pp. 1-12.
Non-Final Rejection issued in U.S. Appl. No. 13/467,707; mailed Jul. 15, 2013, pp. 1-20.
Final Rejection issued in U.S. Appl. No. 13/467,707; mailed Feb. 25, 2014, pp. 1-18.
Non-Final Rejection issued in U.S. Appl. No. 13/467,707; mailed Jul. 25, 2014, pp. 1-22.
Final Rejection issued in U.S. Appl. No. 13/467,707; mailed Jan. 7, 2015, pp. 1-8.
Non-Final Rejection issued in U.S. Appl. No. 13/467,707; mailed Sep. 16, 2015, pp. 1-13.
Final Rejection issued in U.S. Appl. No. 13/110,568; mailed Feb. 21, 2013, pp. 1-20.
Non-Final Rejection issued in U.S. Appl. No. 13/110,568; mailed Mar. 19, 2012, pp. 1-18.
Non-Final Rejection issued in U.S. Appl. No. 13/310,118, mailed Mar. 25, 2015, pp. 1-15.
Non-Final Rejection issued in U.S. Appl. No. 13/310,118, mailed Mar. 29, 2013, pp. 1-21.
Final Rejection issued in U.S. Appl. No. 13/310,118; mailed Aug. 2, 2012, pp. 1-20.
Non-Final Rejection issued in U.S. Appl. No. 13/310,118; mailed Mar. 19, 2012, pp. 1-19.
Non-Final Rejection issued in U.S. Appl. No. 13/467,757; mailed Apr. 17, 2013, pp. 1-9.
Final Office Action issued in U.S. Appl. No. 13/602,913; mailed on Apr. 2, 2015, pp. 1-7.
Non-Final Office Action issued in U.S. Appl. No. 13/602,913; mailed on Dec. 2, 2014, pp. 1-12.
Final Office Action issued in U.S. Appl. No. 13/602,913; mailed on Jun. 20, 2014, pp. 1-27.
Non-Final Office Action issued in U.S. Appl. No. 13/602,913; mailed on Jan. 13, 2014, pp. 1-53.
Final Office Action issued in U.S. Appl. No. 13/602,913; mailed on Sep. 13, 2013, pp. 1-11.
Non-Final Office Action issued in U.S. Appl. No. 13/602,913; mailed on May 17, 2013, pp. 1-7.
Non-Final Rejection in U.S. Appl. No. 13/633,563; mailed Jul. 1, 2013, pp. 1-56.
Final Rejection in U.S. Appl. No. 13/633,563; mailed Dec. 16, 2013, pp. 1-58.
Non-Final Rejection in U.S. Appl. No. 13/633,563; mailed Jun. 4, 2014, pp. 1-11.
Non-Final Rejection in U.S. Appl. No. 13/633,563; mailed Dec. 1, 2014, pp. 1-9.
Final Rejection in U.S. Appl. No. 13/633,563; mailed Apr. 22, 2015, pp. 1-12.
Non-Final Rejection in U.S. Appl. No. 13/633,563; mailed Oct. 6, 2015, pp. 1-12.
Non-Final Rejection in U.S. Appl. No. 13/633,496; mailed Apr. 29, 2013, pp. 1-53.
Final Rejection in U.S. Appl. No. 13/633,496; mailed Nov. 4, 2013, pp. 1-7.
Non-Final Rejection in U.S. Appl. No. 13/633,496; mailed May 22, 2014, pp. 1-11.
Final Rejection in U.S. Appl. No. 13/633,496; mailed Nov. 18, 2014, pp. 1-11.
Non-Final Rejection in U.S. Appl. No. 13/633,496; mailed Apr. 6, 2015, pp. 1-14.
Non-Final Rejection issued in U.S. Appl. No. 13/468,422; mailed Mar. 27, 2013, pp. 1-27.
Non-Final Rejection issued in U.S. Appl. No. 13/468,422; mailed Sep. 16, 2013, pp. 1-19.
Final Rejection issued in U.S. Appl. No. 13/468,422; mailed Jan. 6, 2014, pp. 1-21.
Non-Final Rejection issued in U.S. Appl. No. 13/468,422; mailed Jun. 4, 2014, pp. 1-24.
Final Rejection issued in U.S. Appl. No. 13/468,422; mailed Jan. 23, 2015, pp. 1-27.
Non-Final Rejection issued in U.S. Appl. No. 13/468,422; mailed Nov. 4, 2015; pp. 1-27.
Non-Final Rejection issued in U.S. Appl. No. 13/661,476; mailed Jun. 4, 2015, pp. 1-31.
Final Rejection issued in U.S. Appl. No. 13/661,476, mailed on Oct. 2, 2014, pp. 1-31.
Non-Final Rejection issued in U.S. Appl. No. 13/661,476, mailed on Mar. 6, 2014, pp. 1-28.
Non-Final Rejection issued in U.S. Appl. No. 13/661,476, mailed on Dec. 4, 2013, pp. 1-11.
Non-Final Rejection issued in U.S. Appl. No. 13/661,476, mailed on Sep. 16, 2013, pp. 1-19.
Non-Final Rejection issued in U.S. Appl. No. 13/692,640; mailed Oct. 31, 2013, pp. 1-10.

(56) References Cited

OTHER PUBLICATIONS

Non-Final Rejection issued in U.S. Appl. No. 13/692,640; mailed May 6, 2014, pp. 1-10.
Final Rejection issued in U.S. Appl. No. 13/692,640; mailed Jan. 6, 2015, pp. 1-11.
Final Rejection issued in U.S. Appl. No. 13/692,640; mailed Jun. 2, 2015, pp. 1-12.
Non-Final Rejection issued in U.S. Appl. No. 14/303,895; mailed Sep. 9, 2015, pp. 1-12.
Non-Final Rejection issued in U.S. Appl. No. 14/303,895; mailed May 21, 2015, pp. 1-11.
International Search Report by the ISA for International Application No. PCT/EP2007/005932; dated Oct. 9, 2007, pp. 1-6.
International Search Report by the ISA for International Application No. PCT/EP2009/000017; dated Jun. 22, 2009, pp. 1-7.
International Search Report by the ISA for International Application No. PCT/EP2009/063195; dated May 6, 2010, p. 1.
International Search Report by the ISA for International Application No. PCT/EP2010/059436; dated Jun. 17, 2011, pp. 1-5.
International Search Report by the ISA for International Application No. PCT/EP2010/059438; dated Oct. 4, 2010, pp. 1-3.
International Search Report by the ISA for International Application No. PCT/EP2010/062638; dated Mar. 18, 2011, pp. 1-5.
International Search Report by the ISA for International Application No. PCT/EP2010/067250; dated Mar. 23, 2011, pp. 1-3.
International Search Report by the ISA for International Application No. PCT/EP2011/058079; dated Mar. 22, 2012, pp. 1-6.
International Search Report by the ISA for International Application No. PCT/EP2011/058764; dated Jun. 30, 2011, pp. 1-9.
International Search Report by the ISA for International Application No. PCT/EP2012/051670; dated Mar. 26, 2012, pp. 1-6.
International Search Report by the ISA for International Application No. PCT/EP2012/055660; dated May 10, 2012, pp. 1-15.
International Search Report by the ISA for International Application No. PCT/EP2012/058745; dated Jul. 12, 2012, pp. 1-6.
International Search Report by the ISA for International Application No. PCT/EP2012/058747; dated Jul. 8, 2012, pp. 1-6.
International Search Report by the ISA for International Application No. PCT/EP2012/058749; dated Jul. 31, 2012, pp. 1-6.
International Search Report by the ISA for International Application No. PCT/EP2012/058779; dated Aug. 28, 2012, pp. 1-5.
International Search Report by the ISA for International Application No. PCT/EP2012/067144; dated Aug. 11, 2012, pp. 1-5.
International Search Report by the ISA for International Application No. PCT/EP2012/069485; dated Dec. 11, 2012, pp. 1-5.
International Search Report by the ISA for International Application No. PCT/EP2012/069483; dated Nov. 29, 2011, pp. 1-4.
International Search Report by the ISA for International Application No. PCT/EP2012/071271; dated Jan. 30, 2013, pp. 1-5.
International Search Report by the ISA for International Application No. PCT/EP2012/074150; dated Nov. 20, 2012, pp. 1-4.
International Search Report by the ISA for International Application No. PCT/EP2014/062418; dated Sep. 22, 2014, pp. 1-4.
International Search Report by the ISA for International Application No. PCT/EP2014/051976; dated Mar. 4, 2014, pp. 1-3.
International Search Report by the ISA for International Application No. PCT/EP2014/056498; dated Jun. 25, 2014, pp. 1-10.
Written Opinion of the ISA for International Application No. PCT/EP2011/058079, mailed Mar. 22, 2012, pp. 1-8.
Extended European Search Report for Euorpean Application No. 98 11 0889.7; dated Oct. 14, 1998, pp. 1-4.
Extended European Search Report for European Application No. 09 17 58763; dated Mar. 24, 2010, pp. 1-4.
Extended European Search Report for European Application No. 09 17 5877.1; dated Apr. 29, 2010, pp. 1-5.
Extended European Search Report for European Application No. 10 16 43682; dated Oct. 14, 2010, pp. 1-6.
Extended European Search Report for European Application No. 10 30 5780; dated Nov. 16, 2010, pp. 1-3.
Extended European Search Report for European Application No. 11 15 3106; dated Jul. 6, 2011, pp. 1-12.
Extended European Search Report for European Application No. 11 16 02702; dated Sep. 19, 2011, pp. 1-8.
Extended European Search Report for European Application No. 11 16 6415; dated Mar. 12, 2012, pp. 1-12.
Extended European Search Report for European Application No. 13 305 432.0; dated Sep. 13, 2013, pp. 1-5.
Extended European Search Report for European Application No. 14 16 68772; of Aug. 18, 2014, pp. 1-6.
Extended European Search Report for European Application No. 14 19 7154.9: dated Apr. 8, 2015, pp. 1-7.
English translation of Search Report for Chinese Patent Application No. 20140220537.9; dated Feb. 13, 2015, pp. 1-2.
Search Report of the Intellectual Property Corporation of Malaysia for Malaysian Patent Application No. PI 2011006204; dated Sep. 15, 2015, pp. 1-3.
Search Report of the Indecopi for Patent Application in Peru No. 000643-2012/DIN, dated Jul. 23, 2015, pp. 1-2.
Gygi et al., "Quantitative analysis of complex protein mixtures using isotope-coded affinity tags." Nat Biotechnol. 17(10):994-99 (Oct. 1999).
Xie et al., "Characterization of protein impurities and site-specific modifications using peptide mapping with liquid chromatography and data independent acquisition mass spectrometry." Anal Chem. 81(14):5699-708 (Jul. 2009).
Laursen et al., "Enhanced monitoring of biopharmaceutical product purity using liquid chromatography-mass spectrometry." 1218(28):4340-48 (Jul. 2011; Epub May 2011).
Smolka et al., "Optimization of the isotope-coded affinity tag-labeling procedure for quantitative proteome analysis." Anal Biochem. 297(1):25-31 (Oct. 2001). Abstract only submitted.
Drucker et al., "The incretin system: glucagon-like peptide-1 receptor agonists and dipeptidyl peptidase-4 inhibitors in type 2 diabetes." Lancet; 368(9548):1696-705 (Nov. 11, 2006).
DrugBank, "Insulin glargine," available online at http://www.drugbank.ca/drugs/DB00047, 16 pages. (accessed online Sep. 23, 2014).
Dubois et al., "Revising the definition of Alzheimer's disease: a new lexicon." Lancet Neural. 9: 1118-27 (2010).
During et al., "Glucagon-like peptide-1 receptor is involved in learning and neuroprotection" Nat Med (2003) pp. 1173-1179, vol. 9.
Dunn et al., "Insulin Glargine: An Updated Review of its Use in the Management of Diabetes Mellitus" Drugs 63 (16):1743-1778 (2003).
Eckert et al., "Alzheimer's Disease-like Alterations in Peripheral Cells from Presenilin-1 Transgenic Mice" Neurobiology of Disease 8, 331-342 (2001).
Eng et al., "Isolation and characterization of exendin-4, an exendin-3 analogue, from Heloderma suspectum venom. Further evidence for an exendin receptor on dispersed acini from guinea pig pancreas," J Biol Chem 267(11):7402-5 (1992).
European Medicines Agency—Science Medicines Health, "Guideline on clinical investigation of medicinal products in he treatment of diabetes mellitus" Committee for Medicinal Products for Human Use, Jan. 20, 2010, pp. 1-19.
Executive Summary, "Standards of Medical Care in Diabetes—2009" Diabetes Care, 32(Suppl. 1):S6-S12 (Jan. 2009).
Ex Parte Herrmann, Appeal No. 2009-001777 U.S. Appl. No. 10/616,457 (B. PAI. Nov. 13, 2009).
Fabunmi et al., "Patient characteristics, drug adherence patterns, and hypoglycemia costs for patients with type 2 diabetes mellitus newly initiated on exenatide or insulin glargine." Curr Med Res Opin. 25(3):777-86 (2009).
Faivre et al., "Effect of GIP Analogues in Neuronal Signalling, Cell Proliferation and Learning and Memory." Regulatory Peptides; 164(1):40-41 (Sep. 9, 2010, published online Aug. 20, 2010).
FDA Guidance for Industry, US Department of Health and Human Services, Food and Drug Administration, Center for Drug Evaluation and Research (COER), pp. 1-11, Feb. 2014.

(56) References Cited

OTHER PUBLICATIONS

FDA Frequently Asked Questions about Combination Products; accessed from www.fda.gov/CombinationProducts/AboutCombinationProducts/usm101496.1/htm, 2009 downloaded Jul. 13, 2012, pp. 1-18.
FDA label of Apidra®, May 2014, pp. 1-35.
FDA label of Humalog®, Mar. 2013, pp. 1-27.
FDA label of Lantus®, Oct. 2013, pp. 1-44.
Feinglos et al., "Effects of liraglutide (NN2211), a long-acting GLP-1 analogue, on glycaemic control and bodyweight in subjects with type 2 diabetes." Diabetic Medicine, 22(8):1016-23 (Jul. 2005).
Actrapid® summary of product characteristics, Apr. 2011, pp. 1-11.
Actrapid® prescribing information, Apr. 2011, pp. 1-4.
Apidra® prescribing information, Apr. 2012, pp. 1-6.
Berlinsulin® H summary of product characteristics, Apr. 2012, pp. 1-11.
Berlinsulin® H prescribing information, Apr. 2012, pp. 1-4.
Humalog® prescribing information, Apr. 2012, pp. 1-6.
Insuman® Comb25 prescribing information, Feb. 2011, pp. 1-4.
Insuman® Infusat prescribing information, Feb. 2011, pp. 1-4.
Lantus® prescribing information, May 2012, pp. 1-6.
Levemir® prescribing information, Dec. 2011, pp. 1-6.
Novolog® product information, Oct. 2009, pp. 1-4.
NovoMix® prescribing information, Feb. 2011, pp. 1-5.
NovoRapid® prescribing infonnation, Jul. 2012, pp. 1-5.
Fieller, Symposium on Interval Estimation; "Some Problems with Interval Estimation" Journal of the Royal Statistical Society 16(2):175-85 (1954).
Fonseca et al., "Efficacy and Safety of the Once-Daily GLP-1 Receptor Agonist Lixisenatide in Monotherapy" Diabetes Care, 35:1225-31 (Jun. 2012).
Fox et al., Protein Science 10: 622-30 (2001).
Fransson et al., "Oxidation of Human Insulin-Like Growth Factor I in Formulation Studies: Kinetics of Methionine Oxidation in Aqueous Solution and in Solid State" Pharmaceutical Research 13(8):1252-57 (Aug. 1996).
Galloway & Root, "New forms of insulin," Diabetes 21 (2 Suppl):637-48 (1972).
Gallwitz, "Liraglutide. GLP-1 Receptor Agonist Treatment of Type 2 Diabetes Treatment of Obesity," Drugs of the Future, 33(1):13-20 (Jan. 2008).
Gandhi & Wood, "Molecular pathogenesis of Parkinson's disease." Hum Mol Genet 14:2749-55 (2005).
Garber et al., "Liraglutide versus glimepiride monotherapy for type 2 diabetes (LEAD-3 Mono): a randomised, 52-week, phase III, double blind, parallel-treatment trial", The Lancet, 373(9662):473-81 (Feb. 7, 2009).
Garg, R., et al., "U-500 insulin: why, when and how to use in clinical practice", Diabetes/Metabolism Research and Reviews, 23:265-268 (2007).
Garriques et al., "The Effect of Mutations on the Structure of Insulin Fibrils Studied by Fourier Transform Infrared (FTIR) Spectroscopy and Electron Microscopy," Journal of Pharmaceutical Sciences, 91(12):2473-80 (2002).
Gault et al. "GLP-1 agonists facilitate hippocampal L TP and reverse the impairment oiL TP induced by beta-amyloid." Eur J Pharmacal; 587(1-3):112-7 (Jun. 10, 2008; published online Mar. 29, 2008).
Gavin—Committee Report, "Report of the Expert Committee on the Diagnosis and Classification of Diabetes Mellitus," Diabetes Care, 20(7):1183-97 (Jul. 1997).
Geiger, Chem. Zeitung, 100(3), p. 54-56. (Jan. 1976).
Gengler et al., "Vai(8)GLP-1 rescues synaptic plasticity and reduces dense core plaques in APP/PS1 mice" Neurobiol Aging (2012) pp. 265-276, vol. 33.
Gerich et al., "Monotherapy with GLP-1 receptor agonist, Lixisenatide, significantly improves glycaemic control in type 2 diabetic patients," Presentation abstract 830, 46th Annual Meeting of EASD, Stockholm, Sweden, p. 1 (Sep. 2010).
Giugliano et al., "Treatment regimens with insulin analogues and haemoglobin A1c target of <7% in type 2 diabetes: A systematic review." Diabetes Research and Clinical Practice 92(1):1-10 (2010).
Goke et al., "Distribution of GLP-1 Binding Sites in the Rat Brain: Evidence that Exendin-4 is a Ligand of Brain GLP-1 Binding Sites," Eur. J. Neurosci. 7(11):2294-2300 (1995).
Goke et al., "Exendin-4 is a High Potency Agonist and Truncated Exendin-(9-39)-amide an Antagonist at the Glucagon-like Peptide 1-(7-36)-amide Receptor of Insulin-secreting beta-Cells," J. Biol. Chem. 268:19650-55 (1993).
Goldstein et al.. Tests of Glycemia in Diabetes. Diabetes Care 18(6):896-909 (Jun. 1995).
Schapira, "Causes of neuronal death in Parkinson's disease." Adv Neurol 86:155-162 (2001).
Schellenberger et al., "Attempts for Quantifying the S' Subsite Specificity of Serine Proteases," Selected Papers Presented At the 2nd International Meeting on The Molecular And Cellular Regulation of Enzyme Activity, Advances in The Biosciences, Peptides and Proteases: Recent Advances 65:159-66 (1987).
Schellenberger et al., "Protease-Catalyzed Kinetically Controlled Peptide Synthesis," Angewante Chemie, International Edition 30(11):1437-49 (1991).
Schindowski et al., "Impact of Aging: Sporadic, and Genetic Risk Factors on Vulnerability to Apoptosis in Alzheimer's Disease" NeuroMolecular Medicine, 4:161-177 (2003).
Schmitz et al., "Hippocampal Neuron Loss Exceeds Amyloid Plaque Load in a Transgenic Mouse Model of Alzheimer's Disease" American Journal of Pathology, 164(4):1495-1502 (2004).
Schwartz et al., "A superactive insulin: [B10-Aspartic acid]insulin(human)," Proc. Natl. Acad. Sci. USA, 84(18):6408-11 (Sep. 1987).
Schubert-Zsilavecz et al., "Better blood sugar control in diabetics. Insulin glargin—a long acting insulin analogue," Pharmazie in Unserer Zeit 30(2):125-30 (2001). With English translation.
Secnik Boye et al., "Patient-reported outcomes in a trial of exenatide and insulin glargine for the treatment of type 2 diabetes," Health and Quality of Life Outcomes, vol. 4, No. 80, pp. 1-8 (Oct. 2006).
Seino et al., "Randomized, double-blind, placebo-controlled trial of the once-daily GLP-1 receptor agonist lixisenatide in Asian patients with type 2 diabetes insufficiently controlled on basal insulin with or without a sulfonylurea (GetGoal-L-Asia)." Diabetes, Obesity and Metabolism 14(10):910-17 (2012).
Sharplin et al., "Improved glycaemic control by switching from insulin NPH to insulin glargine: a retrospective observational study," Cardiovascular Diabetology, 8(3):1-8 (published Jan. 19, 2009).
Sherer et al., "Subcutaneous Rotenone Exposure Causes Highly Selective Dopaminergic Degeneration and a-Synuclein Aggregation," Experimental Neurology, 179:9-16 (2003).
Sluzky et al., "Kinetics Of Insulin Aggregation In Aqueous Solutions Upon Agitation In The Presence Of Hydrophobic Surfaces," Proc. Natl. Acad. Sci. USA. 88(21):9377-81 (Nov. 1991).
Sporn & Suh, "Chemoprevention of cancer" Carcinogenesis, 21(3):535-530 (2000).
St. John Providence Health Center, "Preventing Obesity" http://www.stjohnprovidence.org/HealthInfolib/swarticle.aspx?type=85&id= P07863, Retrieved Aug. 22, 2013, pp. 1-2.
Starkova, ed., "Clinical Endocrinology", Guide for physicians, Moscow, "Medicine", 1991, p. 192-262.
Stolk et al., "Insulin and cognitive function in an elderly population. The Rotterdam Study." Diabetes Care, 20:792-95 (1997).
Summary of Product Characteristics Lyxumia 10 micrograms solution for injection, pp. 1-93, with European Medicines Agency product information, p. 94, published Mar. 14, 2013.
Sundby "Separation and Characterization of Acid-Induced Insulin Transformation Products by Paper Electrophoresis in 7 M Urea," J. Biol. Chem. 237(11):3406-11 (Nov. 1962).
"Suspension" Taber's Cyclopedic Medical Dictionary, 19th Edition, p. 2097 (F.A. Davis Co., Philadelphia 2001).
"Suspension" Stedman's Medical Dictionary, 20th Edition, p. 1450 (Williams & Wilkins Co., Baltimore 1961).
Tanner et al., "Rotenone, Paraquat, and Parkinson's Disease," Environmental Health Perspectives,119:866-872 (2011).

(56) References Cited

OTHER PUBLICATIONS

Tempero, "How I treat Pancreatic Ductal Adenocarcinoma," Current Clinical Issues, Journal of Oncology Practice, vol. 4, Issue 1, pp. 46-47 (2008).

Teramoto et al., "Exendin-4, a glucagon-like peptide-1 receptor agonist, provides neuroprotection in mice transient focal cerebral ischemia" J Cerebr Blood Flow Metab (2011) pp. 1696-1705, vol. 31, No. 8.

Tessari et al., "Insulin in Methionine and Homocysteine Kinetics in Healthy Humans: Plasma Vs. Intracellular Models", Am J. Physiol Endocrine Metab 288(6):E1270-E1276 (2005).

Tetich et al., "Neuroprotective effects of (24R)-1,24-dihydroxycholecalciferol in human neuroblastoma SH-SY5Y cell line" J Steroid Biochemistry & Molecular Biology 89-90:365-70 (2004).

Tews et al., Abstract of Oral Presentation "Enhanced Protection Against Cytokine- and Fatty Acid-induced Apoptosis in Ins-1 Beta-Cells by Combined Treatment with Insulin Glargine and the Novel GLP-1 Receptor Agonist AVE0010" Diabetes, 56(Suppl. 1):A72-A73 (2007).

Tews et al., "Enhanced protection against cytokine- and fatty acid-induced apoptosis in pancreatic beta cells by combined treatment with glucagon-like peptide-1 receptor agonists and insulin analogues." Horm Metab Res. 40(3):172-80 (Mar. 2008).

Thong et al., "Safety, efficacy and tolerability of exenatide in combination with insulin in the Association of British clinical Diabetologists nationwide exenatide audit." Diabetes, Obesity and Metabolism 13:703-10 (2011).

Toth et al., "Neurite sprouting and synapse deterioration in the aging Caenorhabditis elegans nervous system" J Neurosci. 32(26):8778-90 (2012).

Turner et al., UK Prospective Diabetes Study (UKPDS) Group "Glycemic control with diet, sulfonylurea, metformin, or insulin in patients with type 2 diabetes mellitus: Progressive requirement for multiple therapies (UKPDS 49)." JAMA 281(21):2005-12 (1999).

Thurow & Geisen, "Stabilisation of dissolved proteins against denaturation at hydrophobic interfaces,"Diabetologia, 27(2):212-18 (Aug. 1984).

Tyler-Cross Schirch, "Effects of amino acid sequence, buffers, and ionic strength on the rate and mechanism of deamidation of asparagine residues in small peptides," J Biol Chem. 266(33):22549-56 (1991).

UK Prospective Diabetes Study (UKPDS) Group "Intensive blood-glucose control with sulphonylureas or insulin compared with conventional treatment and risk of complications in patients with type 2 diabetes (UKPDS 33)" The Lancet vol. 352 p. 837-853 (Sep. 12, 1998).

UK Prospective Diabetes Study (UKPDS) Group, "Effect of intensive blood-glucose control with metformin on complications in overweight patients with type 2 diabetes (UKPDS 34)" Lancet 352(9131):854-65 (Sep. 1998).

Uttenthel et al., "Molecular forms of flucagon-like peptide-1 in human pancreas and glucagonomas," J. Clin. Endocrinol. Metabol. 61(3):472-79 (1985).

Valle et al., "Cisplatin plus Gemcitabine versus Gemcitabine for Biliary Tract Cancer," N Engl J Med. 362 (14)1273-81 (Apr. 2010).

Van Delden, "Pancreas-Carcinoma, CT Assessment of Resectability," Radiology Department of the Academical Medical Centre, pp. 1-12 (Apr. 2006).

Varadarajan et al., "Review: Alzheimer's Amyloid b-Peptide-Associated Free Radical Oxidative Stress and Neurotoxicity," Journal of Structural Biology, 130:184-208 (2000).

Venezia et al., "Apoptotic cell death and amyloid precursor protein signaling in neuroblastoma SH-SY5Y cells," Ann NY Acad Sci, 1030:339-47 (2004).

Victoza Press Release, "Diabetes drugs show promise in Alzheimer's" published Jan. 17, 2011, pp. 1-2.

Victoza® Product information—European Medicines Agency, first published Aug. 7, 2009, pp. 1-2.

Victoza® Annex I—Summary of product characteristics. First published 2009, pp. 1-32.

Volund et al., "In Vitro and in Vivo Potency of Insulin Analogues Designed for Clinical Use," Diab. Med. 8(9):839-47 (Nov. 1991).

Vora et al., "Incretin-based therapy in combination with basal insulin: A promising tactic for the treatment of type 2 diabetes." Diabetes & Metab. 39(1):6-15 (2013).

Wafa et al., "Use of U-500 Regular Insulin in Type 2 Diabetes", Diabetes Care, 29(9):2175-2176 (2006).

Wajchenberg, Chapter 23 "Clinical Approaches to preserve beta-cell function in Diabetes", Adv Exp Med Biol. 654:515-35 (2010).

Wan et al., "Enhancing the Activity of Insulin at the Receptor Interface: Crystal Structure and Photo-Cross-Linking of A8 Analogues," Biochemistry 43:16119-33 (2004).

Wang et al., "Real-world outcomes of US employees with type 2 diabetes mellitus treated with insulin glargine or neutral protamine Hagedorn insulin: a comparative retrospective database study." BMJ Open. 3:e002348 (2013), pp. 1-9.

Ward "Diabetic neuropathy," British Medical Bulletin, 45(1):111-26 (Jan. 1989).

Watson et al., "Insulin increases CSF Aβ42 levels in normal older adults" Neurology 60:1899-1903 (2003).

U.S. Appl. No. 13/123,835, filed Sep. 30, 2011 to Werner et al.
U.S. Appl. No. 13/382,442, filed Mar. 21, 2012 to Schoettle.
U.S. Appl. No. 13/382,772, filed May 29, 2012 to Schoettle.
U.S. Appl. No. 13/509,507, filed Jul. 30, 2014 to Brunner-Schwarz et al.
U.S. Appl. No. 13/509,542, filed Aug. 2, 2012 to Hagendorf et al.
U.S. Appl. No. 14/172,151, filed Feb. 4, 2014 to Bley et al.
U.S. Appl. No. 12/617,805, filed Nov. 13, 2009 to Silvestre et al.
U.S. Appl. No. 12/617,811, filed Nov. 13, 2009 to Silvestre et al.
U.S. Appl. No. 14/220,562, filed Mar. 20, 2014 to Becker et al.
U.S. Appl. No. 13/700,631, filed Nov. 11, 2012 to Becker et al.
U.S. Appl. No. 13/819,114, filed Apr. 29, 2013 to Boka et al.
U.S. Appl. No. 13/363,956, filed Feb. 1, 2012 to Silvestre et al.
U.S. Appl. No. 13/432,811, filed Mar. 28, 2012 to Boka et al.
U.S. Appl. No. 13/469,633, filed May 11, 2012 to Ruus et al.
U.S. Appl. No. 13/467,707, filed May 9, 2012 to Niemoller et al.
U.S. Appl. No. 13/468,422, filed May 10, 2012 to Silvestre et al.
U.S. Appl. No. 13/467,757, filed May 9, 2012 to Silvestre et al.
U.S. Appl. No. 13/633,563, filed Oct. 2, 2012 to Stechl et al.
U.S. Appl. No. 13/602,913, filed Sep. 4, 2012 to Hess et al.
U.S. Appl. No. 13/661,476, filed Oct. 26, 2012 to Silvestre et al.
U.S. Appl. No. 14/303,895, filed Jun. 13, 2014 to Souhami et al.
U.S. Appl. No. 13/633,496, filed Oct. 2, 2012 to Stechl et al.

NCT01146678, ClinicalTrials.gov "Relative Bioavailability and Activity of Different Formulations of Insulin Glargine and Lixisenatide in Patients With Diabetes Mellitus Type 1" last updated Sep. 10, 2010, pp. 1-4.

EMA—Science Medicines Health "TOUJEO" EPAR Summary for the Public, first published Nov. 5, 2009, pp. 1-3.

English Translation of TIPO Search Report for ROC Patent Application No. 101130936, dated Dec. 1, 2015, one page.

Final Rejection issued in U.S. Appl. No. 13/467,707; mailed Feb. 12, 2016, pp. 1-12.

Final-Rejection issued in U.S. Appl. No. 13/432,811; mailed Feb. 10, 2016, pp. 1-9.

Final Rejection issued in U.S. Appl. No. 13/509,542, mailed Feb. 10, 2016, pp. 1-40.

Non-Final Rejection issued in U.S. Appl. No. 13/382,442; mailed Mar. 31, 2016, pp. 1-29.

International Search Report by the ISA for International Application No. PCT/EP2015/079285; dated Mar. 9, 2016, pp. 1-7.

English translation of the TIPO Search Report for ROC Patent Application No. 104116749, dated Feb. 22, 2016, one page.

American Diabetes Association, "Standards of Medical Care in Diabetes—2011 ", Diabetes Care, 34 (Supplement 1): S11-S61 (Jan. 2011).

(56) References Cited

OTHER PUBLICATIONS

European Medicines Agency, Committee for Medicinal Products for Human Use (CHMP), "Assessment report Lyxumia", pp. 1-81 (Nov. 28, 2012).
FDA—Food and Drug Administration, CFR—Code of Federal Regulations Title 21, Chapter 1, Subchapter D, Part 312.21, "Phases of an investigation" pp. 1-2, Apr. 1, 2015.
Miyazaki et al., "Improved glycemic control and enhanced insulin sensitivity in type 2 diabetic subjects treated with pioglitazone", Diabetes Care, 24(4):710-19 (Apr. 2001).
"Remington: The Science and Practice of Pharmacy", Twentieth Edition, Lippincott Williams & Wilkins, USA, pp. 1-5, 2000.
Sanofi Presentation, "Natixis Conference on Diabetes" Pierre Chancel, pp. 1-23, Nov. 8, 2011.
Wikipedia® entry for "Lixisenatide" Retrieved from the Internet: https://en.wikipedia.org/wiki/Lixisenatide one page, retrieved Apr. 11, 2016.
Wikipedia® entry for "Pioglitazone" Retrieved from the Internet: https://en.wikipedia.org/wiki/Pioglitazone pp. 1-3, retrieved Apr. 11, 2016.
Wikipedia® entry for "Metformin" Retrieved from the Internet: https://en.wikipedia.org/wiki/Metformin pp. 1-21, retrieved Apr. 11, 2016.
Wikipedia® entry for "Body mass index" Retrieved from the Internet: https://en.wikipedia.org/wiki/Body mass_index pp. 1-14, retrieved Feb. 26, 2016.
World Health Organisation report on "Definition and diagnosis of diabetes mellitus and intermediate hyperglycemia: report of a WHO/IDF consultation" pp. 1-50 (2006).

* cited by examiner

```
                        SEQUENCE LISTING

<160> NUMBER OF SEQ ID NOS: 2

<210> SEQ ID NO 1
<211> LENGTH: 44
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (44)..(44)
<223> OTHER INFORMATION: AMIDATION, C-terminal

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Ser Lys Lys Lys Lys Lys Lys
            35                  40

<210> SEQ ID NO 2
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (39)..(39)
<223> OTHER INFORMATION: AMIDATION, C-terminal
```

```
<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

PHARMACEUTICAL COMBINATION FOR USE IN GLYCEMIC CONTROL IN DIABETES TYPE 2 PATIENTS

Subject of the present invention is a pharmaceutical combination for use in glycemic control in diabetes type 2 patients, said combination comprising (a) desPro$^{36}$Exendin-4(1-39)-Lys$_6$-NH$_2$ (AVE0010, lixisenatide) or/and a pharmaceutically acceptable salt thereof, and (b) a glitazone or/and a pharmaceutically acceptable salt thereof.

In a healthy person the release of insulin by the pancreas is strictly coupled to the concentration of blood glucose. An increased level of blood glucose, as appears after meals, is rapidly counterbalanced by a respective increase in insulin secretion. In fasting condition the plasma insulin level drops to a basal value which is sufficient to ensure the continuous supply of glucose to insulin-sensitive organs and tissues and to keep the hepatic glucose production at a low level at night.

In contrast to diabetes type 1, there is not generally a lack of insulin in diabetes type 2 but in many cases, particularly in progressive cases, the treatment with insulin is regarded as the most suitable therapy, if required in combination with orally administered anti-diabetic drugs.

An increased glucose level in the blood over several years without initial symptoms represents a significant health risk. It could clearly be shown by the large-scale DCCT study in the USA (The Diabetes Control and Complications Trial Research Group (1993) N. Engl. J. Med. 329, 977-986) that chronically increased levels of blood glucose are a main reason for the development of diabetes complications. Examples for diabetes complications are micro and macrovascular damages that possibly manifest themselves in retinopathies, nephropathies or neuropathies and lead to blindness, renal failure and the loss of extremities and are accompanied by an increased risk of cardiovascular diseases. It can thus be concluded that an improved therapy of diabetes primarily has to aim keeping blood glucose in the physiological range as closely as possible.

A particular risk exists for overweight patients suffering from diabetes type 2, e.g. patients with a body mass index (BMI) ≥30. In these patients the risks of diabetes overlap with the risks of overweight, leading e.g. to an increase of cardiovascular diseases compared to diabetes type 2 patients being of a normal weight. Thus, it is particularly necessary to treat diabetes in these patients while reducing the overweight.

Glitazones (also termed thiazolidinediones) such as pioglitazone are antihyperglycemic agents that reduce insulin resistance by sensitizing muscle, liver and adipose tissue (Dormandy et al., Lancet 2005, 366:1270-89, Yki-Jarvinen, N Engl J Med 2004, 351: 1106-18).

Metformin is a biguanide hypoglycemic agent used in the treatment of non-insulin-dependent diabetes mellitus (diabetes mellitus type 2) not responding to dietary modification. Metformin improves glycemic control by improving insulin sensitivity and decreasing intestinal absorption of glucose. Metformin is usually administered orally. However, control diabetes mellitus type 2 in obese patients by metformin may be insufficient. Thus, in these patients, additional measures for controlling diabetes mellitus type 2 may be required.

The compound desPro$^{36}$Exendin-4(1-39)-Lys$_6$-NH$_2$ (AVE0010, lixisenatide) is a derivative of Exendin-4. Lixisenatide is disclosed as SEQ ID NO:93 in WO 01/04156:

```
SEQ ID NO: 1: Lixisenatide (44 AS)
H-G-E-G-T-F-T-S-D-L-S-K-Q-M-E-E-E-A-V-R-L-F-I-E-W-
L-K-N-G-G-P-S-S-G-A-P-P-S-K-K-K-K-K-K-NH2

SEQ ID NO: 2: Exendin-4 (39 AS)
H-G-E-G-T-F-T-S-D-L-S-K-Q-M-E-E-E-A-V-R-L-F-I-E-W-
L-K-N-G-G-P-S-S-G-A-P-P-P-S-NH2
```

Exendins are a group of peptides which can lower blood glucose concentration. The Exendin analogue lixisenatide is characterised by C-terminal truncation of the native Exendin-4 sequence. Lixisenatide comprises six C-terminal lysine residues not present in Exendin-4.

In the context of the present invention, lixisenatide includes pharmaceutically acceptable salts thereof. The person skilled in the art knows pharmaceutically acceptable salts of lixisenatide. A preferred pharmaceutically acceptable salt of lixisenatide employed in the present invention is acetate.

In the Example of the present invention, it has been demonstrated in diabetes type 2 patients that lixisenatide in an add-on therapy to a glitazone significantly improved glycemic control:

Lixisenatide in combination with pioglitazone ("lixisenatide group") significantly decreased the fasting plasma glucose compared to the pioglitazone group ("placebo group") from baseline to Week 24.

In the lixisenatide group, the HbA$_{1c}$ values were significantly decreased compared to the placebo group from baseline to Week 24.

In the lixisenatide group, the percentages of patients reaching HbA$_{1c}$ values ≤6.5% or ≤7% at Week 24 were significantly higher than in the placebo group.

The fasting plasma insulin concentration was lower in the lixisenatide group, compared to the placebo group.

One aspect of the present invention is a pharmaceutical combination, said combination comprising
(a) desPro$^{36}$Exendin-4(1-39)-Lys$_6$-NH$_2$ or/and a pharmaceutically acceptable salt thereof, and
(b) a glitazone or/and a pharmaceutically acceptable salt thereof.

The combination of the present invention can be used for the treatment of diabetes type 2 patients, or/and for the treatment of conditions associated with diabetes type 2. Such conditions include a decrease of glucose tolerance, an increased postprandial plasma glucose concentration, an increase in fasting plasma glucose concentration, an increased HbA$_{1c}$ value, or/and an increased fasting plasma insulin concentration.

A preferred aspect of the present invention is a pharmaceutical combination for use in glycemic control in diabetes type 2 patients, said combination comprising
(a) desPro$^{36}$Exendin-4(1-39)-Lys$_6$-NH$_2$ or/and a pharmaceutically acceptable salt thereof, and
(b) a glitazone or/and a pharmaceutically acceptable salt thereof.

As demonstrated by the Example of the present invention, the combination as described herein can be used for improving glycemic control. In the present invention, "improvement of glycemic control" or "glycemic control" in particular refers to improvement of glucose tolerance, improvement of postprandial plasma glucose concentration, improvement of fasting plasma glucose concentration, improvement of the HbA$_{1c}$ value or/and improvement of fasting plasma insulin concentration.

In particular, improvement of glucose tolerance includes improvement of the postprandial plasma glucose concentration or/and improvement of fasting plasma insulin concentration. More particular, improvement of glucose tolerance includes improvement of the postprandial plasma glucose concentration.

In particular, improvement of postprandial plasma glucose concentration is reduction of the postprandial plasma glucose concentration. Reduction means in particular that the plasma glucose concentration reaches normoglycemic values or at least approaches these values.

In particular, improvement of fasting plasma glucose concentration is reduction of the fasting plasma glucose concentration. Reduction means in particular that the plasma glucose concentration reaches normoglycemic values or at least approaches these values.

In particular, improvement of the $HbA_{1c}$ value is reduction of the $HbA_{1c}$ value. Reduction of the $HbA_{1c}$ value in particular means that the $HbA_{1c}$ value is reduced below 6.5% or 7%, for example after treatment for at least one month, at least two months, at least three months, at least four months, at least five months, at least six months or at least one year.

In particular, improvement of fasting plasma insulin concentration is reduction of fasting plasma insulin concentration. The plasma insulin concentration is coupled to the plasma glucose concentration. Under treatment as described herein, in fasting condition the plasma insulin may reach or at least approach values to ensure the continuous supply of glucose to insulin-sensitive organs and tissues or/and to keep the hepatic glucose production at a low level at night. At fasting conditions, the insulin concentration may reach or at least approach values associated with normoglycemia or plasma glucose concentration approaching normoglycemia.

In the context of the present invention, "glitazone", as used herein, includes pharmaceutically acceptable salts thereof. The glitazone may be selected from pioglitazone, troglitazone, rosiglitazone, and pharmaceutically acceptable salts thereof.

In the present invention, the glitazone, in particular pioglitazone, may be administered orally. The skilled person knows formulations of the glitazone, in particular pioglitazone, suitable for treatment of diabetes type 2 by oral administration. Pioglitazone may be administered to a patient in need thereof, in an amount sufficient to induce a therapeutic effect. The glitazone, in particular pioglitazone, may be administered in a dose of at least 10 mg/day, at least 20 mg/day, at least 30 mg/day, or at least 40 mg/day. The maximal daily dose of the glitazone, in particular pioglitazone, may be 50 mg/day or 60 mg/day. A preferred dosing range is 10 mg/day to 50 mg/day or 30 mg/day to 40 mg/day. A more preferred dose is about 30 mg/day. For oral administration, the glitazone, in particular pioglitazone, may be formulated in a solid dosage form, such as a tablet or pill. The glitazone, in particular pioglitazone, may be formulated with suitable pharmaceutically acceptable carriers, adjuvants, or/and auxiliary substances.

The pharmaceutical combination of the present invention may further comprise metformin or/and a pharmaceutically acceptable salt thereof. Metformin is the international non-proprietary name of 1,1-dimethylbiguanide (CAS Number 657-24-9). In the present invention, the term "metformin" includes any pharmaceutically acceptable salt thereof.

In the present invention, metformin may be administered orally. The skilled person knows formulations of metformin suitable for treatment of diabetes type 2 by oral administration. Metformin may be administered to a patient in need thereof, in an amount sufficient to induce a therapeutic effect. Metformin may be administered in a dose of at least 1.0 g/day or at least 1.5 g/day. For oral administration, metformin may be formulated in a solid dosage form, such as a tablet or pill. Metformin may be formulated with suitable pharmaceutically acceptable carriers, adjuvants, or/and auxiliary substances.

If metformin is present in the combination of the present invention, metformin and the glitazone, in particular pioglitazone, may be provided in one formulation, for example in a solid dosage form, such as a tablet or pill. Metformin and the glitazone, in particular pioglitazone, may be formulated with suitable pharmaceutically acceptable carriers, adjuvants, or/and auxiliary substances.

In the present invention, desPro$^{36}$Exendin-4(1-39)-Lys$_6$-NH$_2$ or/and a pharmaceutically acceptable salt may be administered in an add-on therapy to administration of the glitazone, in particular pioglitazone.

In the present invention, the terms "add-on", "add-on treatment", "add-on therapy" and "on top of" relate to treatment of diabetes mellitus type 2 with the glitazone, in particular pioglitazone, and lixisenatide. Also included may be the treatment with metformin, as disclosed herein. The glitazone, in particular pioglitazone, and lixisenatide may be administered within a time interval of 24 h. The glitazone, in particular pioglitazone, and lixisenatide each may be administered in a once-a-day-dosage. The glitazone, in particular pioglitazone, and lixisenatide may be administered by different administration routes. The glitazone, in particular pioglitazone, may be administered orally, and lixisenatide may be administered parenterally.

The patient to be treated by the medicament of the present invention may be a patient suffering from diabetes type 2. The Example demonstrates in these patients, that administration of lixisenatide in combination with the glitazone, in particular pioglitazone, provides an advantageous therapy.

The patient to be treated by the medicament of the present invention suffering from diabetes type 2 may be a patient suffering from diabetes type 2, wherein diabetes type 2 is not adequately controlled by treatment with the glitazone, in particular pioglitazone, alone, for instance with a dose selected from the range of 10 mg/day to 50 mg/day, in particular about 30 mg/day, for at least 2 or at least 3 months. In the present invention, a patient the diabetes type 2 of which is not adequately controlled may have a HbA1c value in the range of 7% to 10%.

The patient to be treated by the medicament of the present invention suffering from diabetes type 2 may be an obese patient. In the present invention, an obese patient may have a body mass index of at least 30 kg/m$^2$.

The patient to be treated by the medicament of the present invention suffering from diabetes type 2 may have a normal body weight. In the present invention, a patient having normal body weight may have a body mass index in the range of 17 kg/m$^2$ to 25 kg/m$^2$, 17 kg/m$^2$ to <30 kg/m$^2$ or <30 kg/m$^2$.

The patient to be treated by the medicament of the present invention may be an adult patient. The patient may have an age of at least 18 years of may have an age in the range of 18 to 80 years, of 18 to 50 years, or 40 to 80 years, or 50 to 60 years. The patient may be younger than 50 years.

The patient to be treated by the medicament of the present invention preferably does not receive an antidiabetic treatment, for instance by insulin or/and related compounds.

The patient to be treated by the medicament of the present invention may suffer from diabetes mellitus type 2 for at least 1 year or at least 2 years. In particular, in the diabetes type 2 patient, diabetes mellitus type 2 has been diagnosed at least 1 year or at least 2 years before onset of therapy by the medicament of the present invention.

The diabetes type 2 patient may have a $HbA_{1c}$ value of at least about 8% or at least about 7.5%. The patient may also have a $HbA_{1c}$ value of about 7% to about 10%. The example of the present invention demonstrates that treatment by lixisenatide results in a reduction of the $HbA_{1c}$ value in diabetes type 2 patients.

In yet another aspect of the present invention, the combination as described herein can be used for improving the $HbA_{1c}$ value in a patient suffering from diabetes type 2, as described herein.

In yet another aspect of the present invention, the combination as described herein can be used for improving glucose tolerance in a patient suffering from diabetes type 2, as described herein.

In yet another aspect of the present invention, the combination as described herein can be used for improving postprandial plasma glucose concentration in a patient suffering from diabetes type 2, as described herein.

In yet another aspect of the present invention, the combination as described herein can be used for improving fasting plasma glucose concentration in a patient suffering from diabetes type 2, as described herein.

In yet another aspect of the present invention, the combination as described herein can be used for improving fasting plasma insulin concentration in a patient suffering from diabetes type 2, as described herein.

In the present invention, normoglycemic values are blood glucose concentrations of in particular 60-140 mg/dl (corresponding to 3.3 bis 7.8 mM/L). This range refers in particular to blood glucose concentrations under fasting conditions or/and postprandial conditions.

The diabetes type 2 patient may have a 2 hours postprandial plasma glucose concentration of at least 10 mmol/L, at least 12 mmol/L, or at least 14 mmol/L. These plasma glucose concentrations exceed normoglycemic concentrations.

The diabetes type 2 patient may have a glucose excursion of at least 2 mmol/L, at least 3 mmol/L, at least 4 mmol/L or at least 5 mmol/L. In the present invention, the glucose excursion is in particular the difference of the 2 hours postprandial plasma glucose concentration and the plasma glucose concentration 30 minutes prior to a meal test.

"Postprandial" is a term that is well known to a person skilled in the art of diabetology. The term "postprandial" describes in particular the phase after a meal or/and exposure to glucose under experimental conditions. In a healthy person this phase is characterised by an increase and subsequent decrease in blood glucose concentration. The term "postprandial" or "postprandial phase" typically ends up to 2 h after a meal or/and exposure to glucose.

The diabetes type 2 patient as disclosed herein may have a fasting plasma glucose concentration of at least 8 mmol/L, at least 8.5 mmol/L or at least 9 mmol/L. These plasma glucose concentrations exceed normoglycemic concentrations.

In the present invention, $desPro^{36}Exendin-4(1-39)-Lys_6-NH_2$ or/and the pharmaceutically acceptable salt thereof may be administered to a patient in need thereof, in an amount sufficient to induce a therapeutic effect.

In the present invention, $desPro^{36}Exendin-4(1-39)-Lys_6-NH_2$ or/and the pharmaceutically acceptable salt thereof may be formulated with suitable pharmaceutically acceptable carriers, adjuvants, or/and auxiliary substances.

The compound $desPro^{36}Exendin-4(1-39)-Lys_6-NH_2$ or/and a pharmaceutically acceptable salt thereof may be administered parenterally, e.g. by injection (such as by intramuscular or by subcutaneous injection). Suitable injection devices, for instance the so-called "pens" comprising a cartridge comprising the active ingredient, and an injection needle, are known. The compound $desPro^{36}Exendin-4(1-39)-Lys_6-NH_2$ or/and a pharmaceutically acceptable salt thereof may be administered in a suitable amount, for instance in an amount in the range of 10 to 15 μg per dose or 15 to 20 μg per dose.

In the present invention, $desPro^{36}Exendin-4(1-39)-Lys_6-NH_2$ or/and a pharmaceutically acceptable salt thereof may be administered in a daily dose in the range of 10 to 20 μg, in the range of 10 to 15 μg, or in the range of 15 to 20 μg. $DesPro^{36}Exendin-4(1-39)-Lys_6-NH_2$ or/and a pharmaceutically acceptable salt thereof may be administered by one injection per day.

In the present invention, $desPro^{36}Exendin-4(1-39)-Lys_6-NH_2$ or/and a pharmaceutically acceptable salt thereof may be provided in a liquid composition. The skilled person knows liquid compositions of lixisenatide suitable for parenteral administration. A liquid composition of the present invention may have an acidic or a physiologic pH. An acidic pH preferably is in the range of pH 1-6.8, pH 3.5-6.8, or pH 3.5-5. A physiologic pH preferably is in the range of pH 2.5-8.5, pH 4.0-8.5, or pH 6.0-8.5. The pH may be adjusted by a pharmaceutically acceptable diluted acid (typically HCl) or pharmaceutically acceptable diluted base (typically NaOH).

The liquid composition comprising $desPro^{36}Exendin-4(1-39)-Lys_6-NH_2$ or/and a pharmaceutically acceptable salt thereof may comprise a suitable preservative. A suitable preservative may be selected from phenol, m-cresol, benzyl alcohol and p-hydroxybenzoic acid ester. A preferred preservative is m-cresol.

The liquid composition comprising $desPro^{36}Exendin-4(1-39)-Lys_6-NH_2$ or/and a pharmaceutically acceptable salt thereof may comprise methionine from 0.5 μg/mL to 20 μg/mL, preferably from 1 μg/ml to 5 μg/ml. Preferably, the liquid composition comprises L-methionine.

Yet another aspect of the present invention refers to a method of treatment of a medical indication, as described herein. For example, the method may comprise the administration of the combination as described herein. The method may be a method of treatment of diabetes type 2 patients, or/and of treatment of conditions associated with diabetes type 2, as described herein. The patient may be a patient as defined herein.

A further aspect of the present invention is a method for improvement of glycemic control in diabetes type 2 patients, said method comprising administering $desPro^{36}Exendin-4(1-39)-Lys_6-NH_2$ or/and a pharmaceutically acceptable salt thereof, in combination with a glitazone, in particular pioglitazone, to a patient in need thereof. In particular, the combination as described herein may be administered. In the method of the present invention, the patient may be the patient defined herein.

Yet another aspect of the present invention refers to the use of the combination as described herein for the manufacture of a medicament for the treatment of a medical indication, as described herein. For example, the combination of the present invention can be used for the manufacture of a medicament for the treatment of diabetes type 2 patients, or/and for the treatment of conditions associated with diabetes type 2. In particular, the combination of the present invention can be used for the manufacture of a medicament for the improvement of glycemic control, improvement of glucose tolerance, improvement of postprandial plasma glucose concentration, improvement of fasting plasma glucose concentration, improvement of the $HbA_{1c}$ value or/and improvement of fasting plasma insulin concentration. The patient may be a patient as defined herein.

The invention is further illustrated by the following example and figures.

EXAMPLE

Summary

Figure 1:
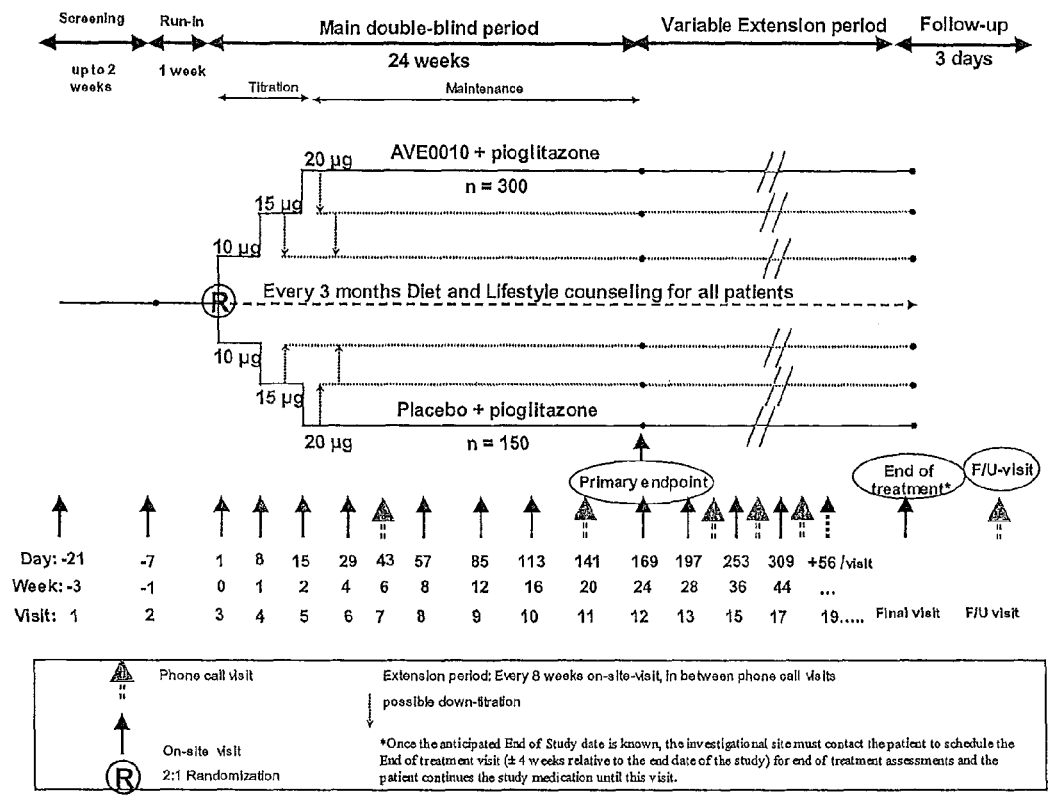
FIG. 1—Study design.

The Example refers to a randomized, double-blind, placebo-controlled, 2-arm, unbalanced design, parallel-group, multicenter, multinational study assessing the efficacy and safety of lixisenatide on top of pioglitazone in patients with type 2 diabetes, not adequately controlled with pioglitazone. The approximate minimum double-blind study duration per patient was 79 weeks (up to 2 weeks screening+1 week run-in +24 weeks main double-blind treatment+variable extension+3 days follow-up).

The study was conducted in 150 centers in 13 countries. The primary objective of the study was to assess the efficacy of lixisenatide on glycemic control in comparison to placebo as an add-on treatment to pioglitazone in teens of HbA1c reduction (absolute change) over a period of 24 weeks.

A total of 484 patients were randomized to one of two treatment groups (323 in lixisenatide and 161 in placebo). All randomized patients were exposed to the study treatment. Demographics and baseline characteristics were generally similar across the treatment groups. Five patients (3 on lixisenatide and 2 on placebo) were excluded from the modified intent-to-treat (mITT) population for efficacy analyses due to no post-baseline efficacy data. During the overall study treatment period, 136 (28.1%) patients prematurely discontinued the study treatment (26.0% for lixisenatide and 32.3% for placebo). For the lixisenatide group, the main reason for treatment discontinuation was "other reasons" (10.5% versus 12.4% for placebo) followed by "adverse events" (9.0% versus 8.7% for placebo).

Efficacy analyses are based on the main 24-week double-blind treatment period. The least squares (LS) mean changes from baseline to Week 24 in HbA1c were −0.90% in the lixisenatide group and −0.34% in the placebo group (LS mean difference vs. placebo=−0.56%; p-value <0.0001). The percentages of patients reaching HbA1c≤6.5% or ≤7% at Week 24 were significantly higher in the lixisenatide group than in the placebo group (for HbA1c ≤6.5%, 28.9% in the lixisenatide group versus 10.1% in the placebo group; for HbA1c ≤7%, 52.3% in the lixisenatide group versus 26.4% in the placebo group). The HbA1c responder analysis (HbA1c ≤6.5% or ≤7% at Week 24) using Cochran-Mantel-Haenszel (CMH) method also showed a significant treatment difference between lixisenatide and placebo at Week 24 (p-value <0.0001).

For fasting plasma glucose (FPG), a significant decrease from baseline to Week 24 was observed in the lixisenatide group compared to the placebo group (LS mean difference versus placebo=−0.84 mmol/L; p-value<0.0001). For body weight, the LS mean decrease was 0.21 kg from baseline at Week 24 in the lixisenatide group, compared to a LS mean increase of 0.21 kg in the placebo group, and the difference between the 2 groups was not significant (LS mean difference versus placebo=−0.41 kg). Per the testing strategy for multiplicity adjustment, the inferential testing for the subsequent efficacy variables was exploratory, since the body weight analysis failed to show a statistically significant difference. There is no relevant difference observed in β-cell function assessed by HOMA-β between lixisenatide and placebo with LS mean difference of −0.25 (95% CI: [−6.579 to 6.070]). The percentage of patients requiring rescue therapy at Week 24 was substantially lower in the lixisenatide group (12 patients [3.8%]), compared to the placebo group (18 [11.3%]). For fasting plasma insulin (FPI), the LS mean reduction was greater in the lixisenatide group than in the placebo group with LS mean difference of −9.36 pmol/L (95% CI: [−16.586 to −2.124]).

Safety analyses are based on the treatment period of the whole study. Lixisenatide was well tolerated. The proportions of patients who experienced treatment emergent adverse events (TEAEs) were 87.9% in the lixisenatide group and 83.2% in the placebo group. No patients in the lixisenatide group died, but 2 patients in the placebo group died. One had a treatment emergent acute myocardial infarction leading to death and the other died due to a post-treatment AE (end stage debility) following respiratory failure with multiorgan failure. The percentage of patients who had serious TEAEs was lower in the lixisenatide group (7.4%) than in the placebo group (9.3%). The most commonly reported TEAEs in the lixisenatide group were nausea (26% versus 13.7% for placebo), followed by nasopharyngitis (16.4% versus 14.9% for placebo) and headache (13.3% versus 11.8% for placebo). During the on-treatment period of the whole study, 23 (7.1%) patients in the lixisenatide group had symptomatic hypoglycemia per protocol definition, compared to 7 (4.3%) in the placebo group. None of the symptomatic hypoglycemia events were severe in intensity. Twenty-two (6.8%) patients in the lixisenatide group and 8 (5.0%) in the placebo group experienced injection site reaction AEs. A total of 12 patients (9 [2.8%] patients in the lixisenatide group and 3 [1.9%] in the placebo group) reported 19 events that were adjudicated as allergic reactions by the Allergic Reaction Assessment Committee (ARAC). Of these, 5 events in 3 patients in the lixisenatide group (1 patient with allergic dermatitis, 1 with urticaria, and 1 with angioedema, anaphylactic reaction, and allergic conjunctivitis) were adjudicated as possibly related to IP. No events were adjudicated as possibly related to IP in the placebo group. No case of pancreatitis or thyroid cancer was reported in the study.

1 OBJECTIVES

1.1 Primary Objective

The primary objective of this study was to assess the efficacy of lixisenatide on glycemic control in comparison to placebo as an add-on treatment to pioglitazone in type 2 diabetes patients treated with pioglitazone in terms of absolute HbA1c reduction over a period of 24 weeks.

1.2 Key Secondary Objective(s)

The secondary objectives of this study were:
To assess the effects of lixisenatide on
   Percentage of patients reaching HbA1c<7%,
   Percentage of patients reaching HbA1c≤6.5%,
   Fasting Plasma Glucose (FPG),
   Body weight,
   β-cell function assessed by HOMA-β,
   Fasting plasma insulin (FPI).
To assess lixisenatide safety and tolerability.

2 TRIAL DESIGN

This was an unbalanced (2:1), randomized, double-blind, placebo-controlled, 2-arm parallel-group, multicenter, multinational study with an variable extension period comparing lixisenatide treatment with placebo in type 2 diabetes patients (300 patients in lixisenatide arm and 150 patients in placebo arm). The study was double-blind with regard to active and placebo treatments. The study drug volume (i.e. dose of active drug or matching placebo) was not blinded. The patients were stratified by screening values of HbA1c (<8%, 8%) and metformin use (Yes, No) at screening.

The approximate minimum double-blind study duration per patient was 79 weeks (up to 2 weeks screening+1 week run-in +24 weeks main double-blind treatment+variable extension+3 days follow-up). Patients who had completed the 24-week main double-blind period underwent a variable double blind extension period, which ended for all patients approximately at the scheduled date of week 76 visit (V25) for the last randomized patient.

The trial design is illustrated by FIG. 1.

3 PRIMARY AND KEY SECONDARY ENDPOINTS

3.1 Primary Endpoint

The primary efficacy variable was the absolute change in HbA1c from baseline to Week 24, which was defined as: HbA1c value at Week 24—HbA1c value at baseline.

If a patient permanently discontinued the treatment or received rescue therapy during the main 24-week double-blind treatment period or did not have HbA1c value at Week 24, the last post-baseline HbA1c measurement during the main 24-week double-blind on-treatment period was used as HbA1c value at Week 24 (last observation carried forward [LOCF] procedure).

3.2 Key Secondary Endpoints

3.2.1 Key Secondary Efficacy Endpoints

For secondary efficacy variables, the same procedure for handling missing assessments/early discontinuation was applied as for the primary efficacy variable.

Continuous Variables:
   Change in FPG (mmol/L) from baseline to Week 24,
   Change in body weight (kg) from baseline to Week 24,
   Change in β-cell function assessed by HOMA-β from baseline to Week 24,
   Change in FPI (pmol/L) from baseline to Week 24.
Categorical Variables:
   Percentage of patients with HbA1c<7% at Week 24,
   Percentage of patients with HbA1c≤6.5% at Week 24,
   Percentage of patients requiring rescue therapy during the main 24-week double-blind treatment period,
   Percentage of patients with 5% weight loss (kg) from baseline at Week 24.

3.2.2 Safety Endpoints

The safety analysis was based on the reported TEAEs and other safety information including symptomatic hypoglycemia and severe symptomatic hypoglycemia, local tolerability at injection site, allergic events (as adjudicated by ARAC), suspected pancreatitis, increased calcitonin, vital signs, 12-lead ECG and laboratory tests.

Major cardiovascular events were also collected and adjudicated in a blinded manner by a Cardiovascular events Adjudication Committee (CAC). The adjudicated and confirmed events by CAC from this study and other lixisenatide phase 3 studies will be pooled for analyses and summarized in a separate report based on the statistical analysis plan for the overall cardiovascular assessment of lixisenatide. The KRM/CSR will not present the summary of the adjudicated and confirmed CV events from this study.

4 SAMPLE SIZE CALCULATION ASSUMPTIONS

The sample size/power calculations were performed based on the primary variable, absolute change from baseline to Week 24 in HbA1c.

Three-hundred (300) patients in the lixisenatide treatment and 150 in the placebo treatment arm provided a power of 96% (or 86%) to detect differences of 0.5% (or 0.4%) in the absolute change from baseline to Week 24 in HbA1c between the lixisenatide group and the placebo group. This calculation assumed a common standard deviation of 1.3% with a 2-sided test at the 5% significance level. The sample size calculations were based upon the 2-sample t-test and made using nQuery Advisor® 5.0. Standard deviation was estimated in a conservative manner from previously conducted diabetes studies (based on published data of similarly designed study and on internal data, not published), taking into account early drop-out.

5 STATISTICAL METHODS

5.1 Analysis Populations

The modified intent-to-treat (mITT) population consisted of all randomized patients who received at least 1 dose of double-blind investigational product (IP), and had both a baseline assessment and at least 1 post-baseline assessment of efficacy variables.

The safety population was defined as all randomized patients who took at least one dose of the double-blind IP.

5.2 Primary Efficacy Analysis

The primary efficacy variable (change in HbA1c from baseline to Week 24) was analyzed using an analysis of covariance (ANCOVA) model with treatment groups (lixisenatide and placebo), randomization strata of screening HbA1c (<8.0, ≥8.0%), randomization strata of metformin use (Yes, No) at screening, and country as fixed effects and the baseline HbA1c value as a covariate.

Both means and adjusted means for lixisenatide and placebo were provided, as well as 95% confidence intervals (CI) constructed for adjusted mean differences between lixisenatide and placebo. Difference between lixisenatide and placebo and two-sided 95% confidence interval, as wells as p-value were estimated within the framework of ANCOVA.

The primary analysis of the primary efficacy variable was performed based on the mITT population and the measurements obtained during the main 24-week double-blind on-treatment period for efficacy variables. The main 24-week double-blind on-treatment period for efficacy analysis was the time from the first dose of the double-blind IP up to 3 days (except for FPG and FPI, which was up to 1 day) after the last dose of the double-blind IP injection on or before V12/Week 24 visit (or D169 if V12/Week 24 visit is missing), or up to the introduction of the rescue therapy, whichever the earliest. The LOCF procedure was used by taking this last available post-baseline on-treatment $HbA_{1c}$ measurement (before the introduction of rescue therapy) as the $HbA_{1c}$ value at Week 24.

5.3 Key Secondary Efficacy Analysis

A step down testing procedure was applied in order to ensure the control of type 1 error. Once the primary variable was statistically significant at $\alpha=0.05$, the testing procedure was performed to test the following secondary efficacy variables by the following prioritized order. The tests stop as soon as an endpoint was found not statistically significant at $\alpha=0.05$.

Change in FPG (Eamon) from baseline to Week 24,
Change in body weight (kg) from baseline to Week 24,
Change in β-cell function assessed by HOMA-β from baseline to Week 24,
Percentage of patients requiring rescue therapy during the 24-week treatment period,
Change in FPI (mmol/L) from baseline to Week 24.

All continuous secondary efficacy variables at Week 24 as described in Section 3.2.1 were analyzed using the similar approach and ANCOVA model as described in Section 5.2 for the primary analysis of the primary efficacy endpoint. The adjusted estimates of the treatment mean difference between lixisenatide and placebo and two-sided 95% confidence intervals were provided.

The following categorical secondary efficacy variables at Week 24 were analyzed using a Cochran-Mantel-Haenszel (CMH) method stratified on randomization strata (screening HbA1c [<8.0, ≥8.0%] and screening metformin use [Yes, No]):

Percentage of patients with HbA1c <7.0% at Week 24,
Percentage of patients with HbA1c ≤6.5% at Week 24,
Percentage of patients requiring rescue therapy during the main 24-week double-blind treatment period.

Number and percentage of patients with ≥5% weight loss from baseline at Week 24 were presented by treatment groups.

Results for all efficacy endpoints during the variable extension period and at the end of treatment were to be evaluated by descriptive statistics only.

5.4 Safety Analysis

The safety analyses were primarily based on the on-treatment period of the whole study. The on-treatment period of the whole study was defined as the time from the first dose of double-blind IP up to 3 days after the last dose of IP administration during the whole study period regardless of rescue status. The 3-day interval was chosen based on the half-life of the IP (approximately 5 times the half-life).

In addition, the safety analyses for the 24-week double-blind treatment period will be summarized in the CSR.

The summary of safety results (descriptive statistics or frequency tables) is presented by treatment groups.

6 RESULTS

6.1 Study Patients

6.1.1 Patient Accountability

The study was conducted in 150 centers in 13 countries (Austria, Canada, France, Germany, Greece, Guatemala, India, Mexico, Peru, Puerto Rico, Romania, Turkey, and United States of America). A total of 906 patients were screened and 484 were randomized to 1 of the 2 treatment groups. The most common reason for non-randomization was HbA1c value out of range at the screening visit as defined per protocol (283 [31.2%] out of 906 screened patients).

All 484 randomized patients were exposed to the study treatment and 5 patients (3 in the lixisenatide group and 2 in the placebo group) were excluded from mITT population for efficacy analyses due to no post-baseline efficacy data. Table 1 provides the number of patients included in each analysis population.

Due to his investigator's non-compliance to the clinical protocol and violation of good clinical practices, one patient in the lixisenatide group was discontinued by the sponsor. The patient was exposed for 113 days and included in the analyses for safety and efficacy.

TABLE 1

Analysis populations - Randomized population

|  | Placebo (N = 161) | Lixisenatide (N = 323) | All (N = 484) |
|---|---|---|---|
| Randomized population Efficacy population | 161 (100%) | 323 (100%) | 484 (100%) |
| Modified Intent-to-Treat (mITT) | 159 (98.8%) | 320 (99.1%) | 479 (99.0%) |
| Safety population | 161 | 323 | 484 |

Note:
The safety patients are tabulated according to treatment actually received (as treated).
For the efficacy population, patients are tabulated according to their randomized treatment (as randomized).

6.1.2 Study Disposition

Table 2 provides the summary of patient disposition for each treatment group. During the overall treatment period, 136 (28.1%) patients prematurely discontinued the study treatment (26.0% for lixisenatide and 32.3% for placebo). In the lixisenatide group, the main reason for treatment discontinuation was "other reasons" (10.5% versus 12.4% for placebo) followed by "adverse events" (9.0% versus 8.7% for placebo).

Figure 2:
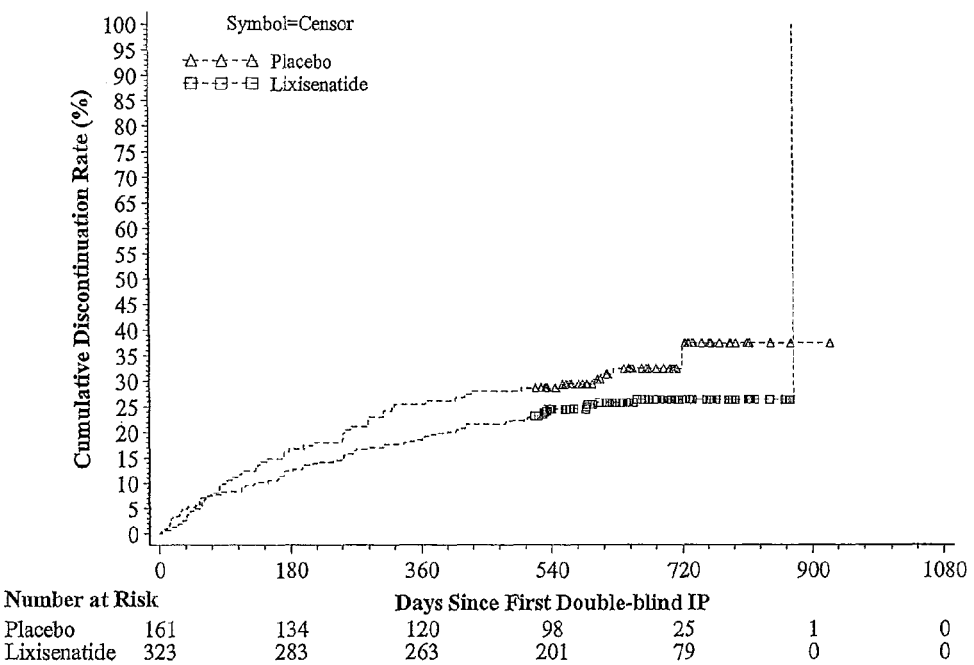
FIG. 2—Kaplan-Meier plot of time to treatment discontinuation due to any reason—Randomized population.

Similar results were observed for the 24-week treatment period, where a total of 59 (12.2%) patients prematurely discontinued the study treatment (10.8% for lixisenatide and 14.9% for placebo) with main reasons in the lixisenatide group also being "other reasons" (4.0% versus 5.0% for placebo) and "adverse events" (4.0% versus 5.6% for placebo). The category of "other reasons" were confirmed by investigators to be not AE related, and included but was not limited to personal reasons, schedule conflict, moving, injection not convenient, site closure etc. The time-to-onset of treatment discontinuation due to any reason for the overall treatment period is depicted in FIG. 2. A lower rate of discontinuation was observed in the lixisenatide group during the whole treatment period, as compared to the placebo group. The increase of the rate of discontinuation from around 25 to 100% in the lixisenatide group at the end of the study was due to the patient who had been followed the longest, discontinued at Day 874.

One patient in the lixisenatide group who discontinued treatment due to "Glycosylated haemoglobin increased" in Table 20 was counted as lack of efficacy in Table 2, while 2 patients in the placebo group who discontinued for AE were not counted in Table 20 because their AEs leading to treatment discontinuation occurred during the pre- or post-treatment period.

TABLE 2

Patient disposition - Randomized population

| | Placebo (N = 161) | Lixisenatide (N = 323) |
|---|---|---|
| Randomized and treated | 161 (100%) | 323 (100%) |
| Did not complete 24-week double-blind study treatment | 24 (14.9%) | 35 (10.8%) |
| Subject's request for 24-week treatment discontinuation | 20 (12.4%) | 26 (8.0%) |
| Reason for 24-week study treatment discontinuation | 24 (14.9%) | 35 (10.8%) |
| Adverse event | 9 (5.6%) | 13 (4.0%) |
| Lack of efficacy | 5 (3.1%) | 2 (0.6%) |
| Poor compliance to protocol | 1 (0.6%) | 4 (1.2%) |
| Lost to follow-up | 1 (0.6%) | 3 (0.9%) |
| Other reasons | 8 (5.0%) | 13 (4.0%) |
| Did not complete double-blind study treatment | 52 (32.3%) | 84 (26.0%) |
| Subject's request for treatment discontinuation | 42 (26.1%) | 65 (20.1%) |
| Reason for study treatment discontinuation | 52 (32.3%) | 84 (26.0%) |
| Adverse event | 14 (8.7%) | 29 (9.0%) |
| Lack of efficacy | 10 (6.2%) | 11 (3.4%) |
| Poor compliance to protocol | 6 (3.7%) | 6 (1.9%) |
| Lost to follow-up | 2 (1.2%) | 4 (1.2%) |
| Other reasons | 20 (12.4%) | 34 (10.5%) |
| Status at last study contact | 161 (100%) | 323 (100%) |
| Alive | 155 (96.3%) | 318 (98.5%) |
| Dead | 2 (1.2%) | 0 |
| Lost to follow-up | 4 (2.5%) | 5 (1.5%) |

Note:
Percentages are calculated using the number of randomized patients as denominator.

6.1.3 Demographics and Baseline Characteristics

The demographic and patient baseline characteristics were generally similar across treatment groups for the safety population (Table 3). The median age was 56 years and 52.5% were male. The study population was primarily Caucasian (83.7%) and 67.6% of the safety population had a BMI ≥30 kg/m$^2$.

Disease characteristics including diabetic history were generally comparable between two treatment groups (Table 4). The median duration of diabetes was 7.22 years and the median age at onset of diabetes was 48 years. Patients were on pioglitazone for a median duration of 0.83 years and the median daily dose was 30 mg. At screening, 81% of patients had used metformin with a median duration of 3.37 years and a median daily dose of 2000 mg.

HbA1c, FPG and HOMA-β at baseline were generally comparable across treatment groups for the safety population (Table 5). A higher mean body weight at baseline was observed in the placebo group (96.74 kg) compared to the lixisenatide group (92.93 kg). Both the mean and the median of FPI are higher in the placebo group (66.07 pmol/L and 53.78 pmol/L, respectively) compared to the lixisenatide group (63.32 pmol/L and 46.14 pmol/L, respectively). The average HbA1c at baseline was 8.07%.

TABLE 3

Demographics and patient characteristics at screening or baseline - Safety population

| | Placebo (N = 161) | Lixisenatide (N = 323) | All (N = 484) |
|---|---|---|---|
| Age (years) | | | |
| Number | 161 | 323 | 484 |
| Mean (SD) | 55.3 (9.5) | 56.0 (9.5) | 55.8 (9.5) |
| Median | 55.0 | 56.0 | 56.0 |
| Min:Max | 28:77 | 26:82 | 26:82 |
| Age group (years) [n (%)] | | | |
| Number | 161 | 323 | 484 |
| <50 | 41 (25.5%) | 66 (20.4%) | 107 (22.1%) |
| >=50 to <65 | 90 (55.9%) | 199 (61.6%) | 289 (59.7%) |
| >=65 to <75 | 29 (18.0%) | 49 (15.2%) | 78 (16.1%) |
| >=75 | 1 (0.6%) | 9 (2.8%) | 10 (2.1%) |
| Gender [n (%)] | | | |
| Number | 161 | 323 | 484 |
| Male | 82 (50.9%) | 172 (53.3%) | 254 (52.5%) |
| Female | 79 (49.1%) | 151 (46.7%) | 230 (47.5%) |
| Race [n (%)] | | | |
| Number | 161 | 323 | 484 |
| Caucasian/White | 132 (82.0%) | 273 (84.5%) | 405 (83.7%) |
| Black | 9 (5.6%) | 14 (4.3%) | 23 (4.8%) |
| Asian/Oriental | 8 (5.0%) | 14 (4.3%) | 22 (4.5%) |
| Other | 12 (7.5%) | 22 (6.8%) | 34 (7.0%) |
| Ethnicity [n (%)] | | | |
| Number | 161 | 323 | 484 |
| Hispanic | 41 (25.5%) | 87 (26.9%) | 128 (26.4%) |
| Not Hispanic | 120 (74.5%) | 236 (73.1%) | 356 (73.6%) |
| Screening HbA1c (%) | | | |
| Number | 161 | 322 | 483 |
| Mean (SD) | 8.15 (0.82) | 8.15 (0.82) | 8.15 (0.82) |
| Median | 8.00 | 8.00 | 8.00 |
| Min:Max | 7.0:10.0 | 7.0:10.0 | 7.0:10.0 |
| Randomization strata of screening | | | |

TABLE 3-continued

Demographics and patient characteristics at screening or baseline - Safety population

| | Placebo (N = 161) | Lixisenatide (N = 323) | All (N = 484) |
|---|---|---|---|
| HbA1c (%) [n (%)] | | | |
| Number | 161 | 323 | 484 |
| <8 | 79 (49.1%) | 159 (49.2%) | 238 (49.2%) |
| ≥8 | 82 (50.9%) | 164 (50.8%) | 246 (50.8%) |
| Randomization strata of metformin use at screening [n (%)] | | | |
| Number | 161 | 323 | 484 |
| Yes | 132 (82.0%) | 264 (81.7%) | 396 (81.8%) |
| No | 29 (18.0%) | 59 (18.3%) | 88 (18.2%) |
| Baseline BMI (kg/m$^2$) | | | |
| Number | 161 | 323 | 484 |
| Mean (SD) | 34.44 (7.04) | 33.66 (6.71) | 33.92 (6.82) |
| Median | 33.69 | 33.59 | 33.62 |
| Min:Max | 21.7:52.8 | 20.2:62.7 | 20.2:62.7 |
| Baseline BMI Group (kg/m$^2$) [n (%)] | | | |
| Number | 161 | 323 | 484 |
| <30 | 51 (31.7%) | 106 (32.8%) | 157 (32.4%) |
| ≥30 | 110 (68.3%) | 217 (67.2%) | 327 (67.6%) |

BMI = Body Mass Index.

TABLE 4

Disease characteristics at screening or baseline - Safety population

| | Placebo (N = 161) | Lixisenatide (N = 323) | All (N = 484) |
|---|---|---|---|
| Duration of diabetes (years) | | | |
| Number | 161 | 323 | 484 |
| Mean (SD) | 8.09 (5.58) | 8.11 (5.44) | 8.10 (5.48) |
| Median | 7.27 | 7.18 | 7.22 |
| Min:Max | 1.0:30.4 | 0.9:32.1 | 0.9:32.1 |
| Age at onset of type 2 diabetes (years) | | | |
| Number | 161 | 323 | 484 |
| Mean (SD) | 47.22 (9.41) | 47.84 (8.88) | 47.63 (9.05) |
| Median | 48.00 | 48.00 | 48.00 |
| Min:Max | 21.0:69.0 | 20.0:74.0 | 20.0:74.0 |
| Duration of pioglitazone treatment (years) | | | |
| Number | 161 | 323 | 484 |
| Mean (SD) | 1.79 (2.51) | 1.69 (2.00) | 1.72 (2.18) |
| Median | 0.77 | 0.87 | 0.83 |
| Min:Max | 0.2:18.3 | 0.2:11.2 | 0.2:18.3 |
| Daily dose of pioglitazone (mg) at baseline | | | |
| Number | 161 | 323 | 484 |
| Mean (SD) | 33.26 (6.21) | 33.81 (6.64) | 33.63 (6.50) |
| Median | 30.00 | 30.00 | 30.00 |
| Min:Max | 30.0:45.0 | 30.0:60.0 | 30.0:60.0 |
| Categorized daily dose of pioglitazone at baseline (mg) [n (%)] | | | |
| Number | 161 | 323 | 484 |
| <30 | 0 | 0 | 0 |
| ≥30-<45 | 126 (78.3%) | 242 (74.9%) | 368 (76.0%) |
| ≥45 | 35 (21.7%) | 81 (25.1%) | 116 (24.0%) |
| Metformin use at screening [n (%)] | | | |
| Number | 161 | 323 | 484 |
| Yes | 131 (81.4%) | 261 (80.8%) | 392 (81.0%) |
| No | 30 (18.6%) | 62 (19.2%) | 92 (19.0%) |
| Duration of metformin treatment (years) | | | |
| Number | 131 | 261 | 392 |
| Mean (SD) | 4.27 (3.84) | 4.34 (3.77) | 4.32 (3.79) |
| Median | 3.33 | 3.37 | 3.37 |
| Min:Max | 0.3:20.5 | 0.2:25.8 | 0.2:25.8 |
| Daily dose of metformin at baseline (mg) | | | |
| Number | 131 | 261 | 392 |
| Mean (SD) | 1872.90 (273.25) | 1895.02 (295.24) | 1887.63 (287.92) |
| Median | 1700.00 | 2000.00 | 2000.00 |
| Min:Max | 1500.0:2550.0 | 1500.0:3000.0 | 1500.0:3000.0 |

TABLE 4-continued

Disease characteristics at screening or baseline - Safety population

| | Placebo (N = 161) | Lixisenatide (N = 323) | All (N = 484) |
|---|---|---|---|
| Categorized daily dose of metformin at baseline (mg) [n (%)] | | | |
| Number | 131 | 261 | 392 |
| <1500 | 0 | 0 | 0 |
| ≥1500-<2500 | 119 (90.8%) | 236 (90.4%) | 355 (90.6%) |
| ≥2500-<3000 | 12 (9.2%) | 23 (8.8%) | 35 (8.9%) |
| ≥3000 | 0 | 2 (0.8%) | 2 (0.5%) |
| History of gestational diabetes [n (%)] | | | |
| Number (Female) | 79 | 151 | 230 |
| Yes (Female) | 6 (7.6%) | 15 (9.9%) | 21 (9.1%) |
| No (Female) | 73 (92.4%) | 136 (90.1%) | 209 (90.9%) |
| Prior use of GLP-1 receptor agonist [n (%)] | | | |
| Number | 161 | 323 | 484 |
| Yes | 5 (3.1%) | 17 (5.3%) | 22 (4.5%) |
| No | 156 (96.9%) | 306 (94.7%) | 462 (95.5%) |
| Diabetic retinopathy [n (%)] | | | |
| Number | 160 | 323 | 483 |
| Yes | 5 (3.1%) | 13 (4.0%) | 18 (3.7%) |
| No | 151 (94.4%) | 303 (93.8%) | 454 (94.0%) |
| Unknown | 4 (2.5%) | 7 (2.2%) | 11 (2.3%) |
| Diabetic sensory or motor neuropathy [n (%)] | | | |
| Number | 160 | 323 | 483 |
| Yes | 19 (11.9%) | 69 (21.4%) | 88 (18.2%) |
| No | 140 (87.5%) | 251 (77.7%) | 391 (81.0%) |
| Unknown | 1 (0.6%) | 3 (0.9%) | 4 (0.8%) |
| Diabetic autonomic neuropathy [n (%)] | | | |
| Number | 160 | 323 | 483 |
| Yes | 5 (3.1%) | 3 (0.9%) | 8 (1.7%) |
| No | 155 (96.9%) | 316 (97.8%) | 471 (97.5%) |
| Unknown | 0 | 4 (1.2%) | 4 (0.8%) |
| Diabetic nephropathy [n (%)] | | | |
| Number | 160 | 323 | 483 |
| Yes | 8 (5.0%) | 14 (4.3%) | 22 (4.6%) |
| Microalbuminuria | 5 (3.1%) | 10 (3.1%) | 15 (3.1%) |
| Overt proteinuria | 0 | 1 (0.3%) | 1 (0.2%) |
| Impaired renal function | 0 | 1 (0.3%) | 1 (0.2%) |
| Dialysis or transplantation | 0 | 0 | 0 |
| Unknown | 3 (1.9%) | 2 (0.6%) | 5 (1.0%) |
| No | 148 (92.5%) | 300 (92.9%) | 448 (92.8%) |
| Unknown | 4 (2.5%) | 9 (2.8%) | 13 (2.7%) |
| Categorized microalbumin at randomization [n (%)] | | | |
| Number | 67 | 139 | 206 |
| <3 mg/L (Not reportable) | 9 (13.4%) | 15 (10.8%) | 24 (11.7%) |
| ≥3 mg/L (Reportable) | 58 (86.6%) | 124 (89.2%) | 182 (88.3%) |
| <20 mg/L | 37 (55.2%) | 84 (60.4%) | 121 (58.7%) |
| ≥20-<200 mg/L | 18 (26.9%) | 33 (23.7%) | 51 (24.8%) |
| ≥200 mg/L | 3 (4.5%) | 7 (5.0%) | 10 (4.9%) |
| Creatinine clearance at screening (ml/min) | | | |
| Number | 158 | 309 | 467 |
| Mean (SD) | 136.34 (57.86) | 128.08 (46.51) | 130.88 (50.73) |
| Median | 126.32 | 121.42 | 122.24 |
| Min:Max | 46.7:438.3 | 38.3:349.5 | 38.3:438.3 |
| Categorized creatinine clearance at screening [n (%)] | | | |
| Number | 158 | 309 | 467 |
| <30 ml/min (severe renal impairment) | 0 | 0 | 0 |
| ≥30-<50 ml/min (moderate renal impairment) | 1 (0.6%) | 5 (1.6%) | 6 (1.3%) |
| ≥50-≤80 ml/min (mild renal impairment) | 15 (9.5%) | 28 (9.1%) | 43 (9.2%) |
| >80 ml/min (no renal impairment) | 142 (89.9%) | 276 (89.3%) | 418 (89.5%) |

GLP-1 = Glucagon like peptide-1.
Creatinine clearance value is derived using the equation of Cockcroft and Gault.

TABLE 5

Baseline efficacy variables - Safety population

|  | Placebo (N = 161) | Lixisenatide (N = 323) | All (N = 484) |
|---|---|---|---|
| HbA1c (%) | | | |
| Number | 161 | 323 | 484 |
| Mean (SD) | 8.06 (0.79) | 8.08 (0.90) | 8.07 (0.86) |
| Median | 7.90 | 7.90 | 7.90 |
| Min:Max | 6.5:10.2 | 6.5:12.7 | 6.5:12.7 |
| FPG (mmol/L) | | | |
| Number | 161 | 323 | 484 |
| Mean (SD) | 9.13 (2.20) | 9.11 (2.15) | 9.12 (2.16) |
| Median | 8.70 | 8.80 | 8.80 |
| Min:Max | 4.7:17.9 | 4.5:17.2 | 4.5:17.9 |
| Weight (kg) | | | |
| Number | 161 | 323 | 484 |
| Mean (SD) | 96.74 (25.58) | 92.93 (22.90) | 94.20 (23.87) |
| Median | 92.90 | 92.00 | 92.20 |
| Min:Max | 45.0:198.3 | 48.5:162.7 | 45.0:198.3 |
| FPI (pmol/L) | | | |
| Number | 142 | 300 | 442 |
| Mean (SD) | 66.07 (48.12) | 63.32 (57.69) | 64.21 (54.76) |
| Median | 53.78 | 46.14 | 48.72 |
| Min:Max | 4.9:356.1 | 9.4:635.7 | 4.9:635.7 |
| HOMA-β | | | |
| Number | 141 | 300 | 441 |
| Mean (SD) | 36.23 (26.50) | 34.69 (30.30) | 35.18 (29.12) |
| Median | 29.29 | 26.52 | 27.49 |
| Min:Max | 1.1:157.6 | 3.8:276.3 | 1.1:276.3 |

FPG = Fasting Plasma Glucose; FPI = Fasting Plasma Insulin.

6.1.4 Dosage and Duration

The average treatment exposure was 560.2 days (80 weeks) in the lixisenatide group, compared to 518.6 days (74 weeks) in the placebo group (Table 6). Of 323 lixisenatide treated patients, 286 (88.5%) were exposed to IP for 24 weeks (169 days) or longer, and 199 (61.6%) were exposed for 18 months (547 days) or longer. Five patients did not record the last administration date on CRF page "End of treatment" and hence their duration of exposure was set to missing following the SAP data handling convention.

At the end of double-blind treatment, 92.3% of patients reached the target daily dose of 20 µg in the lixisenatide group, lower than the placebo group (97.5%) (Table 7). Similar result was observed at the end of 24-week double-blind treatment period (92.6% for lixisenatide versus 98.8% for placebo) (Table 8). The dose at the end of titration is presented in Table 28.

TABLE 6

Exposure to investigational product - Safety population

|  | Placebo (N = 161) | Lixisenatide (N = 323) |
|---|---|---|
| Cumulative duration of treatment exposure (patient years) | 225.8 | 490.8 |
| Duration of study treatment (days) | | |
| Number | 159 | 320 |
| Mean (SD) | 518.6 (232.5) | 560.2 (226.2) |
| Median | 588.0 | 615.5 |
| Min:Max | 3:925 | 6:874 |
| Duration of study treatment by category [n (%)] | | |
| Missing duration | 2 (1.2%) | 3 (0.9%) |
| 1-14 days | 1 (0.6%) | 7 (2.2%) |
| 15-28 days | 1 (0.6%) | 6 (1.9%) |
| 29-56 days | 5 (3.1%) | 8 (2.5%) |
| 57-84 days | 7 (4.3%) | 3 (0.9%) |
| 85-168 days | 9 (5.6%) | 10 (3.1%) |
| 169-364 days | 16 (9.9%) | 25 (7.7%) |
| 365-546 days | 23 (14.3%) | 62 (19.2%) |
| 547-728 days | 76 (47.2%) | 126 (39.0%) |
| >728 days | 21 (13.0%) | 73 (22.6%) |
| Cumulative duration of study treatment by category [n (%)] | | |
| Missing duration | 2 (1.2%) | 3 (0.9%) |
| ≥1 day | 159 (98.8%) | 320 (99.1%) |
| ≥15 days | 158 (98.1%) | 313 (96.9%) |
| ≥29 days | 157 (97.5%) | 307 (95.0%) |
| ≥57 days | 152 (94.4%) | 299 (92.6%) |
| ≥85 days | 145 (90.1%) | 296 (91.6%) |
| ≥169 days | 136 (84.5%) | 286 (88.5%) |
| ≥365 days | 120 (74.5%) | 261 (80.8%) |
| ≥547 days | 97 (60.2%) | 199 (61.6%) |
| ≥729 days | 21 (13.0%) | 73 (22.6%) |

Duration of exposure = (date of the last double-blind investigational product injection − date of the first double-blind investigational product injection) + 1.

TABLE 7

Number (%) of patients by final total daily dose at the end of the double-blind treatment - Safety population

| Final dose | Placebo (N = 161) | Lixisenatide (N = 323) |
|---|---|---|
| <10 µg | 1 (0.6%) | 0 |
| 10 µg | 2 (1.2%) | 10 (3.1%) |
| 15 µg | 1 (0.6%) | 15 (4.6%) |
| 20 µg | 157 (97.5%) | 298 (92.3%) |

Dose = Dose of active drug or volume-matched placebo.
Note:
Percentages are calculated using the number of safety patients as the denominator.

TABLE 8

Number (%) of patients by final total daily dose at the end of 24-week treatment - Safety population

| Dose at the end of the 24-week | Placebo (N = 161) | Lixisenatide (N = 323) |
|---|---|---|
| 10 µg | 1 (0.6%) | 10 (3.1%) |
| 15 µg | 1 (0.6%) | 14 (4.3%) |
| 20 µg | 159 (98.8%) | 299 (92.6%) |

Dose = Dose of active drug or volume-matched placebo.
Note:
Percentages are calculated using the number of safety patients as the denominator.

6.2 Efficacy

6.2.1 Primary Efficacy Endpoint

Main Analysis

Table 9 summarizes the results of the primary efficacy parameter, change from baseline to Week 24 (LOCF) in HbA1c using an ANCOVA analysis.

The pre-specified primary analysis showed that treatment with lixisenatide resulted in a statistically significant decrease in HbA1c from baseline to Week 24, compared with the placebo group (LS mean difference versus the placebo group=−0.56%; p-value<0.0001).

TABLE 9

Mean change in HbA1c (%) from baseline to Week 24 - mITT population

| HbA1c (%) | Placebo (N = 159) | Lixisenatide (N = 320) |
|---|---|---|
| Baseline | | |
| Number | 148 | 308 |
| Mean (SD) | 8.05 (0.78) | 8.08 (0.91) |
| Median | 7.90 | 7.90 |
| Min:Max | 6.5:10.2 | 6.5:12.7 |
| Week 24 (LOCF) | | |
| Number | 148 | 308 |
| Mean (SD) | 7.59 (0.96) | 7.06 (0.96) |
| Median | 7.40 | 6.90 |
| Min:Max | 5.5:10.4 | 5.3:11.3 |
| Change from baseline to week 24 (LOCF) | | |
| Number | 148 | 308 |
| Mean (SD) | −0.46 (1.00) | −1.02 (1.09) |
| Median | −0.40 | −0.90 |
| Min:Max | −4.0:2.5 | −5.4:3.5 |
| LS Mean (SE)[a] | −0.34 (0.100) | −0.90 (0.089) |
| LS Mean difference (SE) vs. Placebo[a] | — | −0.56 (0.088) |
| 95% CI | — | (−0.731 to −0.386) |
| p-value | | <.0001 |

LOCF = Last observation carried forward.
[a] Analysis of covariance (ANCOVA) model with treatment groups (lixisenatide and placebo), randomization strata of screening HbA1c (<8.0, ≥8.0%), randomization strata of metformin use at screening, and country as fixed effects and baseline HbA1c value as a covariate.
Note:
The analysis includes measurements before the introduction of rescue medication and up to 3 days after the last dose of the double-blind investigational product injection on or before Visit 12 (Week 24), or Day 169 if Visit 12 (Week 24) is not available. Patients with both baseline and Week 24 (LOCF) measurements are included.

Figure 3:
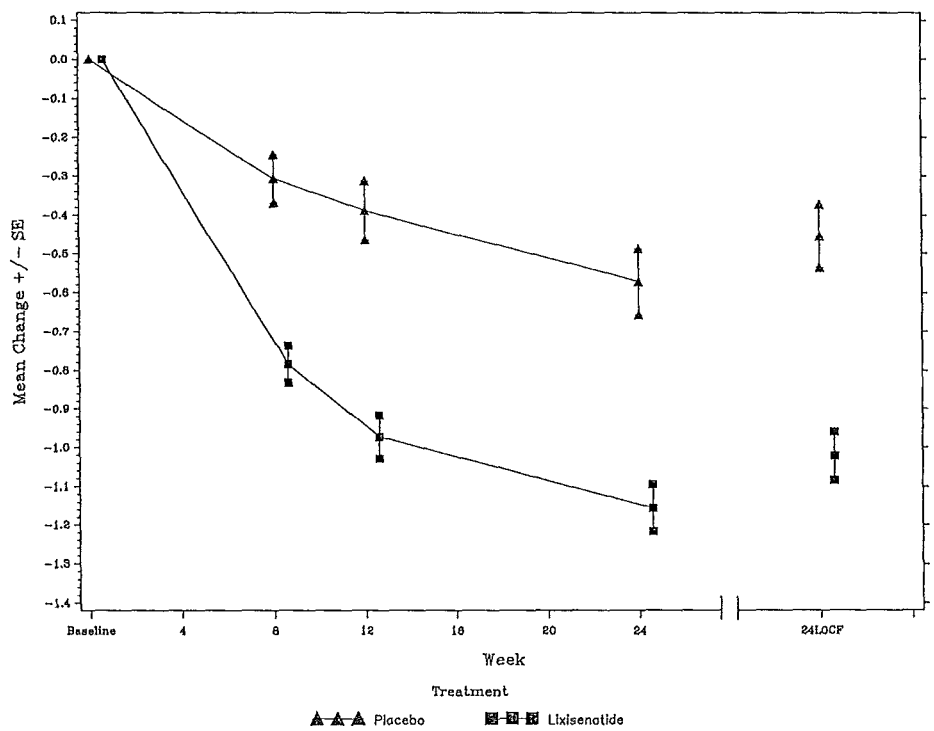
FIG. 3—Plot of mean change in HbA1c (%) from baseline by visit up to Week 24—mITT population. LOCF=Last observation carried forward. Note: The plot includes measurements before the introduction of rescue medication and up to 3 days after the last dose of the double-blind investigational product injection on or before Visit 12 (Week 24), or Day 169 if Visit 12 (Week 24) is not available.
Figure 6:
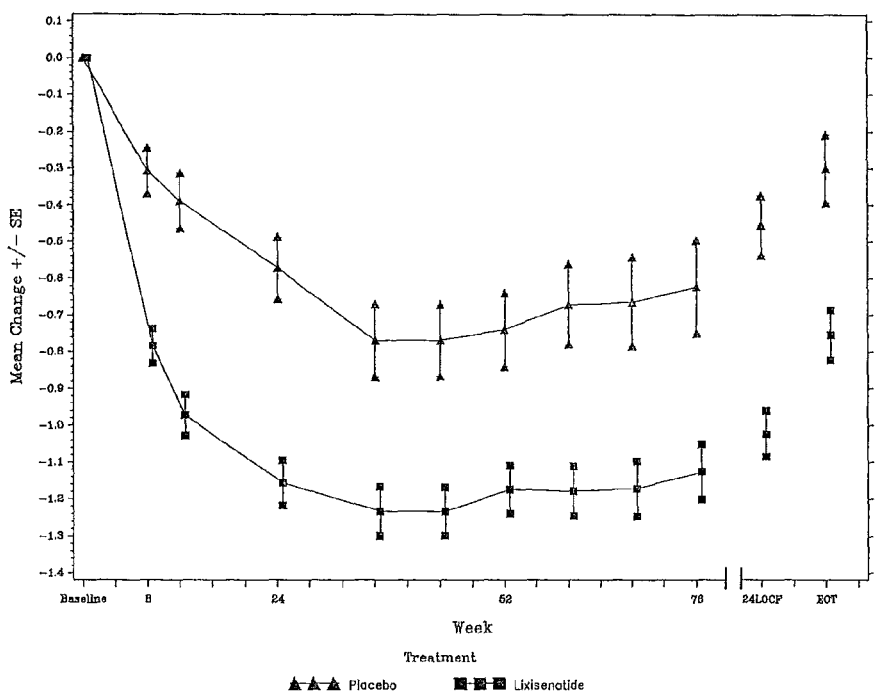
FIG. 6—Plot of mean change in HbA1c (%) from baseline by visit—mITT population. LOCF=Last observation carried forward, EOT=Last on-treatment value. Note: The analysis excludes measurements obtained after the introduction of rescue medication and/or after the treatment cessation plus 3 days. For Week 24 (LOCF), the analysis includes measurements obtained up to 3 days after the last dose of the double-blind investigational product injection on or before Visit 12 (Week 24), or Day 169 if Visit 12 (Week 24) is not available.

FIG. 3 illustrates the mean (±SE) change from baseline in HbA1c over time during the main 24-week double-blind treatment period. FIG. 6 in the appendix displays the mean (±SE) change from baseline in HbA1c over time up to Week 76. The reduction of HbA1c was maintained over time beyond 24 weeks.

Secondary Analysis

Table 10 summarizes the proportion of patients with treatment response HbA1c≤6.5% or <7% at Week 24, respectively. The analysis of HbA1c responders using the CMH method showed a statistically significant treatment difference between the lixisenatide group and the placebo group (p-value<0.0001).

TABLE 10

Number (%) of patients with HbA1c value ≤6.5% or <7% respectively at Week 24 - mITT population

| HbA1c (%) | Placebo (N = 159) | Lixisenatide (N = 320) |
|---|---|---|
| Number | 148 | 308 |
| ≤6.5% | 15 (10.1%) | 89 (28.9%) |
| >6.5% | 133 (89.9%) | 219 (71.1%) |
| p-value vs. placebo[a] | — | <0.0001 |
| Number | 148 | 308 |
| <7.0% | 39 (26.4%) | 161 (52.3%) |
| ≥7.0% | 109 (73.6%) | 147 (47.7%) |
| p-value vs. placebo[a] | — | <0.0001 |

[a] Cochran-Mantel-Haenszel (CMH) method stratified by randomization strata of screening HbA1c (<8.0 or ≥8.0%) and randomization strata of metformin use at screening (Yes or No).
Note:
The analysis includes measurements before the introduction of rescue medication and up to 3 days after the last dose of the double-blind investigational product injection on or before Visit 12 (Week 24), or Day 169 if Visit 12 (Week 24) is not available.

6.2.2 Key Secondary Efficacy Endpoints

Figure 4:
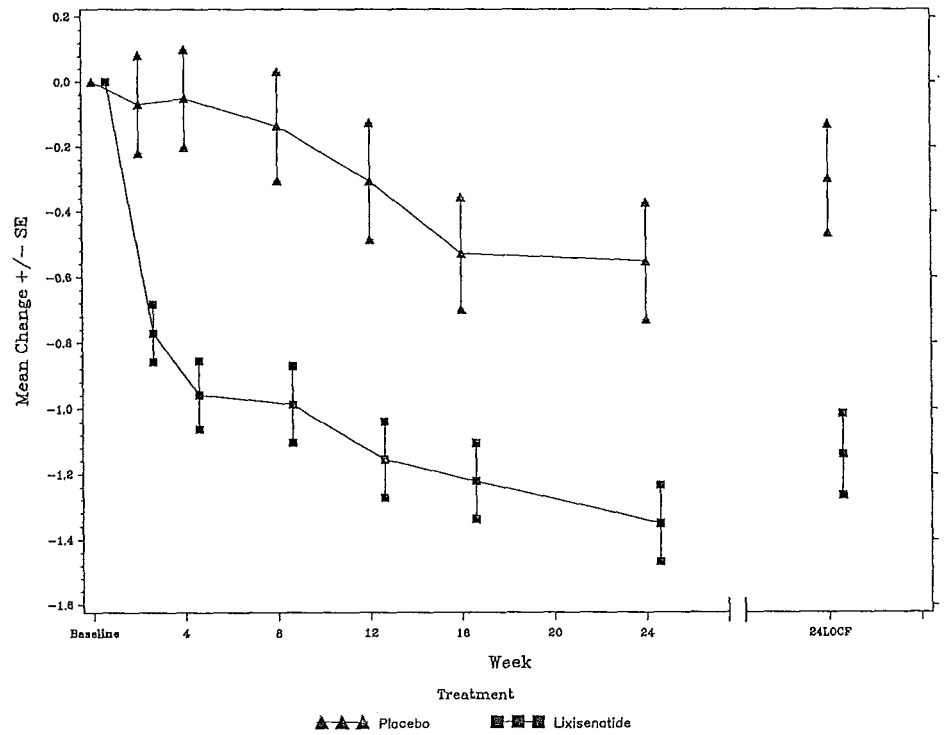
FIG. 4—Plot of mean change in fasting plasma glucose (mmol/L) from baseline by visit up to Week 24—mITT population. LOCF=Last observation carried forward. Note: The plot includes measurements before the introduction of rescue medication and up to 1 day after the last dose of the double-blind investigational product injection on or before Visit 12 (Week 24), or Day 169 if Visit 12 (Week 24) is not available.
Figure 5:
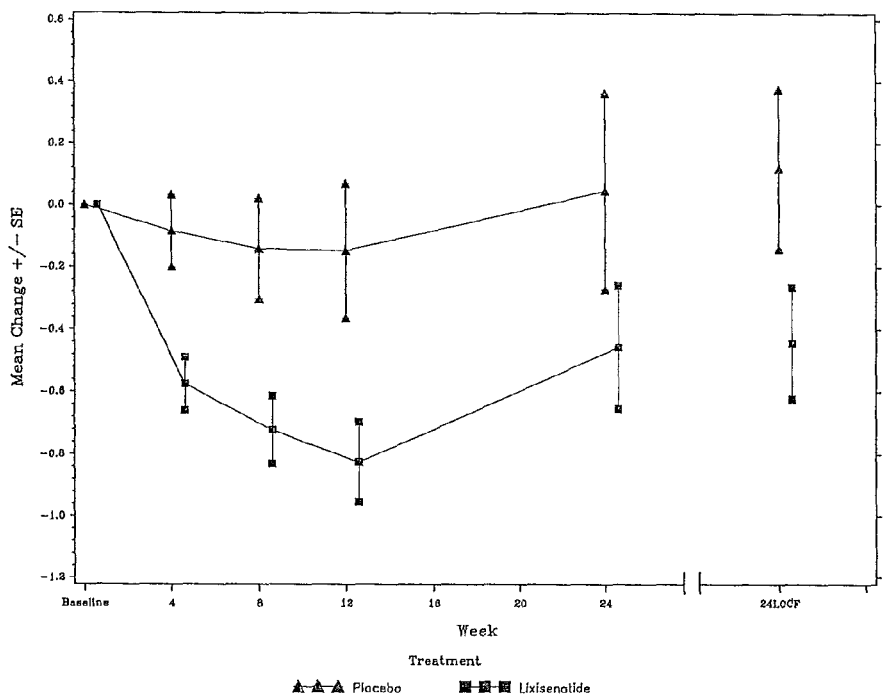
FIG. 5—Plot of mean change in body weight (kg) from baseline by visit up to Week 24—mITT population. LOCF=Last observation carried forward. Note: The plot includes measurements before the introduction of rescue medication and up to 3 days after the last dose of the double-blind investigational product injection on or before Visit 12 (Week 24), or Day 169 if Visit 12 (Week 24) is not available.
Figure 7:
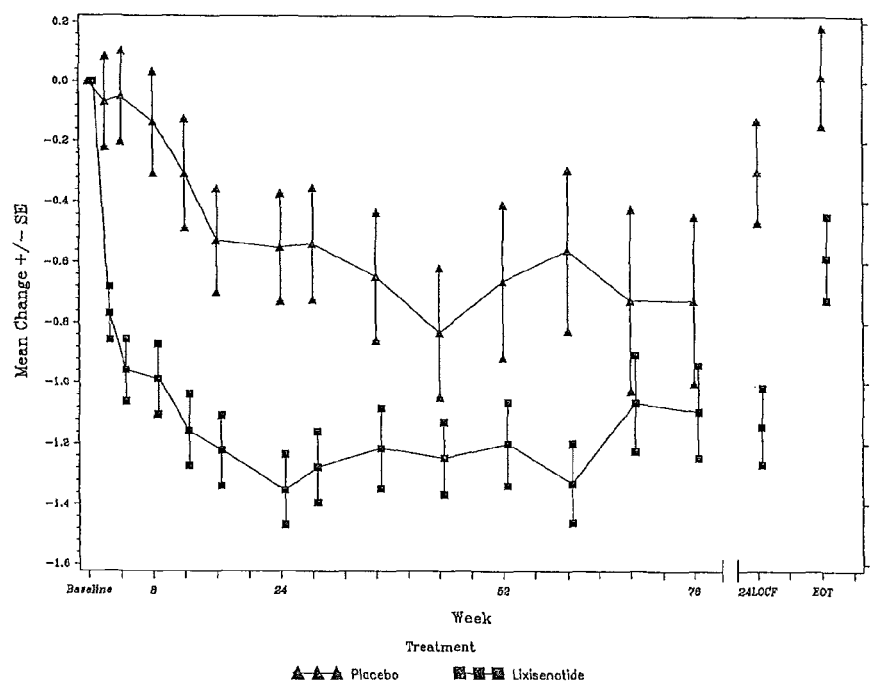
FIG. 7—Plot of mean change in fasting plasma glucose (mmol/L) from baseline by visit—mITT population. LOCF=Last observation carried forward, EOT=Last on-treatment value. Note: The analysis excludes measurements obtained after the introduction of rescue medication and/or after the treatment cessation plus 1 day. For Week 24 (LOCF), the analysis includes measurements obtained up to 1 day after the last dose of the double-blind investigational product injection on or before Visit 12 (Week 24), or Day 169 if Visit 12 (Week 24) is not available.
Figure 8:
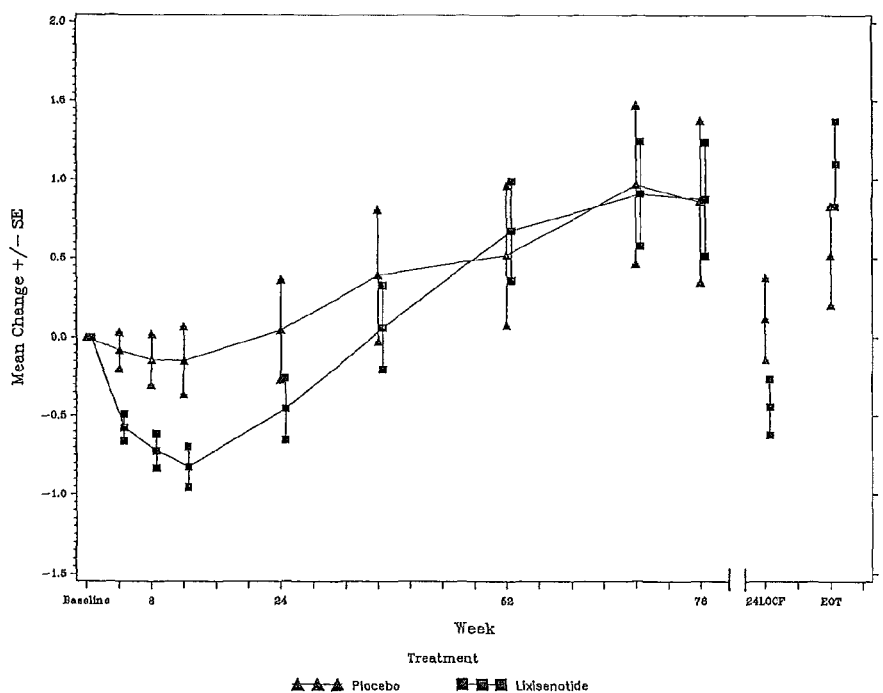
FIG. 8—Plot of mean change in body weight (kg) from baseline by visit—mITT population. LOCF=Last observation carried forward, EOT=Last on-treatment value. Note: The analysis excludes measurements obtained after the introduction of rescue medication and/or after the treatment cessation plus 3 days. For Week 24 (LOCF), the analysis includes measurements obtained up to 3 days after the last dose of the double-blind investigational product injection on or before Visit 12 (Week 24), or Day 169 if Visit 12 (Week 24) is not available.

The ANCOVA analyses of FPG, body weight, HOMA-β and FPI are presented in this section. FIG. 4 and FIG. 5 illustrate the mean (±SE) change from baseline in FPG and body weight over time during the main 24-week double-blind treatment period. Mean (±SE) changes from baseline in FPG and body weight over time up to Week 76 are depicted in FIG. 7 and FIG. 8 in the appendix respectively. The percentage of patients who were rescued during the main 24 week double-blind treatment period is presented in Table 15.

For FPG, a significant decrease from baseline to Week 24 was observed in the lixisenatide group compared to the placebo group (LS mean difference versus placebo=−0.84 mmol/L; p-value <0.0001) (Table 11).

For body weight, the LS mean decrease was 0.21 kg from baseline at Week 24 in the lixisenatide group, compared to a LS mean increase of 0.21 kg in the placebo group, but the difference between the 2 groups was not significant (LS mean difference versus placebo=−0.41 kg) (Table 12). About 9.2% patients in the lixisenatide group and 5.1% in the placebo group had ≥5% weight loss from baseline to Week 24 (Table 13).

Per the testing strategy for multiplicity adjustment, the inferential testing for the subsequent efficacy variables was exploratory, since the body weight analysis failed to show a statistically significant difference.

For β-cell function assessed by HOMA-β, no relevant difference was observed between lixisenatide and placebo with LS mean difference of −0.25 (95% CI: [−6.579 to 6.070]) (Table 14).

The percentage of patients requiring rescue therapy at Week 24 was substantially lower in the lixisenatide group (12 patients [3.8%]) compared to the placebo group (18 patients [11.3%]) (Table 15).

For FPI, the LS mean reduction was greater in the lixisenatide group than in the placebo group with LS mean difference of −9.36 pmol/L (95% CI: [−16.586 to −2.124]) (Table 16).

TABLE 11

Mean change in fasting plasma glucose (mmol/L) from baseline to Week 24 - mITT population

| Fasting plasma glucose (mmol/L) | Placebo (N = 159) | Lixisenatide (N = 320) |
|---|---|---|
| Baseline | | |
| Number | 159 | 317 |
| Mean (SD) | 9.12 (2.19) | 9.14 (2.15) |
| Median | 8.70 | 8.80 |
| Min:Max | 4.7:17.9 | 4.5:17.2 |

TABLE 11-continued

Mean change in fasting plasma glucose (mmol/L)
from baseline to Week 24 - mITT population

| Fasting plasma glucose (mmol/L) | Placebo (N = 159) | Lixisenatide (N = 320) |
|---|---|---|
| Week 24 (LOCF) | | |
| Number | 159 | 317 |
| Mean (SD) | 8.82 (2.32) | 8.00 (2.29) |
| Median | 8.50 | 7.70 |
| Min:Max | 3.8:16.9 | 4.5:27.6 |
| Change from baseline to week 24 (LOCF) | | |
| Number | 159 | 317 |
| Mean (SD) | −0.30 (2.12) | −1.14 (2.24) |
| Median | −0.40 | −1.10 |
| Min:Max | −7.0:6.0 | −9.6:17.6 |
| LS Mean (SE)[a] | −0.32 (0.215) | −1.16 (0.192) |
| LS Mean difference (SE) vs. Placebo[a] | — | −0.84 (0.189) |
| 95% CI | — | (−1.209 to −0.467) |
| p-value | | <.0001 |

LOCF = Last observation carried forward.

[a] Analysis of covariance (ANCOVA) model with treatment groups (lixisenatide and placebo), randomization strata of screening HbA1c (<8.0, ≥8.0%), metformin use at screening (Yes, No), and country as fixed effects and baseline fasting plasma glucose as a covariate.

Note:
The analysis includes measurements before the introduction of rescue medication and up to 1 day after the last dose of the double-blind investigational product injection on or before Visit 12 (Week 24), or Day 169 if Visit 12 (Week 24) is not available. Patients with both baseline and Week 24 (LOCF) measurements are included.

TABLE 12

Mean change in body weight (kg) from
baseline to Week 24 - mITT population

| Body weight (kg) | Placebo (N = 159) | Lixisenatide (N = 320) |
|---|---|---|
| Baseline | | |
| Number | 157 | 315 |
| Mean (SD) | 97.03 (25.81) | 92.83 (23.01) |
| Median | 93.00 | 92.00 |
| Min:Max | 45.0:198.3 | 48.5:162.7 |
| Week 24 (LOCF) | | |
| Number | 157 | 315 |
| Mean (SD) | 97.14 (26.19) | 92.38 (23.17) |
| Median | 94.00 | 92.00 |
| Min:Max | 45.1:199.6 | 46.5:167.1 |
| Change from baseline to week 24 (LOCF) | | |
| Number | 157 | 315 |
| Mean (SD) | 0.12 (3.24) | −0.44 (3.17) |
| Median | 0.00 | −0.50 |
| Min:Max | −11.9:11.7 | −12.6:9.8 |
| LS Mean (SE)[a] | 0.21 (0.357) | −0.21 (0.324) |
| LS Mean difference (SE) vs. Placebo[a] | — | −0.41 (0.314) |
| 95% CI | — | (−1.031 to 0.201) |
| p-value | | 0.1864 |

LOCF = Last observation carried forward.

[a] Analysis of covariance (ANCOVA) model with treatment groups (lixisenatide and placebo), randomization strata of screening HbA1c (<8.0, ≥8.0%), metformin use at screening (Yes, No), and country as fixed effects and baseline body weight as a covariate.

Note:
The analysis includes measurements before the introduction of rescue medication and up to 3 days after the last dose of the double-blind investigational product injection on or before Visit 12 (Week 24), or Day 169 if Visit 12 (Week 24) is not available. Patients with both baseline and Week 24 (LOCF) measurements are included.

TABLE 13

Number (%) of patients with ≥5% weight loss
from baseline to Week 24 - mITT population

| Weight loss | Placebo (N = 159) | Lixisenatide (N = 320) |
|---|---|---|
| Number | 157 | 315 |
| ≥5% | 8 (5.1%) | 29 (9.2%) |
| <5% | 149 (94.9%) | 286 (90.8%) |

The analysis includes measurements before the introduction of rescue medication and up to 3 days after the last dose of the double-blind investigational product injection on or before Visit 12 (Week 24), or Day 169 if Visit 12 (Week 24) is not available.

TABLE 14

Mean change in HOMA-beta from baseline
to Week 24 - mITT population

| HOMA-β | Placebo (N = 159) | Lixisenatide (N = 320) |
|---|---|---|
| Baseline | | |
| Number | 124 | 281 |
| Mean (SD) | 37.37 (26.24) | 33.93 (27.49) |
| Median | 30.03 | 26.27 |
| Min:Max | 1.1:157.6 | 3.8:206.8 |
| Week 24 (LOCF) | | |
| Number | 124 | 281 |
| Mean (SD) | 44.26 (41.19) | 42.48 (30.87) |
| Median | 34.23 | 33.21 |
| Min:Max | 2.0:356.7 | 3.6:208.9 |
| Change from baseline to week 24 (LOCF) | | |
| Number | 124 | 281 |
| Mean (SD) | 6.88 (36.07) | 8.55 (27.98) |
| Median | 3.70 | 7.26 |
| Min:Max | −63.9:328.5 | −140.1:163.1 |
| LS Mean (SE)[a] | 6.98 (3.575) | 6.72 (2.963) |
| LS Mean difference (SE) vs. Placebo[a] | — | −0.25 (3.217) |
| 95% CI | — | (−6.579 to 6.070) |
| p-value | | 0.9369 |

LOCF = Last observation carried forward.

[a] Analysis of covariance (ANCOVA) model with treatment groups (lixisenatide and placebo), randomization strata of screening HbA1c (<8.0, ≥8.0%), metformin use at screening (Yes, No), and country as fixed effects and baseline HOMA-β value as a covariate.

Note:
The analysis includes measurements before the introduction of rescue medication and up to 1 day after the last dose of the double-blind investigational product injection on or before Visit 12 (Week 24), or Day 169 if Visit 12 (Week 24) is not available. Patients with both baseline and Week 24 (LOCF) measurements are included.

TABLE 15

Number (%) of patients requiring rescue therapy during the main
24-week double-blind treatment period - mITT population

| Requiring rescue therapy | Placebo (N = 159) | Lixisenatide (N = 320) |
|---|---|---|
| Number | 159 | 320 |
| Yes | 18 (11.3%) | 12 (3.8%) |
| No | 141 (88.7%) | 308 (96.3%) |
| p-value vs. placebo[a] | — | 0.0011 |

[a] Cochran-Mantel-Haenszel (CMH) method stratified by randomization strata of screening HbA1c (<8.0 or ≥8.0%) and metformin use at screening (Yes, No).

TABLE 16

Mean change in fasting plasma insulin (pmol/L)
from baseline to Week 24 - mITT population

| Fasting plasma insulin (pmol/L) | Placebo (N = 159) | Lixisenatide (N = 320) |
|---|---|---|
| Baseline | | |
| Number | 125 | 281 |
| Mean (SD) | 68.08 (49.25) | 62.66 (56.88) |
| Median | 56.25 | 45.99 |
| Min:Max | 4.9:356.1 | 9.4:635.7 |
| Week 24 (LOCF) | | |
| Number | 125 | 281 |
| Mean (SD) | 67.41 (47.06) | 57.11 (36.28) |
| Median | 56.68 | 48.14 |
| Min:Max | 9.5:274.9 | 7.7:358.8 |
| Change from baseline to Week 24 (LOCF) | | |
| Number | 125 | 281 |
| Mean (SD) | −0.67 (40.70) | −5.55 (51.84) |
| Median | −1.65 | 0.65 |
| Min:Max | −143.9:186.8 | −517.1:199.3 |
| LS Mean (SE) [a] | −1.01 (4.080) | −10.36 (3.397) |
| LS Mean difference (SE) vs. Placebo [a] | — | −9.36 (3.678) |
| 95% CI | — | (−16.586 to −2.124) |
| p-value | | 0.0114 |

LOCF = Last observation carried forward.
[a] Analysis of covariance (ANCOVA) model with treatment groups (lixisenatide and placebo), randomization strata of screening HbA1c (<8.0, ≥8.0%), randomization strata of metformin use at screening (Yes, No), and country as fixed effects and baseline fasting plasma insulin value as a covariate.
The analysis includes measurements before the introduction of rescue medication and up to 1 day after the last dose of the double-blind investigational product injection on or before Visit 12 (Week 24), or Day 169 if Visit 12 (Week 24) is not available. Patients with both baseline and Week 24 (LOCF) measurements are included.

6.3 Safety

An overview of the adverse events observed during the on-treatment period for the whole study is provided in Table 17. The proportions of patients who experienced treatment emergent adverse events (TEAEs) were 87.9% in the lixisenatide group and 83.2% in the placebo group. No patients in the lixisenatide group died, but 2 patients in the placebo group died. One had a treatment emergent acute myocardial infarction leading to death and the other died due to a post-treatment AE (end stage debility) following respiratory failure with multiorgan failure. The percentage of patients who had serious TEAEs was lower in the lixisenatide group (7.4%) than in the placebo group (9.3%). Higher percentage of patients in the lixisenatide group (9.3%) experienced TEAEs leading to treatment discontinuation than in the placebo group (7.5%). Table 18, Table 19, and Table 20 summarize TEAEs leading to death, serious TEAEs, and TEAEs leading to treatment discontinuation by primary SOC, HLGT, HLT and PT, respectively. The most common TEAE leading to treatment discontinuation was nausea in the lixisenatide group (6 patients [1.9%]) while no patient discontinued treatment due to nausea in the placebo group.

Table 30 in the appendix presents the incidences of TEAEs during the on-treatment period of the whole study occurring in at least 1% of patients in any treatment group. Nausea was the most frequently reported TEAE in the lixisenatide group (84 patients [26.0%] versus 22 [13.7%] for placebo). The second most frequently reported TEAE in the lixisenatide group was nasopharyngitis (53 [16.4%] versus 24 [14.9%] for placebo) followed by headache (43 [13.3%] versus 19 [11.8%] for placebo), upper respiratory tract infection (41 [12.7%] versus 18 [11.2%] for placebo), diarrhea (35 [10.8%] versus 23 [14.3%] for placebo), and dizziness (33 [10.2%] versus 13 [8.1%] for placebo).

TABLE 17

Overview of adverse event profile: treatment emergent
adverse events during the on-treatment period
of the whole study - Safety population

| | Placebo (N = 161) | Lixisenatide (N = 323) |
|---|---|---|
| Patients with any TEAE | 134 (83.2%) | 284 (87.9%) |
| Patients with any serious TEAE | 15 (9.3%) | 24 (7.4%) |
| Patients with any TEAE leading to death | 1 (0.6%) | 0 |
| Patients with any TEAE leading to permanent treatment discontinuation | 12 (7.5%) | 30 (9.3%) |

TEAE: Treatment Emergent Adverse Event
n (%) = number and percentage of patients with at least one adverse event
Note:
on-treatment period of the whole study = the time from the first dose of double-blind study medication up to 3 days after the last dose administration.

TABLE 18

Number (%) of patients experiencing TEAE(s) leading to
death by primary SOC, HLGT, HLT, and PT during the on-treatment
period of the whole study - Safety population

| PRIMARY SYSTEM ORGAN CLASS HLGT: High Level Group Term HLT: High Level Term Preferred Term | Placebo (N = 161) | Lixisenatide (N = 323) |
|---|---|---|
| Any class | 1 (0.6%) | 0 |
| CARDIAC DISORDERS | 1 (0.6%) | 0 |
|   HLGT: Coronary artery disorders | 1 (0.6%) | 0 |
|     HLT: Ischaemic coronary artery disorders | 1 (0.6%) | 0 |
|       Acute myocardial infarction | 1 (0.6%) | 0 |

TEAE: Treatment Emergent Adverse Event, SOC: System Organ Class, HLGT: High Level Group Term, HLT: High Level Term, PT: Preferred Term.
MedDRA version: 14.0.
n (%) = number and percentage of patients with at least one TEAE leading to death.
Note:
on-treatment period of the whole study = the time from the first dose of double-blind study medication up to 3 days after the last dose administration.
Table sorted by SOC internationally agreed order and HLGT, HLT, PT alphabetic order.

TABLE 19

Number (%) of patients experiencing serious TEAE presented by primary SOC, HLGT,
HLT, and PT during the on-treatment period of the whole study - Safety population

| PRIMARY SYSTEM ORGAN CLASS HLGT: High Level Group Term HLT: High Level Term Preferred Term | Placebo (N = 161) | Lixisenatide (N = 323) |
|---|---|---|
| Any class | 15 (9.3%) | 24 (7.4%) |
| INFECTIONS AND INFESTATIONS | 3 (1.9%) | 5 (1.5%) |
|   HLGT: Bacterial infectious disorders | 1 (0.6%) | 0 |

TABLE 19-continued

Number (%) of patients experiencing serious TEAE presented by primary SOC, HLGT, HLT, and PT during the on-treatment period of the whole study - Safety population

| PRIMARY SYSTEM ORGAN CLASS<br>  HLGT: High Level Group Term<br>    HLT: High Level Term<br>      Preferred Term | Placebo<br>(N = 161) | Lixisenatide<br>(N = 323) |
|---|---|---|
| HLT: Bacterial infections NEC | 1 (0.6%) | 0 |
| Cellulitis | 1 (0.6%) | 0 |
| HLGT: Infections - pathogen unspecified | 3 (1.9%) | 5 (1.5%) |
| HLT: Abdominal and gastrointestinal infections | 0 | 1 (0.3%) |
| Appendicitis | 0 | 1 (0.3%) |
| HLT: Lower respiratory tract and lung infections | 3 (1.9%) | 2 (0.6%) |
| Bronchitis | 1 (0.6%) | 1 (0.3%) |
| Pneumonia | 2 (1.2%) | 1 (0.3%) |
| HLT: Skin structures and soft tissue infections | 0 | 1 (0.3%) |
| Diabetic foot infection | 0 | 1 (0.3%) |
| HLT: Urinary tract infections | 0 | 1 (0.3%) |
| Urinary tract infection | 0 | 1 (0.3%) |
| NEOPLASMS BENIGN, MALIGNANT AND UNSPECIFIED (INCL CYSTS AND POLYPS) | 1 (0.6%) | 1 (0.3%) |
| HLGT: Hepatobiliary neoplasms malignant and unspecified | 1 (0.6%) | 0 |
| HLT: Bile duct neoplasms malignant | 1 (0.6%) | 0 |
| Bile duct cancer | 1 (0.6%) | 0 |
| HLGT: Respiratory and mediastinal neoplasms malignant and unspecified | 0 | 1 (0.3%) |
| HLT: Non-small cell neoplasms malignant of the respiratory tract cell type specified | 0 | 1 (0.3%) |
| Non-small cell lung cancer | 0 | 1 (0.3%) |
| METABOLISM AND NUTRITION DISORDERS | 1 (0.6%) | 0 |
| HLGT: Glucose metabolism disorders (incl diabetes mellitus) | 1 (0.6%) | 0 |
| HLT: Hyperglycaemic conditions NEC | 1 (0.6%) | 0 |
| Hyperglycaemia | 1 (0.6%) | 0 |
| NERVOUS SYSTEM DISORDERS | 1 (0.6%) | 3 (0.9%) |
| HLGT: Central nervous system vascular disorders | 0 | 2 (0.6%) |
| HLT: Central nervous system haemorrhages and cerebrovascular accidents | 0 | 1 (0.3%) |
| Cerebral infarction | 0 | 1 (0.3%) |
| HLT: Transient cerebrovascular events | 0 | 1 (0.3%) |
| Transient ischaemic attack | 0 | 1 (0.3%) |
| HLGT: Mental impairment disorders | 1 (0.6%) | 0 |
| HLT: Memory loss (excl dementia) | 1 (0.6%) | 0 |
| Memory impairment | 1 (0.6%) | 0 |
| HLGT: Spinal cord and nerve root disorders | 0 | 1 (0.3%) |
| HLT: Lumbar spinal cord and nerve root disorders | 0 | 1 (0.3%) |
| Sciatica | 0 | 1 (0.3%) |
| EYE DISORDERS | 0 | 2 (0.6%) |
| HLGT: Ocular infections, irritations and inflammations | 0 | 1 (0.3%) |
| HLT: Retinal, choroid and vitreous infections and inflammations | 0 | 1 (0.3%) |
| Macular oedema | 0 | 1 (0.3%) |
| HLGT: Ocular structural change, deposit and degeneration NEC | 0 | 1 (0.3%) |
| HLT: Retinal structural change, deposit and degeneration | 0 | 1 (0.3%) |
| Retinal detachment | 0 | 1 (0.3%) |
| HLGT: Retina, choroid and vitreous haemorrhages and vascular disorders | 0 | 2 (0.6%) |
| HLT: Choroid and vitreous haemorrhages and vascular disorders | 0 | 1 (0.3%) |
| Vitreous haemorrhage | 0 | 1 (0.3%) |
| HLT: Retinopathies NEC | 0 | 1 (0.3%) |
| Diabetic retinopathy | 0 | 1 (0.3%) |
| CARDIAC DISORDERS | 4 (2.5%) | 3 (0.9%) |
| HLGT: Cardiac valve disorders | 1 (0.6%) | 0 |
| HLT: Mitral valvular disorders | 1 (0.6%) | 0 |
| Mitral valve incompetence | 1 (0.6%) | 0 |
| HLGT: Coronary artery disorders | 3 (1.9%) | 3 (0.9%) |
| HLT: Coronary artery disorders NEC | 1 (0.6%) | 2 (0.6%) |
| Arteriosclerosis coronary artery | 0 | 1 (0.3%) |
| Coronary artery disease | 1 (0.6%) | 1 (0.3%) |
| HLT: Ischaemic coronary artery disorders | 2 (1.2%) | 1 (0.3%) |
| Acute coronary syndrome | 0 | 1 (0.3%) |
| Acute myocardial infarction | 1 (0.6%) | 0 |
| Angina unstable | 1 (0.6%) | 0 |
| VASCULAR DISORDERS | 0 | 2 (0.6%) |
| HLGT: Decreased and nonspecific blood pressure disorders and shock | 0 | 1 (0.3%) |
| HLT: Circulatory collapse and shock | 0 | 1 (0.3%) |
| Shock haemorrhagic | 0 | 1 (0.3%) |
| HLGT: Embolism and thrombosis | 0 | 1 (0.3%) |

TABLE 19-continued

Number (%) of patients experiencing serious TEAE presented by primary SOC, HLGT,
HLT, and PT during the on-treatment period of the whole study - Safety population

| PRIMARY SYSTEM ORGAN CLASS<br>  HLGT: High Level Group Term<br>    HLT: High Level Term<br>      Preferred Term | Placebo<br>(N = 161) | Lixisenatide<br>(N = 323) |
|---|---|---|
| HLT: Peripheral embolism and thrombosis | 0 | 1 (0.3%) |
| Blue toe syndrome | 0 | 1 (0.3%) |
| RESPIRATORY, THORACIC AND MEDIASTINAL DISORDERS | 1 (0.6%) | 1 (0.3%) |
| HLGT: Lower respiratory tract disorders (excl obstruction and infection) | 1 (0.6%) | 0 |
| HLT: Lower respiratory tract inflammatory and immunologic conditions | 1 (0.6%) | 0 |
| Pneumonitis | 1 (0.6%) | 0 |
| HLGT: Respiratory disorders NEC | 0 | 1 (0.3%) |
| HLT: Respiratory failures (excl neonatal) | 0 | 1 (0.3%) |
| Acute respiratory failure | 0 | 1 (0.3%) |
| GASTROINTESTINAL DISORDERS | 1 (0.6%) | 3 (0.9%) |
| HLGT: Abdominal hernias and other abdominal wall conditions | 0 | 2 (0.6%) |
| HLT: Umbilical hernias | 0 | 2 (0.6%) |
| Umbilical hernia | 0 | 2 (0.6%) |
| HLGT: Gastrointestinal signs and symptoms | 1 (0.6%) | 0 |
| HLT: Gastrointestinal and abdominal pains (excl oral and throat) | 1 (0.6%) | 0 |
| Abdominal pain | 1 (0.6%) | 0 |
| HLGT: Peritoneal and retroperitoneal conditions | 0 | 1 (0.3%) |
| HLT: Peritoneal and retroperitoneal haemorrhages | 0 | 1 (0.3%) |
| Peritoneal haemorrhage | 0 | 1 (0.3%) |
| HEPATOBILIARY DISORDERS | 0 | 1 (0.3%) |
| HLGT: Gallbladder disorders | 0 | 1 (0.3%) |
| HLT: Cholecystitis and cholelithiasis | 0 | 1 (0.3%) |
| Cholecystitis chronic | 0 | 1 (0.3%) |
| MUSCULOSKELETAL AND CONNECTIVE TISSUE DISORDERS | 1 (0.6%) | 3 (0.9%) |
| HLGT: Joint disorders | 0 | 3 (0.9%) |
| HLT: Arthropathies NEC | 0 | 1 (0.3%) |
| Neuropathic arthropathy | 0 | 1 (0.3%) |
| HLT: Crystal arthropathic disorders | 0 | 1 (0.3%) |
| Gouty arthritis | 0 | 1 (0.3%) |
| HLT: Osteoarthropathies | 0 | 1 (0.3%) |
| Osteoarthritis | 0 | 1 (0.3%) |
| HLGT: Musculoskeletal and connective tissue deformities (incl intervertebral disc disorders) | 1 (0.6%) | 0 |
| HLT: Spine and neck deformities | 1 (0.6%) | 0 |
| Spinal column stenosis | 1 (0.6%) | 0 |
| RENAL AND URINARY DISORDERS | 0 | 1 (0.3%) |
| HLGT: Urolithiases | 0 | 1 (0.3%) |
| HLT: Renal lithiasis | 0 | 1 (0.3%) |
| Stag horn calculus | 0 | 1 (0.3%) |
| GENERAL DISORDERS AND ADMINISTRATION SITE CONDITIONS | 0 | 3 (0.9%) |
| HLGT: General system disorders NEC | 0 | 3 (0.9%) |
| HLT: Pain and discomfort NEC | 0 | 3 (0.9%) |
| Non-cardiac chest pain | 0 | 3 (0.9%) |
| INVESTIGATIONS | 3 (1.9%) | 0 |
| HLGT: Endocrine investigations (incl sex hormones) | 1 (0.6%) | 0 |
| HLT: Gastrointestinal, pancreatic and APUD hormone analyses | 1 (0.6%) | 0 |
| Blood calcitonin increased | 1 (0.6%) | 0 |
| HLGT: Gastrointestinal investigations | 1 (0.6%) | 0 |
| HLT: Gastrointestinal and abdominal imaging procedures | 1 (0.6%) | 0 |
| Colonoscopy | 1 (0.6%) | 0 |
| HLGT: Physical examination topics | 1 (0.6%) | 0 |
| HLT: Physical examination procedures | 1 (0.6%) | 0 |
| Weight decreased | 1 (0.6%) | 0 |
| INJURY, POISONING AND PROCEDURAL COMPLICATIONS | 1 (0.6%) | 3 (0.9%) |
| HLGT: Bone and joint injuries | 1 (0.6%) | 2 (0.6%) |
| HLT: Fractures and dislocations NEC | 0 | 1 (0.3%) |
| Multiple fractures | 0 | 1 (0.3%) |
| HLT: Limb injuries NEC (incl traumatic amputation) | 1 (0.6%) | 0 |
| Meniscus lesion | 1 (0.6%) | 0 |
| HLT: Lower limb fractures and dislocations | 0 | 1 (0.3%) |
| Foot fracture | 0 | 1 (0.3%) |
| HLGT: Injuries NEC | 0 | 1 (0.3%) |
| HLT: Abdominal injuries NEC | 0 | 1 (0.3%) |
| Abdominal injury | 0 | 1 (0.3%) |
| HLT: Non-site specific injuries NEC | 0 | 1 (0.3%) |
| Injury | 0 | 1 (0.3%) |

TABLE 19-continued

Number (%) of patients experiencing serious TEAE presented by primary SOC, HLGT, HLT, and PT during the on-treatment period of the whole study - Safety population

| PRIMARY SYSTEM ORGAN CLASS<br>  HLGT: High Level Group Term<br>    HLT: High Level Term<br>      Preferred Term | Placebo<br>(N = 161) | Lixisenatide<br>(N = 323) |
|---|---|---|
| SURGICAL AND MEDICAL PROCEDURES | 2 (1.2%) | 2 (0.6%) |
|   HLGT: Vascular therapeutic procedures | 2 (1.2%) | 2 (0.6%) |
|     HLT: Arterial therapeutic procedures (excl aortic) | 2 (1.2%) | 2 (0.6%) |
|       Coronary angioplasty | 0 | 1 (0.3%) |
|       Coronary artery bypass | 2 (1.2%) | 0 |
|       Percutaneous coronary intervention | 0 | 1 (0.3%) |

TEAE: Treatment Emergent Adverse Event, SOC: System Organ Class, HLGT: High Level Group Term, HLT: High Level Term, PT: Preferred Term.
MedDRA version: 14.0.
n (%) = number and percentage of patients with at least one serious TEAE.
Note:
on-treatment period of the whole study = the time from the first dose of double-blind study medication up to 3 days after the last dose administration.
Table sorted by SOC internationally agreed order and HLGT, HLT, PT alphabetic order.

TABLE 20

Number (%) of patients experiencing TEAE(s) leading to permanent treatment discontinuation by primary SOC, HLGT, HLT, and PT during the on-treatment period of the whole study - Safety population

| PRIMARY SYSTEM ORGAN CLASS<br>  HLGT: High Level Group Term<br>    HLT: High Level Term<br>      Preferred Term | Placebo<br>(N = 161) | Lixisenatide<br>(N = 323) |
|---|---|---|
| Any class | 12 (7.5%) | 30 (9.3%) |
| INFECTIONS AND INFESTATIONS | 0 | 1 (0.3%) |
|   HLGT: Bacterial infectious disorders | 0 | 1 (0.3%) |
|     HLT: Bacterial infections NEC | 0 | 1 (0.3%) |
|       Cellulitis | 0 | 1 (0.3%) |
| METABOLISM AND NUTRITION DISORDERS | 1 (0.6%) | 0 |
|   HLGT: Appetite and general nutritional disorders | 1 (0.6%) | 0 |
|     HLT: Appetite disorders | 1 (0.6%) | 0 |
|       Decreased appetite | 1 (0.6%) | 0 |
| PSYCHIATRIC DISORDERS | 0 | 2 (0.6%) |
|   HLGT: Anxiety disorders and symptoms | 0 | 2 (0.6%) |
|     HLT: Panic attacks and disorders | 0 | 2 (0.6%) |
|       Panic attack | 0 | 2 (0.6%) |
| NERVOUS SYSTEM DISORDERS | 1 (0.6%) | 5 (1.5%) |
|   HLGT: Central nervous system vascular disorders | 0 | 1 (0.3%) |
|     HLT: Central nervous system haemorrhages and cerebrovascular accidents | 0 | 1 (0.3%) |
|       Cerebral infarction | 0 | 1 (0.3%) |
|   HLGT: Headaches | 0 | 2 (0.6%) |
|     HLT: Headaches NEC | 0 | 2 (0.6%) |
|       Headache | 0 | 2 (0.6%) |
|   HLGT: Mental impairment disorders | 1 (0.6%) | 0 |
|     HLT: Memory loss (excl dementia) | 1 (0.6%) | 0 |
|       Memory impairment | 1 (0.6%) | 0 |
|   HLGT: Neurological disorders NEC | 0 | 3 (0.9%) |
|     HLT: Neurological signs and symptoms NEC | 0 | 3 (0.9%) |
|       Dizziness | 0 | 3 (0.9%) |
| EYE DISORDERS | 0 | 1 (0.3%) |
|   HLGT: Vision disorders | 0 | 1 (0.3%) |
|     HLT: Partial vision loss | 0 | 1 (0.3%) |
|       Visual acuity reduced | 0 | 1 (0.3%) |
| EAR AND LABYRINTH DISORDERS | 0 | 1 (0.3%) |
|   HLGT: Hearing disorders | 0 | 1 (0.3%) |
|     HLT: Hearing losses | 0 | 1 (0.3%) |
|       Deafness bilateral | 0 | 1 (0.3%) |
| CARDIAC DISORDERS | 2 (1.2%) | 1 (0.3%) |
|   HLGT: Cardiac arrhythmias | 1 (0.6%) | 0 |
|     HLT: Supraventricular arrhythmias | 1 (0.6%) | 0 |
|       Atrial fibrillation | 1 (0.6%) | 0 |
|   HLGT: Cardiac valve disorders | 1 (0.6%) | 0 |
|     HLT: Mitral valvular disorders | 1 (0.6%) | 0 |
|       Mitral valve incompetence | 1 (0.6%) | 0 |
|   HLGT: Coronary artery disorders | 1 (0.6%) | 1 (0.3%) |
|     HLT: Ischaemic coronary artery disorders | 1 (0.6%) | 1 (0.3%) |
|       Acute myocardial infarction | 1 (0.6%) | 0 |

TABLE 20-continued

Number (%) of patients experiencing TEAE(s) leading to permanent treatment discontinuation by primary SOC, HLGT, HLT, and PT during the on-treatment period of the whole study - Safety population

| PRIMARY SYSTEM ORGAN CLASS<br>  HLGT: High Level Group Term<br>    HLT: High Level Term<br>      Preferred Term | Placebo<br>(N = 161) | Lixisenatide<br>(N = 323) |
|---|---|---|
| Myocardial ischaemia | 0 | 1 (0.3%) |
| RESPIRATORY, THORACIC AND MEDIASTINAL DISORDERS | 1 (0.6%) | 2 (0.6%) |
|   HLGT: Respiratory disorders NEC | 1 (0.6%) | 2 (0.6%) |
|     HLT: Breathing abnormalities | 0 | 1 (0.3%) |
|       Dyspnoea | 0 | 1 (0.3%) |
|     HLT: Coughing and associated symptoms | 1 (0.6%) | 0 |
|       Cough | 1 (0.6%) | 0 |
|     HLT: Upper respiratory tract signs and symptoms | 0 | 1 (0.3%) |
|       Throat tightness | 0 | 1 (0.3%) |
| GASTROINTESTINAL DISORDERS | 1 (0.6%) | 10 (3.1%) |
|   HLGT: Gastrointestinal motility and defaecation conditions | 0 | 1 (0.3%) |
|     HLT: Diarrhoea (excl infective) | 0 | 1 (0.3%) |
|       Diarrhoea | 0 | 1 (0.3%) |
|   HLGT: Gastrointestinal signs and symptoms | 1 (0.6%) | 8 (2.5%) |
|     HLT: Flatulence, bloating and distension | 0 | 2 (0.6%) |
|       Abdominal distension | 0 | 1 (0.3%) |
|       Flatulence | 0 | 1 (0.3%) |
|     HLT: Gastrointestinal and abdominal pains (excl oral and throat) | 1 (0.6%) | 0 |
|       Abdominal pain lower | 1 (0.6%) | 0 |
|     HLT: Nausea and vomiting symptoms | 0 | 7 (2.2%) |
|       Nausea | 0 | 6 (1.9%) |
|       Vomiting | 0 | 2 (0.6%) |
|   HLGT: Gastrointestinal ulceration and perforation | 0 | 1 (0.3%) |
|     HLT: Peptic ulcers and perforation | 0 | 1 (0.3%) |
|       Peptic ulcer | 0 | 1 (0.3%) |
| SKIN AND SUBCUTANEOUS TISSUE DISORDERS | 1 (0.6%) | 3 (0.9%) |
|   HLGT: Angioedema and urticaria | 0 | 1 (0.3%) |
|     HLT: Urticarias | 0 | 1 (0.3%) |
|       Urticaria | 0 | 1 (0.3%) |
|   HLGT: Epidermal and dermal conditions | 1 (0.6%) | 2 (0.6%) |
|     HLT: Dermatitis and eczema | 1 (0.6%) | 2 (0.6%) |
|       Dermatitis | 0 | 1 (0.3%) |
|       Dermatitis allergic | 0 | 1 (0.3%) |
|       Eczema | 1 (0.6%) | 0 |
| MUSCULOSKELETAL AND CONNECTIVE TISSUE DISORDERS | 0 | 3 (0.9%) |
|   HLGT: Joint disorders | 0 | 1 (0.3%) |
|     HLT: Joint related signs and symptoms | 0 | 1 (0.3%) |
|       Arthralgia | 0 | 1 (0.3%) |
|   HLGT: Muscle disorders | 0 | 1 (0.3%) |
|     HLT: Muscle pains | 0 | 1 (0.3%) |
|       Myalgia | 0 | 1 (0.3%) |
|   HLGT: Musculoskeletal and connective tissue disorders NEC | 0 | 1 (0.3%) |
|     HLT: Musculoskeletal and connective tissue pain and discomfort | 0 | 1 (0.3%) |
|       Pain in extremity | 0 | 1 (0.3%) |
| GENERAL DISORDERS AND ADMINISTRATION SITE CONDITIONS | 1 (0.6%) | 5 (1.5%) |
|   HLGT: General system disorders NEC | 1 (0.6%) | 5 (1.5%) |
|     HLT: Asthenic conditions | 0 | 2 (0.6%) |
|       Asthenia | 0 | 1 (0.3%) |
|       Fatigue | 0 | 1 (0.3%) |
|     HLT: Oedema NEC | 1 (0.6%) | 2 (0.6%) |
|       Oedema | 0 | 1 (0.3%) |
|       Oedema peripheral | 1 (0.6%) | 1 (0.3%) |
|     HLT: Pain and discomfort NEC | 0 | 1 (0.3%) |
|       Non-cardiac chest pain | 0 | 1 (0.3%) |
| INVESTIGATIONS | 4 (2.5%) | 4 (1.2%) |
|   HLGT: Endocrine investigations (incl sex hormones) | 2 (1.2%) | 1 (0.3%) |
|     HLT: Gastrointestinal, pancreatic and APUD hormone analyses | 2 (1.2%) | 1 (0.3%) |
|       Blood calcitonin increased | 2 (1.2%) | 1 (0.3%) |
|   HLGT: Gastrointestinal investigations | 1 (0.6%) | 1 (0.3%) |
|     HLT: Digestive enzymes | 1 (0.6%) | 1 (0.3%) |
|       Blood amylase increased | 1 (0.6%) | 1 (0.3%) |
|       Lipase increased | 1 (0.6%) | 1 (0.3%) |
|   HLGT: Metabolic, nutritional and blood gas investigations | 0 | 1 (0.3%) |
|     HLT: Carbohydrate tolerance analyses (incl diabetes) | 0 | 1 (0.3%) |
|       Glycosylated haemoglobin increased | 0 | 1 (0.3%) |
|   HLGT: Physical examination topics | 1 (0.6%) | 1 (0.3%) |
|     HLT: Physical examination procedures | 1 (0.6%) | 1 (0.3%) |

TABLE 20-continued

Number (%) of patients experiencing TEAE(s) leading to permanent treatment discontinuation by primary SOC, HLGT, HLT, and PT during the on-treatment period of the whole study - Safety population

| PRIMARY SYSTEM ORGAN CLASS<br>  HLGT: High Level Group Term<br>    HLT: High Level Term<br>      Preferred Term | Placebo<br>(N = 161) | Lixisenatide<br>(N = 323) |
|---|---|---|
| Weight increased | 1 (0.6%) | 1 (0.3%) |
| INJURY, POISONING AND PROCEDURAL COMPLICATIONS | 0 | 1 (0.3%) |
|   HLGT: Injuries NEC | 0 | 1 (0.3%) |
|     HLT: Abdominal injuries NEC | 0 | 1 (0.3%) |
|       Abdominal injury | 0 | 1 (0.3%) |

TEAE: Treatment Emergent Adverse Event, SOC: System Organ Class, HLGT: High Level Group Term, HLT: High Level Term, PT: Preferred Term.
MedDRA version: 14.0.
n (%) = number and percentage of patients with at least one TEAE leading to permanent treatment discontinuation.
Note:
on-treatment period of the whole study = the time from the first dose of double-blind study medication up to 3 days after the last dose administration.
Table sorted by SOC internationally agreed order and HLGT, HLT, PT alphabetic order.

During the on-treatment period of the whole study, a total of 36 patients (27 in the lixisenatide group and 9 in the placebo group) reported TEAEs on a pre-specified AE form for "symptomatic hypoglycaemia". Among them, 23 (7.1%) patients in the lixisenatide group had symptomatic hypoglycemia per protocol definition, compared to 7 (4.3%) in the placebo group (Table 21). None of the symptomatic hypoglycemia events were severe in intensity. The events in the remaining 6 patients (4 in the lixisenatide group and 2 in the placebo group) did not meet the protocol-specified symptomatic hypoglycemia definition due to the associated glucose values being ≥60 mg/dL or no symptoms reported.

Twenty-two (6.8%) patients in the lixisenatide group and 8 (5.0%) in the placebo group experienced injection site reaction AEs (Table 22). The injection site reaction AEs were identified by searching the term "injection site" in either the PTs coded from the investigator reported terms or the PTs from the ARAC diagnosis after the allergic reaction adjudication. None of these injection site reaction events were serious or severe in intensity or led to IP discontinuation.

A total of 56 possible allergic events were reported in 39 patients by investigators and were sent to ARAC for adjudication during the on-treatment period of the whole study. Of these, 19 events in 12 patients (9 [2.8%] patients in the lixisenatide group and 3 [1.9%] in the placebo group) were adjudicated as allergic reactions by ARAC, which included 5 events in 3 patients in the lixisenatide group (1 with allergic dermatitis, 1 with urticaria, and 1 with angioedema, anaphylactic reaction, and allergic conjunctivitis) adjudicated as possibly related to IP. (Table 23).

Patient 124713001 (lixisenatide group): with a medical history of urticaria and multiple allergies, as well as pruritus, on Day 258 (Nov. 7, 2009) after start of IP experienced a non-serious TEAE of WELT FROM NEEDLE (coded to PT "injection site urticaria") of mild intensity. No corrective treatment was given and the event was recovered after 7 days. The event was not considered as related to IP. From Day 264 until Day 368 after start of IP intake the patient had intermittently stopped IP administration for one day. From day 369 to day 386 the patient did not administer the IP. From day 387 to day 393 the patient again injected 20 μg of IP each day. Then, again IP administration was stopped for 2 days and injected for the last time on day 396. IP was permanently stopped due to a non-serious TEAE of mild intensity REOCCURING WELTS AFTER RESTARTING STUDY MEDICATION (coded to PT "urticaria") on day 396 day after start of IP administration. This event was considered as related to IP. The event resolved 11 days after last administration of IP without any corrective treatment. Both events were sent to ARAC for adjudication but only the $2^{nd}$ event was adjudicated by ARAC as an allergic reaction urticaria (hives), possibly related to the IP.

Patient 642701006 (lixisenatide group): This patient without a history of allergy experienced on Day 163 (Oct. 1, 2009) after start of LP a non-serious TEAE of ALLERGY (coded to PT "hypersensitivity") of mild intensity. Thirty minutes after injection of the IP, the patient complained about generalized itch and redness of the eyes, which spontaneously disappeared without treatment. The event resolved the same day. On day 169 after start of IP, a non-serious TEAE of ALLERGIC DERMATITIS (coded to PT "dermatitis allergic") of moderate intensity was reported. Twenty-five minutes after administration of IP, the patient complained about generalized itch, swelling of eyes and tongue and swelling at the injection site. The event resolved on the same day. Oral loratadine was started on day 169 after start of IP and given as corrective treatment for 7 days. On day 170 after start of IP, another non-serious TEAE of ALLERGIC DERMATITIS (coded to PT "dermatitis allergic") of moderate intensity was reported and resolved the same day. Immediately after administration of IP, the patient complained about swelling at the injection site, generalized itch, generalized rush, swelling of the eyes and tongue, nausea. All 3 events were considered as related to IP and IP was permanently stopped due to the third event after day 170. The 3 events were adjudicated by ARAC as allergic reactions (allergic conjunctivitis, angioedema and anaphylactic reaction respectively), possibly related to the IP.

Patient 840864001 (lixisenatide group): with a medical history of allergic rhinitis, pollen allergies, dust allergies, swelling (angioedema), drug allergies, rush and dermatitis, experienced a non-serious TEAE of DERMATITIS ON BILATERAL ARMS AND ABDOMEN (coded to PT "dermatitis") of moderate intensity on the third day after start of IP administration. Clindamycin was given as corrective treatment for three days. IP administration was temporarily stopped on Day 5 until Day 8 after start of IP administration. A re-challenge with IP on Day 9 to Day 13 caused a worsening on the abdominal wall. The event was considered as related to IP and the IP was permanently stopped after day 13. The event resolved 12 days (21 Dec. 2009) after permanent discontinuation from IP. This TEAE was adjudicated by ARAC as an allergic reaction (allergic dermatitis), possibly related to IP.

No event was adjudicated by ARAC as possibly related to IP in the placebo group.

Per protocol, any increase in amylase and/or lipase above twice the upper limit of normal range (ULN) that had been confirmed by a repeat measurement was to be monitored and documented on a pre-specified AE form for "suspected pancreatitis". During the on-treatment period of the whole study, 2 (0.6%) patients in the lixisenatide group and 2 (1.2%) in the placebo group reported TEAEs with the pre-specified AE form (Table 24). No case of pancreatitis was diagnosed or reported.

Patients who had at least one value of lipase or amylase ≥3 ULN during the on-treatment period are summarized in (Table 25). A total of 7 patients experienced elevated lipase (3ULN): 5 [1.6%] in the lixisenatide group, 2 [1.3%] in the placebo group. No one had elevated amylase ≥3ULN.

Per protocol, any calcitonin value ≥20 µg/mL confirmed by a repeat measurement was to be monitored and reported on the pre-specified AE form for "increased calcitonin ≥20 pg/mL" During the on-treatment period of the whole study, 9 (2.8%) patients in the lixisenatide group and 4 (2.5%) in the placebo group reported increased blood calcitonin on the pre-specified AE form (Table 26). Among them, 8 out of 9 patients in the lixisenatide group had calcitonin values ≥20 but <50 ng/L and 1 patient had a calcitonin value ≥50 ng/L, whereas in the placebo group 3 out of 4 patients had calcitonin values ≥20 but <50 ng/L and 1 patient had calcitonin values ≥50 ng/L. One additional patient in the lixisenatide group reported a post-treatment AE on the pre-specified adverse event form for "increased calcitonin 20 pg/mL" with calcitonin values ≥20 but <50 ng/L. Two patients in the lixisenatide group and 1 patient in the placebo group reported AEs that were coded to PT "thyroid neoplasm".

Patient 642706001 (lixisenatide group): a non-smoker, without a history of thyroid disease and without renal insufficiency, experienced a non-serious adverse event LEFT THYROID LOBE NODULE of mild intensity twenty-four days after last administration of IP. No thyroid medication was given. The event was considered as not related to IP. At Visit 15, 255 days after start of IP, calcitonin was measured for the first time and was 16.4 ng/L. At the last day of IP, calcitonin was 22.2 ng/L and in the re-test one week later 18.9 ng/L.

Patient 840738004 (lixisenatide group): a former smoker of 35 years, without a history of thyroid disease and without renal insufficiency experienced a non serious TEAE of 6 mm THYROID NODULE LEFT LOBE of mild intensity 39 days after first intake of IP. No thyroid medication was given. A thyroid ultrasound 177 days after first intake of IP confirmed a 7×3 mm nodule in the left lobe. The first calcitonin at start of IP intake was 19.7 ng/L. Two-hundred sixty-two days after first intake of IP a non-serious TEAE ELEVATED CALCITONIN of mild intensity was reported on the specific pages for increased calcitonin due to a calcitonin value of 20.1 ng/L. The event ELEVATED CALCITONIN was resolved without treatment 376 days after first intake of IP. Nine days before, calcitonin was 16.3 ng/L. At the last day of IP intake, calcitonin was 19.4 ng/L. Both events were considered as not related to IP.

Patients with at least one serum calcitonin measurement during the on-treatment period of the whole study are summarized in Table 27 according to the 4 pre-defined categories of calcitonin level at baseline. A total of 17 patients had calcitonin values ≥20 ng/L during the on-treatment period of the whole study: 11 (3.7%) patients in the lixisenatide group, 6 (4.2%) patients in the placebo group. Among them, 13 patients (9 for lixisenatide and 4 for placebo) reported a TEAE with the pre-specified AE form as described above. Two patients in each treatment group had at least 1 calcitonin value ≥20 ng/L but did not report a TEAE with the pre-specified AE form during the on-treatment period of the whole study. For one patient who had multiple values ≥20 but <50 ng/L in the placebo group this was due to measurements done before protocol amendment 4 which required the retesting. For the other 3 patients this was because of an unconfirmed calcitonin elevation: 1 patient in each group had a single value ≥20 but <50 ng/L and 1 in the lixisenatide group had a single value ≥50 ng/L, but their other pre- and/or post-measurements were <20 ng/L. Since calcitonin measurements were implemented in a protocol amendment after most patients were already randomized in this study. Therefore, baseline calcitonin values were not available for most patients.

One patient in the placebo group and 2 patients in the lixisenatide group had a calcitonin value >50 ng/L (Table 27).

Patient 840782004 (lixisenatide group): a non-smoker, without thyroid diseases in the medical history and without renal insufficiency, on the day of the first IP administration (Aug. 3, 2009) calcitonin was 37.8 ng/L and a non-serious TEAE of CALCITONIN ELEVATION of mild intensity was reported one day later. IP was continued. No corrective treatment was given. A thyroid ultrasound was not performed. The event was considered as related to IP. The further calcitonin values during the study were 64.2, 19.3, 50, 36.5 and on Day 260 (Apr. 19, 2010) after start of IP it was 29.6 ng/L. Forty-three days (Aug. 24, 2010) after permanent discontinuation of IP (due to lack of efficacy), calcitonin was 48.1 ng/L.

Patient 040702004 (lixisenatide group): had a calcitonin value of 104 ng/L at one visit during the study. At the re-test 14 days later, calcitonin was 3 ng/L. Because at all earlier and later visits during the study calcitonin values were between <0.6 ng/L and 3 ng/L no TEAE referring to calcitonin was reported and no further thyroid investigation performed.

TABLE 21

Summary of symptomatic hypoglycemia during the on-treatment period of the whole study - Safety population

| Type | Placebo (N = 161) | Lixisenatide (N = 323) |
|---|---|---|
| Total patient years | 227.6 | 493.9 |
| Any symptomatic hypoglycemia | | |
| Number of patients with events, n (%) | 7 (4.3%) | 23 (7.1%) |
| Number of patients with events per 100 patient years[a] | 3.1 | 4.7 |
| Blood glucose <60 mg/dL | | |
| Number of patients with events, n (%) | 7 (4.3%) | 17 (5.3%) |
| Number of patients with events per 100 patient years[a] | 3.1 | 3.4 |
| No blood glucose reported | | |
| Number of patients with events, n (%) | 0 | 9 (2.8%) |
| Number of patients with events per 100 patient years[a] | 0.0 | 1.8 |

[a]Calculated as (number of patients with events*100 divided by total exposure + 3 days in patient years).
Symptomatic hypoglycemia = Symptomatic hypoglycemia as defined per protocol.
Note:
on-treatment period of the whole study = the time from the first dose of double-blind study medication up to 3 days after the last dose administration.

TABLE 22

Number (%) of patients experiencing injection site reactions during the on-treatment period of the whole study-Safety population

| Event source Preferred Term | Placebo (N = 161) | Lixisenatide (N = 323) |
|---|---|---|
| Any injection site reactions | 8 (5.0%) | 22 (6.8%) |
| Investigator reported PTs | 7 (4.3%) | 22 (6.8%) |
| Injection site pain | 4 (2.5%) | 5 (1.5%) |
| Injection site haematoma | 3 (1.9%) | 8 (2.5%) |
| Injection site reaction | 1 (0.6%) | 4 (1.2%) |
| Injection site swelling | 1 (0.6%) | 0 |
| Injection site erythema | 0 | 5 (1.5%) |
| Injection site haemorrhage | 0 | 1 (0.3%) |
| Injection site hypersensitivity | 0 | 1 (0.3%) |
| Injection site mass | 0 | 1 (0.3%) |
| Injection site pruritus | 0 | 4 (1.2%) |
| Injection site rash | 0 | 1 (0.3%) |
| Injection site urticaria | 0 | 2 (0.6%) |
| PTs by ARAC diagnosis | 3 (1.9%) | 7 (2.2%) |
| Injection site reaction | 3 (1.9%) | 7 (2.2%) |

ARAC = Allergic Reaction Assessment Committee.
Note:
on-treatment period of the whole study = the time from the first dose of double-blind study medication up to 3 days after the last dose administration.

TABLE 23

Number (%) of patients with events adjudicated as an allergic reaction by ARAC during the on-treatment period of the whole study - Safety population

| Relationship to study treatment (by ARAC) | MedDRA coded term (PT) for ARAC diagnosis | ARAC diagnosis | Placebo (N = 161) | Lixisenatide (N = 323) |
|---|---|---|---|---|
| All | Events adjudicated as an allergic reaction by ARAC | | 3 (1.9%) | 9 (2.8%) |
| | Anaphylactic reaction | Anaphylactic reaction | 0 | 1 (0.3%) |
| | Angioedema | Angioedema | 1 (0.6%) | 1 (0.3%) |
| | Conjunctivitis | Allergic conjunctivitis | 0 | 1 (0.3%) |
| | Conjunctivitis | Conjunctivitis | 0 | 1 (0.3%) |
| | Dermatitis allergic | Allergic dermatitis | 0 | 1 (0.3%) |
| | Dermatitis contact | Allergic contact dermatitis | 1 (0.6%) | 2 (0.6%) |
| | Dermatitis contact | Allergic contact dermatitis (poison ivy) | 0 | 1 (0.3%) |
| | Dermatitis contact | Contact dermatitis (poison ivy) | 1 (0.6%) | 0 |
| | Drug eruption | Allergic dermatitis to glypizide | 0 | 1 (0.3%) |
| | Pruritus generalised | Generalized itch | 1 (0.6%) | 0 |
| | Rhinitis allergic | Allergic rhinitis | 0 | 1 (0.3%) |
| | Rhinitis | Rhinitis | 0 | 1 (0.3%) |
| | Urticaria | Urticaria (hives) | 0 | 1 (0.3%) |
| Related | Events adjudicated as an allergic reaction by ARAC | | 0 | 3 (0.9%) |
| | Anaphylactic reaction | Anaphylactic reaction | 0 | 1 (0.3%) |
| | Angioedema | Angioedema | 0 | 1 (0.3%) |
| | Conjunctivitis allergic | Allergic conjunctivitis | 0 | 1 (0.3%) |
| | Dermatitis allergic | Allergic dermatitis | 0 | 1 (0.3%) |
| | Urticaria | Urticaria (hives) | 0 | 1 (0.3%) |
| Not related | Events adjudicated as an allergic reaction by ARAC | | 3 (1.9%) | 6 (1.9%) |
| | Angioedema | Angioedema | 1 (0.6%) | 0 |
| | Conjunctivitis | Conjunctivitis | 0 | 1 (0.3%) |
| | Dermatitis contact | Allergic contact dermatitis | 1 (0.6%) | 2 (0.6%) |
| | Dermatitis contact | Allergic contact dermatitis (poison ivy) | 0 | 1 (0.3%) |
| | Dermatitis contact | Contact dermatitis (poison ivy) | 1 (0.6%) | 0 |
| | Drug eruption | Allergic dermatitis to glypizide | 0 | 1 (0.3%) |
| | Pruritus generalised | Generalized itch | 1 (0.6%) | 0 |
| | Rhinitis allergic | Allergic rhinitis | 0 | 1 (0.3%) |
| | Rhinitis | Rhinitis | 0 | 1 (0.3%) |

ARAC = Allergic Reaction Assessment Committee. IP = Investigational Product.
Note:
on-treatment period of the whole study = the time from the first dose of double-blind study medication up to 3 days after the last dose administration.

TABLE 24

Number (%) of patients with a specific adverse event form for suspected pancreatitis completed during the on-treatment period of the whole study - Safety population

| Preferred Term | Placebo (N = 161) | Lixisenatide (N = 323) |
|---|---|---|
| Any | 2 (1.2%) | 2 (0.6%) |
| Blood amylase increased | 1 (0.6%) | 2 (0.6%) |
| Lipase increased | 2 (1.2%) | 2 (0.6%) | n (%) = number and percentage of patients with any cases reported on the AE form for suspected pancreatitis along with complementary form.
Note:
on-treatment period of the whole study = the time from the first dose of double-blind study medication up to 3 days after the last dose administration.

TABLE 25

Pancreatic enzymes: Number (%) of patients with abnormalities (PCSA) during the on-treatment period of the whole study according to baseline PCSA status - Safety population

| Laboratory parameter Baseline By PCSA criteria n/N1 (%) | Placebo (N = 161) | Lixisenatide (N = 323) |
|---|---|---|
| Lipase (IU/L) | | |
| Total* | | |
| ≥3 ULN | 2/160 (1.3%) | 5/317 (1.6%) |
| Normal/Missing | | |
| ≥3 ULN | 2/159 (1.3%) | 5/317 (1.6%) |
| Amylase (IU/L) | | |
| Total* | | |
| ≥3 ULN | 0/160 | 0/317 |
| Normal/Missing | | |
| ≥3 ULN | 0/160 | 0/317 |

PCSA: Potentially Clinically Significant Abnormalities, ULN = Upper limit of normal.
*Regardless of baseline.
Note:
on-treatment period of the whole study = the time from the first dose of double-blind study medication up to 3 days after the last dose administration.
The number (n) represents the subset of the total number of patients who met the criterion in question at least once.
The denominator (/N1) for each parameter within a treatment group is the number of patients for the treatment group who had that parameter assessed post-baseline by baseline PCSA status. Only the worsening of the worst case for each patient is presented by baseline status.

TABLE 26

Number (%) of patients with increased calcitonin during the on-treatment period of the whole study - Safety population

| Preferred Term | Placebo (N = 161) | Lixisenatide (N = 323) |
|---|---|---|
| Any | 4 (2.5%) | 9 (2.8%) |
| Blood calcitonin increased | 4 (2.5%) | 9 (2.8%) | n (%) = number and percentage of patients with any cases reported on the AE form for increased calcitonin ≥20 ng/L.
Note:
on-treatment period of the whole study = the time from the first dose of double-blind study medication up to 3 days after the last dose administration.

TABLE 27

Serum calcitonin: Number (%) of patients by pre-defined categories during the on-treatment period of the whole study according to baseline category - Safety population

| Laboratory criteria Baseline status Post-baseline | Placebo (N = 161) | Lixisenatide (N = 323) |
|---|---|---|
| Calcitonin (ng/L) | | |
| Total* | | |
| ≤ULN | 117/144 (81.3%) | 265/303 (87.5%) |
| >ULN-<20 ng/L | 21/144 (14.6%) | 27/303 (8.9%) |

TABLE 27-continued

Serum calcitonin: Number (%) of patients by pre-defined categories during the on-treatment period of the whole study according to baseline category - Safety population

| Laboratory criteria Baseline status Post-baseline | Placebo (N = 161) | Lixisenatide (N = 323) |
|---|---|---|
| ≥20 ng/L-<50 ng/L | 5/144 (3.5%) | 9/303 (3.0%) |
| ≥50 ng/L | 1/144 (0.7%) | 2/303 (0.7%) |
| Missing | | |
| ≤ULN | 72/83 (86.7%) | 161/178 (90.4%) |
| >ULN-<20 ng/L | 8/83 (9.6%) | 12/178 (6.7%) |
| ≥20 ng/L-<50 ng/L | 3/83 (3.6%) | 5/178 (2.8%) |
| ≥50 ng/L | 0/83 | 0/178 |
| ≤ULN | | |
| ≤ULN | 44/53 (83.0%) | 104/110 (94.5%) |
| >ULN-<20 ng/L | 9/53 (17.0%) | 5/110 (4.5%) |
| ≥20 ng/L-<50 ng/L | 0/53 | 0/110 |
| ≥50 ng/L | 0/53 | 1/110 (0.9%) |
| >ULN-<20 ng/L | | |
| ≤ULN | 1/5 (20.0%) | 0/12 |
| >ULN-<20 ng/L | 4/5 (80.0%) | 10/12 (83.3%) |
| ≥20 ng/L-<50 ng/L | 0/5 | 2/12 (16.7%) |
| ≥50 ng/L | 0/5 | 0/12 |
| ≥20 ng/L-<50 ng/L | | |
| ≤ULN | 0/3 | 0/3 |
| >ULN-<20 ng/L | 0/3 | 0/3 |
| ≥20 ng/L-<50 ng/L | 2/3 (66.7%) | 2/3 (66.7%) |
| ≥50 ng/L | 1/3 (33.3%) | 1/3 (33.3%) |
| ≥50 ng/L | | |
| ≤ULN | 0/0 | 0/0 |
| >ULN-<20 ng/L | 0/0 | 0/0 |
| ≥20 ng/L-<50 ng/L | 0/0 | 0/0 |
| ≥50 ng/L | 0/0 | 0/0 |

ULN = Upper limit of normal
*Regardless of baseline.
Note:
on-treatment period of the whole study = the time from the first dose of double-blind study medication up to 3 days after the last dose administration.
The numerator represents the number of patients who were in the pre-specified categories at post-baseline in each baseline category. The denominator for each parameter within a treatment group is the number of patients for the treatment group who had that parameter assessed post-baseline by baseline status.
A patient is counted only in the worst category.

7 APPENDIX

TABLE 28

Number (%) of patients by total daily dose at the end of titration - Safety population

| Dose at the end of titration | Placebo (N = 161) | Lixisenatide (N = 323) |
|---|---|---|
| 10 μg | 1 (0.6%) | 13 (4.0%) |
| 15 μg | 5 (3.1%) | 21 (6.5%) |
| 20 μg | 155 (96.3%) | 289 (89.5%) |

Dose = Dose of active drug or volume-matched placebo.
The scheduled visit for end of titration per protocol would be Visit 5/Week 2.
Note:
Percentages are calculated using the number of safety patients as the denominator.

TABLE 29

Mean change in HbA1c (%) from baseline by visit - mITT

| Treatment Time point | Observed data | | | | | | | Change from baseline | | | | | | |
|---|---|---|---|---|---|---|---|---|---|---|---|---|---|---|
| | N | Mean | SD | SE | Median | Min | Max | N | Mean | SD | SE | Median | Min | Max |
| Placebo (N = 159) | | | | | | | | | | | | | | |
| Screening | 159 | 8.14 | 0.82 | 0.065 | 8.00 | 7.0 | 10.0 | | | | | | | |
| Baseline | 159 | 8.06 | 0.79 | 0.063 | 7.90 | 6.5 | 10.2 | | | | | | | |
| Week 8 | 144 | 7.74 | 0.83 | 0.069 | 7.55 | 6.3 | 10.2 | 144 | −0.31 | 0.75 | 0.062 | −0.30 | −2.2 | 2.3 |
| Week 12 | 141 | 7.67 | 0.95 | 0.080 | 7.60 | 6.0 | 10.4 | 141 | −0.39 | 0.89 | 0.075 | −0.40 | −2.6 | 2.7 |
| Week 24 | 123 | 7.44 | 0.86 | 0.077 | 7.30 | 5.5 | 10.1 | 123 | −0.57 | 0.93 | 0.084 | −0.40 | −4.0 | 1.6 |
| Week 24 (LOCF) | 148 | 7.59 | 0.96 | 0.079 | 7.40 | 5.5 | 10.4 | 148 | −0.46 | 1.00 | 0.082 | −0.40 | −4.0 | 2.5 |
| Week 36 | 100 | 7.22 | 0.82 | 0.082 | 7.10 | 5.1 | 9.7 | 100 | −0.77 | 0.99 | 0.099 | −0.70 | −4.4 | 1.6 |
| Week 44 | 90 | 7.16 | 0.73 | 0.077 | 7.10 | 5.3 | 8.9 | 90 | −0.77 | 0.92 | 0.097 | −0.70 | −3.9 | 1.4 |
| Week 52 | 86 | 7.17 | 0.75 | 0.081 | 7.20 | 5.5 | 8.9 | 86 | −0.74 | 0.92 | 0.100 | −0.70 | −3.9 | 1.4 |
| Week 60 | 80 | 7.22 | 0.76 | 0.085 | 7.20 | 5.7 | 9.1 | 80 | −0.67 | 0.97 | 0.109 | −0.50 | −3.8 | 1.6 |
| Week 68 | 72 | 7.21 | 0.87 | 0.103 | 7.20 | 5.8 | 10.0 | 72 | −0.66 | 1.03 | 0.121 | −0.65 | −3.6 | 1.5 |
| Week 76 | 71 | 7.25 | 0.97 | 0.115 | 7.10 | 5.3 | 11.0 | 71 | −0.62 | 1.07 | 0.127 | −0.70 | −3.9 | 2.0 |
| Week 84 | 48 | 7.26 | 1.19 | 0.172 | 7.10 | 5.4 | 11.9 | 48 | −0.58 | 1.11 | 0.160 | −0.70 | −2.7 | 2.9 |
| Week 92 | 30 | 7.13 | 0.78 | 0.143 | 7.15 | 5.2 | 9.9 | 30 | −0.67 | 0.86 | 0.156 | −0.75 | −3.0 | 1.5 |
| Week 100 | 22 | 7.20 | 0.82 | 0.176 | 7.35 | 4.7 | 9.0 | 22 | −0.69 | 0.78 | 0.167 | −0.55 | −2.4 | 0.9 |
| Week 108 | 8 | 7.31 | 0.67 | 0.238 | 7.50 | 6.3 | 8.2 | 8 | −0.65 | 0.98 | 0.347 | −0.60 | −2.5 | 0.4 |
| Week 116 | 4 | 7.55 | 0.70 | 0.352 | 7.45 | 6.8 | 8.5 | 4 | −0.25 | 0.76 | 0.380 | −0.25 | −1.0 | 0.5 |
| Week 124 | 2 | 7.30 | 1.13 | 0.800 | 7.30 | 6.5 | 8.1 | 2 | −0.50 | 0.85 | 0.600 | −0.50 | −1.1 | 0.1 |
| Week 132 | 1 | 6.70 | NC | NC | 6.70 | 6.7 | 6.7 | 1 | −0.90 | NC | NC | −0.90 | −0.9 | −0.9 |
| Last on-treatment value | 148 | 7.74 | 1.09 | 0.090 | 7.70 | 4.7 | 11.9 | 148 | −0.30 | 1.12 | 0.092 | −0.30 | −3.9 | 2.9 |
| Lixisenatide (N = 320) | | | | | | | | | | | | | | |
| Screening | 319 | 8.15 | 0.83 | 0.046 | 8.00 | 7.0 | 10.0 | | | | | | | |
| Baseline | 320 | 8.08 | 0.90 | 0.050 | 7.90 | 6.5 | 12.7 | | | | | | | |
| Week 8 | 293 | 7.30 | 0.82 | 0.048 | 7.10 | 5.5 | 10.9 | 293 | −0.78 | 0.80 | 0.047 | −0.70 | −6.0 | 3.2 |
| Week 12 | 285 | 7.12 | 0.88 | 0.052 | 6.90 | 5.3 | 12.2 | 285 | −0.97 | 0.93 | 0.055 | −0.90 | −5.1 | 3.1 |
| Week 24 | 276 | 6.92 | 0.82 | 0.050 | 6.80 | 5.3 | 11.3 | 276 | −1.16 | 1.02 | 0.061 | −1.00 | −5.4 | 3.1 |
| Week 24 (LOCF) | 308 | 7.06 | 0.96 | 0.055 | 6.90 | 5.3 | 11.3 | 308 | −1.02 | 1.09 | 0.062 | −0.90 | −5.4 | 3.5 |
| Week 36 | 242 | 6.80 | 0.80 | 0.051 | 6.75 | 5.2 | 11.4 | 242 | −1.23 | 1.03 | 0.066 | −1.10 | −5.7 | 2.3 |
| Week 44 | 231 | 6.81 | 0.72 | 0.047 | 6.80 | 5.3 | 9.4 | 231 | −1.23 | 0.99 | 0.065 | −1.10 | −5.8 | 1.3 |
| Week 52 | 223 | 6.84 | 0.73 | 0.049 | 6.80 | 5.2 | 9.4 | 223 | −1.17 | 0.97 | 0.065 | −1.00 | −5.6 | 1.1 |
| Week 60 | 203 | 6.81 | 0.67 | 0.047 | 6.80 | 5.1 | 9.1 | 203 | −1.18 | 0.95 | 0.067 | −1.00 | −5.8 | 0.6 |
| Week 68 | 207 | 6.84 | 0.72 | 0.050 | 6.80 | 4.6 | 9.5 | 207 | −1.17 | 1.07 | 0.075 | −0.90 | −6.1 | 2.1 |
| Week 76 | 194 | 6.87 | 0.74 | 0.053 | 6.80 | 4.8 | 9.5 | 194 | −1.13 | 1.04 | 0.075 | −1.05 | −5.8 | 1.5 |
| Week 84 | 142 | 6.91 | 0.78 | 0.065 | 6.80 | 5.5 | 10.2 | 142 | −1.04 | 1.05 | 0.088 | −0.90 | −5.9 | 2.6 |
| Week 92 | 114 | 6.96 | 0.72 | 0.068 | 6.90 | 5.2 | 9.0 | 114 | −0.99 | 1.00 | 0.094 | −0.80 | −6.0 | 2.1 |
| Week 100 | 87 | 7.08 | 0.82 | 0.088 | 7.00 | 5.7 | 10.3 | 87 | −0.97 | 1.11 | 0.119 | −0.85 | −6.1 | 2.1 |
| Week 108 | 46 | 6.86 | 0.63 | 0.093 | 6.80 | 5.6 | 8.3 | 46 | −1.26 | 0.97 | 0.143 | −1.00 | −3.9 | 0.8 |
| Week 116 | 20 | 7.06 | 0.73 | 0.162 | 6.85 | 6.1 | 8.6 | 20 | −0.97 | 0.91 | 0.203 | −0.80 | −3.0 | 0.3 |
| Week 124 | 6 | 7.47 | 1.11 | 0.455 | 7.55 | 6.1 | 8.8 | 6 | −0.98 | 0.52 | 0.210 | −0.95 | −1.9 | −0.5 |
| Last on-treatment value | 308 | 7.33 | 1.09 | 0.062 | 7.20 | 4.8 | 11.3 | 308 | −0.75 | 1.20 | 0.068 | −0.70 | −6.0 | 3.5 |

NC = Not computable.
LOCF = Last observation carried forward.
Note:
The analysis excludes measurements obtained after the introduction of rescue medication and/or after the treatment cessation plus 3 days.
For Week 24 (LOCF), the analysis includes measurements obtained up to 3 days after the last dose of the double-blind investigational product injection on or before Visit 12 (Week24), or Day 169 if Visit 12 (Week 24) is not available.

TABLE 30

Number (%) of patients experiencing common TEAE(s) (PT ≥1% in any treatment group) presented by primary SOC, HLGT, HLT and PT during the on-treatment period of the whole study - Safety population

| PRIMARY SYSTEM ORGAN CLASS HLGT: High Level Group Term HLT: High Level Term Preferred Term | Placebo (N = 161) | Lixisenatide (N = 323) |
|---|---|---|
| Any class | 134 (83.2%) | 284 (87.9%) |
| INFECTIONS AND INFESTATIONS | 77 (47.8%) | 173 (53.6%) |
| HLGT: Bacterial infectious disorders | 12 (7.5%) | 8 (2.5%) |
| HLT: Bacterial infections NEC | 8 (5.0%) | 8 (2.5%) |
| Cellulitis | 5 (3.1%) | 6 (1.9%) |
| HLT: Streptococcal infections | 4 (2.5%) | 0 |
| Pharyngitis streptococcal | 4 (2.5%) | 0 |
| HLGT: Fungal infectious disorders | 6 (3.7%) | 10 (3.1%) |
| HLT: Tinea infections | 3 (1.9%) | 3 (0.9%) |
| Tinea pedis | 3 (1.9%) | 2 (0.6%) |

TABLE 30-continued

Number (%) of patients experiencing common TEAE(s) (PT ≥1% in any treatment group) presented by primary SOC, HLGT, HLT and PT during the on-treatment period of the whole study - Safety population

| PRIMARY SYSTEM ORGAN CLASS<br>HLGT: High Level Group Term<br>HLT: High Level Term<br>Preferred Term | Placebo<br>(N = 161) | Lixisenatide<br>(N = 323) |
|---|---|---|
| HLGT: Infections - pathogen unspecified | 66 (41.0%) | 152 (47.1%) |
| HLT: Abdominal and gastrointestinal infections | 4 (2.5%) | 11 (3.4%) |
| Gastroenteritis | 2 (1.2%) | 8 (2.5%) |
| HLT: Dental and oral soft tissue infections | 2 (1.2%) | 7 (2.2%) |
| Tooth abscess | 2 (1.2%) | 2 (0.6%) |
| HLT: Ear infections | 7 (4.3%) | 6 (1.9%) |
| Ear infection | 6 (3.7%) | 2 (0.6%) |
| HLT: Infections NEC | 2 (1.2%) | 12 (3.7%) |
| Localised infection | 2 (1.2%) | 1 (0.3%) |
| Respiratory tract infection | 0 | 5 (1.5%) |
| HLT: Lower respiratory tract and lung infections | 24 (14.9%) | 28 (8.7%) |
| Bronchitis | 17 (10.6%) | 25 (7.7%) |
| Lower respiratory tract infection | 4 (2.5%) | 1 (0.3%) |
| Pneumonia | 5 (3.1%) | 2 (0.6%) |
| HLT: Skin structures and soft tissue infections | 3 (1.9%) | 8 (2.5%) |
| Furuncle | 2 (1.2%) | 3 (0.9%) |
| HLT: Upper respiratory tract infections | 47 (29.2%) | 107 (33.1%) |
| Acute sinusitis | 2 (1.2%) | 5 (1.5%) |
| Nasopharyngitis | 24 (14.9%) | 53 (16.4%) |
| Pharyngitis | 5 (3.1%) | 7 (2.2%) |
| Sinusitis | 8 (5.0%) | 16 (5.0%) |
| Upper respiratory tract infection | 18 (11.2%) | 41 (12.7%) |
| HLT: Urinary tract infections | 11 (6.8%) | 30 (9.3%) |
| Urinary tract infection | 11 (6.8%) | 24 (7.4%) |
| HLGT: Viral infectious disorders | 15 (9.3%) | 40 (12.4%) |
| HLT: Influenza viral infections | 9 (5.6%) | 24 (7.4%) |
| Influenza | 9 (5.6%) | 24 (7.4%) |
| HLT: Viral infections NEC | 5 (3.1%) | 11 (3.4%) |
| Gastroenteritis viral | 3 (1.9%) | 9 (2.8%) |
| BLOOD AND LYMPHATIC SYSTEM DISORDERS | 3 (1.9%) | 12 (3.7%) |
| HLGT: Anaemias nonhaemolytic and marrow depression | 1 (0.6%) | 9 (2.8%) |
| HLT: Anaemias NEC | 1 (0.6%) | 8 (2.5%) |
| Anaemia | 1 (0.6%) | 7 (2.2%) |
| IMMUNE SYSTEM DISORDERS | 3 (1.9%) | 5 (1.5%) |
| HLGT: Allergic conditions | 3 (1.9%) | 5 (1.5%) |
| HLT: Atopic disorders | 2 (1.2%) | 2 (0.6%) |
| Seasonal allergy | 2 (1.2%) | 2 (0.6%) |
| ENDOCRINE DISORDERS | 2 (1.2%) | 3 (0.9%) |
| HLGT: Thyroid gland disorders | 2 (1.2%) | 3 (0.9%) |
| HLT: Thyroid hypofunction disorders | 2 (1.2%) | 0 |
| Hypothyroidism | 2 (1.2%) | 0 |
| METABOLISM AND NUTRITION DISORDERS | 26 (16.1%) | 65 (20.1%) |
| HLGT: Appetite and general nutritional disorders | 5 (3.1%) | 14 (4.3%) |
| HLT: Appetite disorders | 5 (3.1%) | 14 (4.3%) |
| Decreased appetite | 4 (2.5%) | 13 (4.0%) |
| HLGT: Glucose metabolism disorders (incl diabetes mellitus) | 12 (7.5%) | 27 (8.4%) |
| HLT: Hyperglycaemic conditions NEC | 3 (1.9%) | 2 (0.6%) |
| Hyperglycaemia | 3 (1.9%) | 2 (0.6%) |
| HLT: Hypoglycaemic conditions NEC | 9 (5.6%) | 26 (8.0%) |
| Hypoglycaemia | 8 (5.0%) | 25 (7.7%) |
| HLGT: Lipid metabolism disorders | 6 (3.7%) | 8 (2.5%) |
| HLT: Elevated triglycerides | 2 (1.2%) | 3 (0.9%) |
| Hypertriglyceridaemia | 2 (1.2%) | 3 (0.9%) |
| HLT: Hyperlipidaemias NEC | 2 (1.2%) | 1 (0.3%) |
| Hyperlipidaemia | 2 (1.2%) | 1 (0.3%) |
| HLT: Lipid metabolism and deposit disorders NEC | 1 (0.6%) | 5 (1.5%) |
| Dyslipidaemia | 1 (0.6%) | 5 (1.5%) |
| HLGT: Purine and pyrimidine metabolism disorders | 3 (1.9%) | 8 (2.5%) |
| HLT: Disorders of purine metabolism | 3 (1.9%) | 8 (2.5%) |
| Gout | 2 (1.2%) | 2 (0.6%) |
| Hyperuricaemia | 1 (0.6%) | 6 (1.9%) |
| PSYCHIATRIC DISORDERS | 14 (8.7%) | 31 (9.6%) |
| HLGT: Anxiety disorders and symptoms | 4 (2.5%) | 9 (2.8%) |
| HLT: Anxiety symptoms | 4 (2.5%) | 7 (2.2%) |
| Anxiety | 2 (1.2%) | 5 (1.5%) |
| Stress | 2 (1.2%) | 2 (0.6%) |
| HLGT: Depressed mood disorders and disturbances | 7 (4.3%) | 13 (4.0%) |
| HLT: Depressive disorders | 7 (4.3%) | 12 (3.7%) |
| Depression | 7 (4.3%) | 12 (3.7%) |
| HLGT: Sleep disorders and disturbances | 4 (2.5%) | 6 (1.9%) |
| HLT: Disturbances in initiating and maintaining sleep | 4 (2.5%) | 5 (1.5%) |
| Insomnia | 4 (2.5%) | 5 (1.5%) |

TABLE 30-continued

Number (%) of patients experiencing common TEAE(s) (PT ≥1% in any treatment group) presented by primary SOC, HLGT, HLT and PT during the on-treatment period of the whole study - Safety population

| PRIMARY SYSTEM ORGAN CLASS<br>HLGT: High Level Group Term<br>HLT: High Level Term<br>Preferred Term | Placebo<br>(N = 161) | Lixisenatide<br>(N = 323) |
|---|---|---|
| NERVOUS SYSTEM DISORDERS | 44 (27.3%) | 98 (30.3%) |
| HLGT: Headaches | 20 (12.4%) | 44 (13.6%) |
| HLT: Headaches NEC | 19 (11.8%) | 44 (13.6%) |
| Headache | 19 (11.8%) | 43 (13.3%) |
| HLT: Migraine headaches | 3 (1.9%) | 0 |
| Migraine | 3 (1.9%) | 0 |
| HLGT: Movement disorders (incl parkinsonism) | 2 (1.2%) | 3 (0.9%) |
| HLT: Tremor (excl congenital) | 2 (1.2%) | 2 (0.6%) |
| Tremor | 2 (1.2%) | 2 (0.6%) |
| HLGT: Neurological disorders NEC | 22 (13.7%) | 48 (14.9%) |
| HLT: Neurological signs and symptoms NEC | 13 (8.1%) | 34 (10.5%) |
| Dizziness | 13 (8.1%) | 33 (10.2%) |
| HLT: Paraesthesias and dysaesthesias | 6 (3.7%) | 8 (2.5%) |
| Paraesthesia | 5 (3.1%) | 5 (1.5%) |
| HLT: Sensory abnormalities NEC | 5 (3.1%) | 5 (1.5%) |
| Hypoaesthesia | 4 (2.5%) | 3 (0.9%) |
| HLGT: Peripheral neuropathies | 6 (3.7%) | 10 (3.1%) |
| HLT: Peripheral neuropathies NEC | 3 (1.9%) | 4 (1.2%) |
| Neuropathy peripheral | 3 (1.9%) | 3 (0.9%) |
| HLGT: Spinal cord and nerve root disorders | 0 | 7 (2.2%) |
| HLT: Lumbar spinal cord and nerve root disorders | 0 | 5 (1.5%) |
| Sciatica | 0 | 5 (1.5%) |
| EYE DISORDERS | 10 (6.2%) | 26 (8.0%) |
| HLGT: Anterior eye structural change, deposit and degeneration | 2 (1.2%) | 7 (2.2%) |
| HLT: Cataract conditions | 2 (1.2%) | 7 (2.2%) |
| Cataract | 2 (1.2%) | 7 (2.2%) |
| HLGT: Ocular infections, irritations and inflammations | 1 (0.6%) | 8 (2.5%) |
| HLT: Conjunctival infections, irritations and inflammations | 0 | 6 (1.9%) |
| Conjunctivitis | 0 | 6 (1.9%) |
| HLGT: Retina, choroid and vitreous haemorrhages and vascular disorders | 2 (1.2%) | 4 (1.2%) |
| HLT: Retinopathies NEC | 2 (1.2%) | 4 (1.2%) |
| Diabetic retinopathy | 1 (0.6%) | 4 (1.2%) |
| HLGT: Vision disorders | 4 (2.5%) | 5 (1.5%) |
| HLT: Visual disorders NEC | 4 (2.5%) | 4 (1.2%) |
| Vision blurred | 4 (2.5%) | 4 (1.2%) |
| EAR AND LABYRINTH DISORDERS | 10 (6.2%) | 11 (3.4%) |
| HLGT: External ear disorders (excl congenital) | 2 (1.2%) | 0 |
| HLT: External ear disorders NEC | 2 (1.2%) | 0 |
| Cerumen impaction | 2 (1.2%) | 0 |
| HLGT: Inner ear and VIIIth cranial nerve disorders | 6 (3.7%) | 7 (2.2%) |
| HLT: Inner ear signs and symptoms | 6 (3.7%) | 6 (1.9%) |
| Tinnitus | 2 (1.2%) | 2 (0.6%) |
| Vertigo | 4 (2.5%) | 3 (0.9%) |
| CARDIAC DISORDERS | 11 (6.8%) | 22 (6.8%) |
| HLGT: Cardiac arrhythmias | 6 (3.7%) | 8 (2.5%) |
| HLT: Supraventricular arrhythmias | 5 (3.1%) | 4 (1.2%) |
| Atrial fibrillation | 4 (2.5%) | 1 (0.3%) |
| HLGT: Cardiac disorder signs and symptoms | 1 (0.6%) | 6 (1.9%) |
| HLT: Cardiac signs and symptoms NEC | 0 | 6 (1.9%) |
| Palpitations | 0 | 6 (1.9%) |
| HLGT: Myocardial disorders | 2 (1.2%) | 0 |
| HLT: Myocardial disorders NEC | 2 (1.2%) | 0 |
| Left ventricular hypertrophy | 2 (1.2%) | 0 |
| VASCULAR DISORDERS | 12 (7.5%) | 26 (8.0%) |
| HLGT: Vascular hypertensive disorders | 9 (5.6%) | 17 (5.3%) |
| HLT: Vascular hypertensive disorders NEC | 9 (5.6%) | 17 (5.3%) |
| Hypertension | 9 (5.6%) | 17 (5.3%) |
| RESPIRATORY, THORACIC AND MEDIASTINAL DISORDERS | 27 (16.8%) | 48 (14.9%) |
| HLGT: Bronchial disorders (excl neoplasms) | 4 (2.5%) | 4 (1.2%) |
| HLT: Bronchospasm and obstruction | 4 (2.5%) | 4 (1.2%) |
| Asthma | 2 (1.2%) | 2 (0.6%) |
| HLGT: Respiratory disorders NEC | 18 (11.2%) | 40 (12.4%) |
| HLT: Breathing abnormalities | 1 (0.6%) | 11 (3.4%) |
| Dyspnoea | 0 | 7 (2.2%) |
| HLT: Coughing and associated symptoms | 11 (6.8%) | 18 (5.6%) |
| Cough | 11 (6.8%) | 18 (5.6%) |
| HLT: Upper respiratory tract signs and symptoms | 6 (3.7%) | 13 (4.0%) |
| Oropharyngeal pain | 3 (1.9%) | 8 (2.5%) |
| HLGT: Upper respiratory tract disorders (excl infections) | 6 (3.7%) | 12 (3.7%) |
| HLT: Nasal congestion and inflammations | 2 (1.2%) | 5 (1.5%) |
| Nasal congestion | 2 (1.2%) | 2 (0.6%) |

TABLE 30-continued

Number (%) of patients experiencing common TEAE(s) (PT ≥1% in any treatment group) presented by primary SOC, HLGT, HLT and PT during the on-treatment period of the whole study - Safety population

| PRIMARY SYSTEM ORGAN CLASS<br>  HLGT: High Level Group Term<br>    HLT: High Level Term<br>      Preferred Term | Placebo<br>(N = 161) | Lixisenatide<br>(N = 323) |
|---|---|---|
| HLT: Paranasal sinus disorders (excl infections and neoplasms) | 4 (2.5%) | 6 (1.9%) |
|   Sinus congestion | 4 (2.5%) | 6 (1.9%) |
| GASTROINTESTINAL DISORDERS | 62 (38.5%) | 156 (48.3%) |
|   HLGT: Abdominal hernias and other abdominal wall conditions | 4 (2.5%) | 6 (1.9%) |
|     HLT: Umbilical hernias | 1 (0.6%) | 4 (1.2%) |
|       Umbilical hernia | 1 (0.6%) | 4 (1.2%) |
|   HLGT: Benign neoplasms gastrointestinal | 1 (0.6%) | 4 (1.2%) |
|     HLT: Benign neoplasms gastrointestinal (excl oral cavity) | 1 (0.6%) | 4 (1.2%) |
|       Colonic polyp | 1 (0.6%) | 4 (1.2%) |
|   HLGT: Dental and gingival conditions | 3 (1.9%) | 11 (3.4%) |
|     HLT: Dental pain and sensation disorders | 3 (1.9%) | 4 (1.2%) |
|       Toothache | 2 (1.2%) | 4 (1.2%) |
|   HLGT: Gastrointestinal inflammatory conditions | 8 (5.0%) | 14 (4.3%) |
|     HLT: Gastritis (excl infective) | 8 (5.0%) | 9 (2.8%) |
|       Gastritis | 8 (5.0%) | 9 (2.8%) |
|   HLGT: Gastrointestinal motility and defaecation conditions | 27 (16.8%) | 53 (16.4%) |
|     HLT: Diarrhoea (excl infective) | 23 (14.3%) | 35 (10.8%) |
|       Diarrhoea | 23 (14.3%) | 35 (10.8%) |
|     HLT: Gastrointestinal atonic and hypomotility disorders NEC | 6 (3.7%) | 21 (6.5%) |
|       Constipation | 4 (2.5%) | 13 (4.0%) |
|       Gastrooesophageal reflux disease | 3 (1.9%) | 10 (3.1%) |
|   HLGT: Gastrointestinal signs and symptoms | 42 (26.1%) | 113 (35.0%) |
|     HLT: Dyspeptic signs and symptoms | 6 (3.7%) | 6 (1.9%) |
|       Dyspepsia | 6 (3.7%) | 5 (1.5%) |
|     HLT: Flatulence, bloating and distension | 2 (1.2%) | 13 (4.0%) |
|       Abdominal distension | 1 (0.6%) | 5 (1.5%) |
|       Flatulence | 1 (0.6%) | 9 (2.8%) |
|     HLT: Gastrointestinal and abdominal pains (excl oral and throat) | 10 (6.2%) | 16 (5.0%) |
|       Abdominal pain | 6 (3.7%) | 7 (2.2%) |
|       Abdominal pain lower | 3 (1.9%) | 2 (0.6%) |
|       Abdominal pain upper | 3 (1.9%) | 6 (1.9%) |
|     HLT: Gastrointestinal signs and symptoms NEC | 6 (3.7%) | 8 (2.5%) |
|       Abdominal discomfort | 5 (3.1%) | 7 (2.2%) |
|     HLT: Nausea and vomiting symptoms | 25 (15.5%) | 91 (28.2%) |
|       Nausea | 22 (13.7%) | 84 (26.0%) |
|       Vomiting | 8 (5.0%) | 26 (8.0%) |
| SKIN AND SUBCUTANEOUS TISSUE DISORDERS | 21 (13.0%) | 52 (16.1%) |
|   HLGT: Epidermal and dermal conditions | 14 (8.7%) | 39 (12.1%) |
|     HLT: Dermatitis and eczema | 6 (3.7%) | 14 (4.3%) |
|       Dermatitis | 2 (1.2%) | 4 (1.2%) |
|       Dermatitis contact | 1 (0.6%) | 5 (1.5%) |
|       Eczema | 2 (1.2%) | 3 (0.9%) |
|     HLT: Erythemas | 2 (1.2%) | 1 (0.3%) |
|       Erythema | 2 (1.2%) | 1 (0.3%) |
|     HLT: Pruritus NEC | 2 (1.2%) | 9 (2.8%) |
|       Pruritus | 2 (1.2%) | 9 (2.8%) |
|     HLT: Rashes, eruptions and exanthems NEC | 3 (1.9%) | 15 (4.6%) |
|       Rash | 3 (1.9%) | 13 (4.0%) |
|   HLGT: Skin appendage conditions | 7 (4.3%) | 9 (2.8%) |
|     HLT: Alopecias | 2 (1.2%) | 1 (0.3%) |
|       Alopecia | 2 (1.2%) | 1 (0.3%) |
|     HLT: Apocrine and eccrine gland disorders | 5 (3.1%) | 4 (1.2%) |
|       Heat rash | 2 (1.2%) | 0 |
|       Hyperhidrosis | 3 (1.9%) | 4 (1.2%) |
|   HLGT: Skin vascular abnormalities | 0 | 5 (1.5%) |
|     HLT: Purpura and related conditions | 0 | 5 (1.5%) |
|       Ecchymosis | 0 | 4 (1.2%) |
| MUSCULOSKELETAL AND CONNECTIVE TISSUE DISORDERS | 43 (26.7%) | 99 (30.7%) |
|   HLGT: Joint disorders | 17 (10.6%) | 41 (12.7%) |
|     HLT: Joint related disorders NEC | 3 (1.9%) | 4 (1.2%) |
|       Rotator cuff syndrome | 2 (1.2%) | 2 (0.6%) |
|     HLT: Joint related signs and symptoms | 11 (6.8%) | 25 (7.7%) |
|       Arthralgia | 11 (6.8%) | 24 (7.4%) |
|     HLT: Osteoarthropathies | 5 (3.1%) | 11 (3.4%) |
|       Osteoarthritis | 4 (2.5%) | 10 (3.1%) |
|   HLGT: Muscle disorders | 11 (6.8%) | 18 (5.6%) |
|     HLT: Muscle pains | 3 (1.9%) | 7 (2.2%) |
|       Myalgia | 3 (1.9%) | 6 (1.9%) |
|     HLT: Muscle related signs and symptoms NEC | 8 (5.0%) | 9 (2.8%) |

TABLE 30-continued

Number (%) of patients experiencing common TEAE(s) (PT ≥1% in any treatment group) presented by primary SOC, HLGT, HLT and PT during the on-treatment period of the whole study - Safety population

| PRIMARY SYSTEM ORGAN CLASS<br>HLGT: High Level Group Term<br>HLT: High Level Term<br>Preferred Term | Placebo<br>(N = 161) | Lixisenatide<br>(N = 323) |
|---|---|---|
| Muscle spasms | 8 (5.0%) | 9 (2.8%) |
| HLGT: Musculoskeletal and connective tissue deformities (incl intervertebral disc disorders) | 4 (2.5%) | 2 (0.6%) |
| HLT: Intervertebral disc disorders NEC | 2 (1.2%) | 2 (0.6%) |
| Intervertebral disc protrusion | 2 (1.2%) | 2 (0.6%) |
| HLGT: Musculoskeletal and connective tissue disorders NEC | 24 (14.9%) | 54 (16.7%) |
| HLT: Musculoskeletal and connective tissue pain and discomfort | 22 (13.7%) | 51 (15.8%) |
| Back pain | 14 (8.7%) | 22 (6.8%) |
| Flank pain | 2 (1.2%) | 5 (1.5%) |
| Musculoskeletal pain | 4 (2.5%) | 9 (2.8%) |
| Neck pain | 3 (1.9%) | 4 (1.2%) |
| Pain in extremity | 8 (5.0%) | 15 (4.6%) |
| HLT: Musculoskeletal and connective tissue signs and symptoms NEC | 2 (1.2%) | 2 (0.6%) |
| Musculoskeletal stiffness | 2 (1.2%) | 2 (0.6%) |
| HLGT: Synovial and bursal disorders | 2 (1.2%) | 8 (2.5%) |
| HLT: Bursal disorders | 1 (0.6%) | 6 (1.9%) |
| Bursitis | 1 (0.6%) | 6 (1.9%) |
| RENAL AND URINARY DISORDERS | 10 (6.2%) | 24 (7.4%) |
| HLGT: Urolithiases | 2 (1.2%) | 8 (2.5%) |
| HLT: Renal lithiasis | 2 (1.2%) | 8 (2.5%) |
| Nephrolithiasis | 2 (1.2%) | 7 (2.2%) |
| GENERAL DISORDERS AND ADMINISTRATION SITE CONDITIONS | 32 (19.9%) | 84 (26.0%) |
| HLGT: Administration site reactions | 7 (4.3%) | 23 (7.1%) |
| HLT: Injection site reactions | 7 (4.3%) | 22 (6.8%) |
| Injection site erythema | 0 | 5 (1.5%) |
| Injection site haematoma | 3 (1.9%) | 8 (2.5%) |
| Injection site pain | 4 (2.5%) | 5 (1.5%) |
| Injection site pruritus | 0 | 4 (1.2%) |
| Injection site reaction | 1 (0.6%) | 4 (1.2%) |
| HLGT: Body temperature conditions | 3 (1.9%) | 6 (1.9%) |
| HLT: Febrile disorders | 2 (1.2%) | 6 (1.9%) |
| Pyrexia | 2 (1.2%) | 6 (1.9%) |
| HLGT: General system disorders NEC | 24 (14.9%) | 65 (20.1%) |
| HLT: Asthenic conditions | 5 (3.1%) | 30 (9.3%) |
| Asthenia | 2 (1.2%) | 10 (3.1%) |
| Fatigue | 3 (1.9%) | 21 (6.5%) |
| HLT: General signs and symptoms NEC | 1 (0.6%) | 7 (2.2%) |
| Influenza like illness | 0 | 4 (1.2%) |
| HLT: Oedema NEC | 12 (7.5%) | 23 (7.1%) |
| Oedema | 3 (1.9%) | 6 (1.9%) |
| Oedema peripheral | 9 (5.6%) | 17 (5.3%) |
| HLT: Pain and discomfort NEC | 7 (4.3%) | 11 (3.4%) |
| Chest discomfort | 2 (1.2%) | 1 (0.3%) |
| Non-cardiac chest pain | 0 | 5 (1.5%) |
| Pain | 5 (3.1%) | 3 (0.9%) |
| HLGT: Tissue disorders NEC | 3 (1.9%) | 2 (0.6%) |
| HLT: Mass conditions NEC | 2 (1.2%) | 2 (0.6%) |
| Cyst | 2 (1.2%) | 1 (0.3%) |
| INVESTIGATIONS | 20 (12.4%) | 40 (12.4%) |
| HLGT: Endocrine investigations (incl sex hormones) | 7 (4.3%) | 10 (3.1%) |
| HLT: Gastrointestinal, pancreatic and APUD hormone analyses | 6 (3.7%) | 10 (3.1%) |
| Blood calcitonin increased | 6 (3.7%) | 10 (3.1%) |
| HLGT: Gastrointestinal investigations | 4 (2.5%) | 6 (1.9%) |
| HLT: Digestive enzymes | 3 (1.9%) | 6 (1.9%) |
| Blood amylase increased | 1 (0.6%) | 4 (1.2%) |
| Lipase increased | 3 (1.9%) | 6 (1.9%) |
| HLGT: Lipid analyses | 1 (0.6%) | 4 (1.2%) |
| HLT: Triglyceride analyses | 1 (0.6%) | 4 (1.2%) |
| Blood triglycerides increased | 1 (0.6%) | 4 (1.2%) |
| HLGT: Metabolic, nutritional and blood gas investigations | 6 (3.7%) | 7 (2.2%) |
| HLT: Carbohydrate tolerance analyses (incl diabetes) | 5 (3.1%) | 5 (1.5%) |
| Blood glucose decreased | 4 (2.5%) | 4 (1.2%) |
| HLGT: Physical examination topics | 3 (1.9%) | 7 (2.2%) |
| HLT: Physical examination procedures | 3 (1.9%) | 7 (2.2%) |
| Weight increased | 2 (1.2%) | 5 (1.5%) |
| INJURY, POISONING AND PROCEDURAL COMPLICATIONS | 20 (12.4%) | 60 (18.6%) |
| HLGT: Bone and joint injuries | 6 (3.7%) | 26 (8.0%) |
| HLT: Limb injuries NEC (incl traumatic amputation) | 5 (3.1%) | 17 (5.3%) |

TABLE 30-continued

Number (%) of patients experiencing common TEAE(s) (PT ≥1% in any treatment group) presented by primary SOC, HLGT, HLT and PT during the on-treatment period of the whole study - Safety population

| PRIMARY SYSTEM ORGAN CLASS<br>HLGT: High Level Group Term<br>HLT: High Level Term<br>Preferred Term | Placebo<br>(N = 161) | Lixisenatide<br>(N = 323) |
|---|---|---|
| Joint sprain | 2 (1.2%) | 6 (1.9%) |
| Limb injury | 0 | 9 (2.8%) |
| Meniscus lesion | 3 (1.9%) | 1 (0.3%) |
| HLGT: Injuries NEC | 12 (7.5%) | 41 (12.7%) |
| HLT: Muscle, tendon and ligament injuries | 3 (1.9%) | 7 (2.2%) |
| Muscle strain | 3 (1.9%) | 4 (1.2%) |
| HLT: Non-site specific injuries NEC | 4 (2.5%) | 17 (5.3%) |
| Fall | 1 (0.6%) | 5 (1.5%) |
| Road traffic accident | 2 (1.2%) | 3 (0.9%) |
| HLT: Site specific injuries NEC | 2 (1.2%) | 3 (0.9%) |
| Tooth fracture | 2 (1.2%) | 1 (0.3%) |
| HLT: Skin injuries NEC | 5 (3.1%) | 17 (5.3%) |
| Contusion | 5 (3.1%) | 12 (3.7%) |
| Excoriation | 0 | 4 (1.2%) |
| SURGICAL AND MEDICAL PROCEDURES | 5 (3.1%) | 6 (1.9%) |
| HLGT: Head and neck therapeutic procedures | 2 (1.2%) | 2 (0.6%) |
| HLT: Paranasal therapeutic procedures | 2 (1.2%) | 1 (0.3%) |
| Sinus operation | 2 (1.2%) | 1 (0.3%) |
| HLGT: Vascular therapeutic procedures | 2 (1.2%) | 2 (0.6%) |
| HLT: Arterial therapeutic procedures (excl aortic) | 2 (1.2%) | 2 (0.6%) |
| Coronary artery bypass | 2 (1.2%) | 0 |

TEAE: Treatment Emergent Adverse Event, SOC: System Organ Class, HLGT: High Level Group Term, HLT: High Level Term, PT: Preferred Term.
MedDRA version: 14.0.
n (%) = number and percentage of patients with at least one TEAE.
Note:
on-treatment period of the whole study = the time from the first dose of double-blind study medication up to 3 days after the last dose administration.
Table sorted by SOC internationally agreed order and HLGT, HLT, PT by alphabetic order.
Only SOC with at least one PT ≥ 1% in at least one group are presented.

The invention claimed is:

1. A method for improvement of glycemic control in a patient having diabetes type 2, comprising administering to the patient a therapeutically effective amount of the pharmaceutical combination comprising:

(a) desPro$^{36}$Exendin-4(1-39)-Lys$_6$-NH$_2$ and/or a pharmaceutically acceptable salt thereof, and (b) a glitazone and/or a pharmaceutically acceptable salt thereof; and wherein the patient has a haemoglobin A1c (HbA$_{1c}$) value of at least 8% and a fasting plasma glucose of at least 9 mmol/L when treated with glitazone alone.

2. The method of claim 1, wherein the patient is an adult.

* * * * *